United States Patent
Balog et al.

(10) Patent No.: US 7,550,458 B2
(45) Date of Patent: Jun. 23, 2009

(54) TRICYCLOUNDECANE COMPOUNDS USEFUL AS MODULATORS OF NUCLEAR HORMONE RECEPTOR FUNCTION

(75) Inventors: James Aaron Balog, Lambertville, NJ (US); David John Fairfax, Slingerlands, NY (US); Gregory Scott Martin, Guilderland, NY (US); Mark E. Salvati, Lawrenceville, NJ (US); Hai-Yun Xiao, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 424 days.

(21) Appl. No.: 11/581,873

(22) Filed: Oct. 17, 2006

(65) Prior Publication Data

US 2007/0088029 A1   Apr. 19, 2007

Related U.S. Application Data

(60) Provisional application No. 60/727,617, filed on Oct. 18, 2005.

(51) Int. Cl.
*C07D 491/14* (2006.01)
*C07D 471/14* (2006.01)
*A61K 31/5383* (2006.01)
*A61K 31/4745* (2006.01)

(52) U.S. Cl. .................... 514/229.8; 544/101
(58) Field of Classification Search ............... 544/101; 514/229.8
See application file for complete search history.

(56) References Cited

U.S. PATENT DOCUMENTS 5,387,687 A    2/1995  Scrima et al.

OTHER PUBLICATIONS

Brown, D. S. et al., "Ligand Effects in the Rhodium(II)-Catalyzed Reactions of α-Diazoamides", J. Org. Chem., vol. 59, pp. 2447-2455 (1994).
Cartoon, M. E. K. et al., "Pyrazines. Part 5. Preparation of 3,8-Diazabicyclo[.2.1]octane-2,4-dione Derivatives", J. Chem. Soc. Perkin I, vol. 7, pp. 1603-1606 (1980).
Tanaka, T. et al., "Oxidation of 2,6-Piperazinediones", Bulletin of the Chemical Society of Japan, vol. 50, No. 7, pp. 1821-1823 (1977).
Tanaka, T. et al., "Reaction of 1,4-disubstituted 2,6-piperazinediones with chloranil", Nippon Kagaku Kaishi, vol. 9, pp. 1450-1453 (1976).

*Primary Examiner*—Kahsay T Habte
(74) *Attorney, Agent, or Firm*—Gary D. Greenblatt

(57) ABSTRACT

Tricycloundecanes compounds, methods of using such compounds in the treatment of nuclear hormone receptor-associated conditions such as cancer and immune disorders, and pharmaceutical compositions containing such compounds are disclosed.

11 Claims, No Drawings

TRICYCLOUNDECANE COMPOUNDS USEFUL AS MODULATORS OF NUCLEAR HORMONE RECEPTOR FUNCTION

CROSS-REFERENCE TO RELATED APPLICATION

This application claims the benefit of United States Provisional Application Ser. No. 60/727,617, filed Oct. 18, 2005, the contents of which are hereby incorporated by reference in its entirety.

FIELD OF THE INVENTION

The present invention relates to tricycloundecane compounds, to methods of using such compounds in the treatment of nuclear hormone receptor-associated conditions such as cancer, and to pharmaceutical compositions containing such compounds.

BACKGROUND OF THE INVENTION

Nuclear hormone receptors (NHR's) constitute a large super-family of ligand-dependent and sequence-specific transcription factors. Members of this family influence transcription either directly, through specific binding to the promoter target genes (Evans, in *Science* 240: 889-895 (1988)), or indirectly, via protein-protein interactions with other transcription factors (Jonat et al., *Cell* 62: 1189-1204 (1990), Schuele et al., *Cell* 62: 1217-1226 (1990), and Yang-Yen et al., *Cell* 62: 1205-1215 (1990)). The nuclear hormone receptor super-family (also known in the art as the "steroid/thyroid hormone receptor super-family") includes receptors for a variety of hydrophobic ligands, including cortisol, aldosterone, estrogen, progesterone, testosterone, vitamine D3, thyroid hormone, and retinoic acid (Evans, 1988, supra). In addition to these conventional nuclear hormone receptors, the super-family contains a number of proteins that have no known ligands, termed orphan nuclear hormone receptors (Mangelsdorf et al., *Cell* 83: 835-839 (1995), O'Malley et al., *Mol. Endocrinol.* 10: 1293 (1996), Enmark et al., *Mol. Endocrinol.* 10, 1293-1307 (1996) and Giguere, *Endocrin. Rev.* 20, 689-725 (1999)). The conventional nuclear hormone receptors are generally transactivators in the presence of ligand, and can either be active repressors or transcriptionally inert in the absence of ligand. Some of the orphan receptors behave as if they are transcriptionally inert in the absence of ligand. Others, however, behave as either constitutive activators or repressors. These orphan nuclear hormone receptors are either under the control of ubiquitous ligands that have not been identified, or do not need to bind ligand to exert these activities.

In common with other transcription factors, the nuclear hormone receptors have a modular structure, being comprised of three distinct domains: an N-terminal domain of variable size containing a transcriptional activation function AF-1, a highly conserved DNA binding domain and a moderately conserved ligand-binding domain. The ligand-binding domain is not only responsible for binding the specific ligand but also contains a transcriptional activation function called AF-2 and a dimerisation domain (Wurtz et al., *Nature Struc. Biol.* 3, 87-94 (1996), Parker et al., *Nature Struc. Biol.* 3, 113-115 (1996) and Kumar et al., *Steroids* 64, 310-319 (1999)). Although the overall protein sequence of these receptors can vary significantly, all share both a common structural arrangement indicative of divergence from an ancestral archetype, and substantial homology (especially, sequence identity) at the ligand-binding domain.

The steroid binding nuclear hormone receptors (SB-NHR's) comprise a sub-family of nuclear hormone receptors. These receptors are related in that they share a stronger sequence homology to one another, particularly in the ligand binding domain (LBD), than to the other members of the NHR super-family (Evans, 1988, supra) and they all utilize steroid based ligands. Some examples of this sub-family of NHR's are the androgen receptor (AR), the estrogen receptor (ER), the progesterone receptor (PR), the glucocorticoid receptor (GR), the mineralocorticoid receptor (MR), the aldosterone receptor (ALDR), and the steroid and xenobiotic receptor (SXR) (Evans et al., WO 99/35246). Based on the strong sequence homology in the LBD, several orphan receptors may also be members of the SB-NHR sub-family.

Consistent with the high sequence homology found in the LBD for each of the SB-NHR's, the natural ligands for each is derived from a common steroid core. Examples of some of the steroid based ligands utilized by members of the SB-NHR's include cortisol, aldosterone, estrogen, progesterone, testosterone, and dihydrotestosterone. Specificity of a particular steroid based ligand for one SB-NHR versus another is obtained by differential substitution about the steroid core. High affinity binding to a particular SB-NHR, coupled with high level specificity for that particular SB-NHR, can be achieved with only minor structural changes about the steroid core (e.g., Waller et al., *Toxicol. Appl. Pharmacol.* 137, 219-227 (1996) and Mekenyan et al., *Environ. Sci. Technol.* 31, 3702-3711 (1997), binding affinity for progesterone towards the androgen receptor as compared to testosterone).

Numerous synthetically derived steroidal and non-steroidal agonists and antagonists have been described for the members of the SB-NHR family. Many of these agonist and antagonist ligands are used clinically in man to treat a variety of medical conditions. RU486 is an example of a synthetic agonist of the PR, which is utilized as a birth control agent (Vegeto et al., *Cell* 69: 703-713 (1992)), and Flutamide is an example of an antagonist of the AR, which is utilized for the treatment of prostate cancer (Neri et al, *Endo.* 91, 427-437 (1972)). Tamoxifen is an example of a tissues specific modulator of the ER function, that is used in the treatment of breast cancer (Smigel, *J. Natl. Cancer Inst.* 90, 647-648 (1998)). Tamoxifen can function as an antagonist of the ER in breast tissue while acting as an agonist of the ER in bone (Grese et al., *Proc. Natl. Acad. Sci. USA* 94, 14105-14110 (1997)). Because of the tissue selective effects seen for Tamoxifen, this agent and agents like it are referred to as "partial-agonist" or partial-antagonist". In addition to synthetically derived non-endogenous ligands, non-endogenous ligands for NHR's can be obtained from food sources (Regal et al., *Proc. Soc. Exp. Biol. Med.* 223, 372-378 (2000) and Hempstock et al., *J. Med. Food* 2, 267-269 (1999)). The flavanoid phytoestrogens are an example of a non-natural ligand for SB-NHR's that are readily obtained from a food source such as soy (Quella et al., *J. Clin. Oncol.* 18, 1068-1074 (2000) and Banz et al., *J. Med. Food* 2, 271-273 (1999)). The ability to modulate the transcriptional activity of individual NHR by the addition of a small molecule ligand, makes them ideal targets for the development of pharmaceutical agents for a variety of disease states.

As mentioned above, non-natural ligands can be synthetically engineered to serve as modulators of the function of NHR's. In the case of SB-NHR's, engineering of an non-natural ligand can include the identification of a core structure which mimics the natural steroid core system. This can be achieved by random screening against several SB-NHR's or through directed approaches using the available crystal structures of a variety of NHR ligand binding domains (Bourguet et al., *Nature* 375, 377-382 (1995), Brzozowski, et al., *Nature* 389, 753-758 (1997), Shiau et al., *Cell* 95, 927-937 (1998) and Tanenbaum et al., *Proc. Natl. Acad. Sci. USA* 95, 5998-6003 (1998)). Differential substitution about such a steroid mimic core can provide agents with selectivity for one receptor versus another. In addition, such modifications can be employed to obtain agents with agonist or antagonist activity for a particular SB-NHR. Differential substitution about the steroid mimic core can result in the formation of a series of high affinity agonists and antagonists with specificity for, for example, ER versus PR versus AR versus GR versus MR. Such an approach of differential substitution has been reported, for example, for quinoline based modulators of steroid NHR in *J. Med. Chem.*, 41, 623 (1999); WO 9749709; U.S. Pat. No. 5,696,133; U.S. Pat. No. 5,696,130; U.S. Pat. No. 5,696,127; U.S. Pat. No. 5,693,647; U.S. Pat. No. 5,693,646; U.S. Pat. No. 5,688,810; U.S. Pat. No. 5,688,808 and WO 9619458, all incorporated herein by reference.

The tricycloundecane compounds of the present invention comprise a core, which may serve as a steroid mimic, and are useful as modulators of the function of steroid binding nuclear hormone receptors, as well as other NHR as described herein.

SUMMARY OF THE INVENTION

The present invention provides tricycloundecane compounds of the following formula (I):

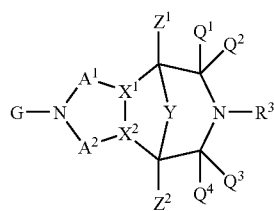

(I)

or pharmaceutically-acceptable salts, solvates, or prodrugs thereof;

wherein the symbols have the following meanings and are, for each occurrence, independently selected:

G is aryl, substituted aryl, heteroaryl, or substituted heteroaryl;

Y is O, $CR^1R^2$, CO, or $C(OR^1)_2$;

$A^1$ and $A^2$ are each independently CO and/or $CHR^1$;

one of $X^1$ and $X^2$ is $CR^1$, and the other of $X^1$ and $X^2$ is $CR^1$ or N;

$Z^1$ and $Z^2$ are each independently H, alkyl, substituted alkyl, alkenyl, substituted alkenyl, cycloalkyl, substituted cycloalkyl, cycloalkylalkyl, substituted cycloalkylalkyl, aryl, substituted aryl, arylalkyl, substituted arylalkyl, heterocyclo, substituted heterocyclo, heterocycloalkyl, and/or substituted heterocycloalkyl;

$Q^1$, $Q^2$, $Q^3$, and $Q^4$ are each independently H, alkyl, substituted alkyl, aryl, substituted aryl, heterocyclo, and/or substituted heterocyclo; or $Q^1$ and $Q^2$ together form =O; or $Q^3$ and $Q^4$ together form =O;

each $R^1$ and each $R^2$ are independently H, alkyl, substituted alkyl, cycloalkyl, substituted cycloalkyl, cycloalkylalkyl, substituted cycloalkylalkyl, arylalkyl, substituted arylalkyl, heterocycloalkyl, substituted heterocycloalkyl, aryl, substituted aryl, heteroaryl, substituted heteroaryl, CN, $NO_2$, F, Cl, and/or Br;

$R^3$ is H, alkyl, substituted alkyl, cycloalkyl, substituted cycloalkyl, cycloalkylalkyl, substituted cycloalkylalkyl, aryl, substituted aryl, arylalkyl, substituted arylalkyl, heterocyclo, substituted heterocyclo, heterocycloalkyl, substituted heterocycloalkyl, OH, $OR^1$, $NR^1R^2$, —C(=O)$R^1$, —C(=O)$OR^1$, —SO$_2R^1$, —SO$R^1$, —C(=O)$NR^1R^2$, —SO$_2OR^1$, —SO$_2NR^1R^2$, or —C(=N—CN)—$NR^1R^2$;

with the proviso that when either $X^1$ or $X^2$ is N, then Y is not O.

In one aspect of the present invention, there is provided a pharmaceutical composition comprising at least one tricycloundecane compound of formula I or a pharmaceutically acceptable salt, solvate, clathrate, or prodrug thereof, and a pharmaceutically acceptable carrier or diluent.

According to another aspect of the present invention, there is provided a method of modulating the function of a nuclear hormone receptor comprising administering to a mammalian species in need thereof, an effect amount of at least one tricycloundecane compound of formula I, or a pharmaceutically acceptable salt, solvate, clathrate, or prodrug thereof.

In still another aspect of the present invention, a method of treating a condition or disorder comprising administering to a mammalian species in need thereof a therapeutically effective amount of at least one tricycloundecane compound of formula I, or a pharmaceutically acceptable salt, solvate, clathrate, or prodrug thereof.

These as well as other aspects of the invention will become more apparent from the following detailed description.

FURTHER DESCRIPTION OF THE INVENTION

The following are definitions of terms used in the present specification. The initial definition provided for a group or term herein applies to that group or term throughout the present specification individually or as part of another group, unless otherwise indicated.

The terms "alkyl" and "alk" refers to a straight or branched chain alkane (hydrocarbon) radical containing from 1 to 12 carbon atoms, preferably 1 to 6 carbon atoms. Exemplary such groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. "Substituted alkyl" refers to an alkyl group substituted with one or more substituents, preferably 1 to 4 substituents, at any available point of attachment. Exemplary substituents include but are not limited to one or more of the following groups: halo (e.g., a single halo substituent or multiple halo substituents forming, in the latter case, groups such as a perfluoroalkyl group or an alkyl group bearing $Cl_3$ or $CF_3$), alkoxy, alkylthio, hydroxy, carboxy (i.e., —COOH), alkoxycarbonyl, alkylcarbonyloxy, CN, amino (i.e., —NH$_2$), alkylamino, dialkylamino, carbamoyl, substituted carbomoyl, carbamate, substituted carbamate, urea, substituted urea, amidinyl, substituted amidinyl, thiol (i.e., —SH), aryl, heterocycle, cycloalkyl, heterocycloalkyl, —S-aryl, —S-heterocycle, —S=O-aryl, —S=O-heterocycle, arylalkyl-O—, —S(O)$_2$-aryl, —S(O)$_2$-heterocycle, —NHS(O)$_2$-aryl, —NHS(O)$_2$-heterocycle, —NHS(O)$_2$NH-heterocycle, —NHS(O)$_2$NH-aryl, —P(O)$_2$-aryl, —P(O)$_2$-heterocycle, —NHP(O)$_2$-aryl, —NHP(O)$_2$-heterocycle, —NHP(O)$_2$NH-aryl, —NHP(O)$_2$NH-heterocycle, —O-aryl, —O-heterocycle, —NH-aryl, —NH-heterocycle, —NHC(=O)-aryl, —NHC(=O)-alkyl, —NHC(=O)-heterocycle, —OC(=O)-aryl, —OC(=O)- heterocycle, —NHC(=O)NH-aryl, —NHC(=O)NH-heterocycle, —OC(=O)O-alkyl, —OC(=O)O-aryl, —OC(=O)O-heterocycle, —OC(=O)NH-aryl, —OC(=O)NH-heterocycle, —NHC(=O)O-aryl, —NHC(=O)O-heterocycle, —NHC(=O)O-alkyl, —C(=O)NH-aryl, —C(=O)NH-heterocycle, —C(=O)O-aryl, —C(=O)O-heterocycle, —N(alkyl)S(O)$_2$-aryl, —N(alkyl)S(O)$_2$-heterocycle, —N(alkyl)S(O)$_2$NH-aryl, —N(alkyl)S(O)$_2$NH-heterocycle, —N(alkyl)P(O)$_2$-aryl, —N(alkyl)P(O)$_2$-heterocycle, —N(alkyl)P(O)$_2$NH-aryl, —N(alkyl)P(O)$_2$NH-heterocycle, —N(alkyl)-aryl, —N(alkyl)-heterocycle, —N(alkyl)C(=O)-aryl, —N(alkyl)C(=O)-heterocycle, —N(alkyl)C(=O)NH-aryl, —N(alkyl)C(=O)NH-heterocycle, —OC(=O)N(alkyl)-aryl, —OC(=O)N(alkyl)-heterocycle, —N(alkyl)C(=O)O-aryl, —N(alkyl)C(=O)O-heterocycle, —C(=O)N(alkyl)-aryl, —C(=O)N(alkyl)-heterocycle, —NHS(O)$_2$N(alkyl)-aryl, —NHS(O)$_2$N(alkyl)-heterocycle, —NHP(O)$_2$N(alkyl)-aryl, NHP(O)$_2$N(alkyl)-heterocycle, —NHC(=O)N(alkyl)-aryl, —NHC(=O)N(alkyl)-heterocycle, —N(alkyl)S(O)$_2$N(alkyl)-aryl, —N(alkyl)P(O)$_2$N(alkyl)-aryl, —N(alkyl)S(O)$_2$N(alkyl)-heterocycle, —N(alkyl)P(O)$_2$N(alkyl)-heterocycle, —N(alkyl)C(=O)N(alkyl)-aryl, and —N(alkyl)C(=O)N(alkyl)-heterocycle. In the aforementioned exemplary substituents, in each instance, groups such as "alkyl", "aryl" and "heterocycle" can themselves be optionally substituted; for example, "alkyl" in the group "NHC(=O)O-alkyl" recited above can be optionally substituted so that both "NHC(=O)O-alkyl" and "NHC(=O)O-substituted alkyl" are exemplary substituents.

The term "alkenyl" refers to a straight or branched chain hydrocarbon radical containing from 2 to 12 carbon atoms and at least one carbon-carbon double bond. Exemplary such groups include ethenyl or allyl. "Substituted alkenyl" refers to an alkenyl group substituted with one or more substituents, preferably 1 to 4 substituents, at any available point of attachment. Exemplary substituents include, but are not limited to, alkyl or substituted alkyl, as well as those groups recited above as exemplary alkyl substituents.

The term "cycloalkyl" refers to a fully saturated or partially saturated cyclic hydrocarbon group containing from 1 to 4 rings and 3 to 8 carbons per ring. Exemplary fully saturated cycloalkyl groups include cyclopropyl, cyclobutyl, cyclopentyl, and cyclohexyl. Exemplary partially saturated cycloalkyl groups include cyclobutenyl, cyclopentenyl, and cyclohexenyl. "Substituted cycloalkyl" refers to a cycloalkyl group substituted with one or more substituents, preferably 1 to 4 substituents, at any available point of attachment. Exemplary substituents include, but are not limited to, nitro, cyano, alkyl or substituted alkyl, as well as those groups recited above as exemplary alkyl substituents. Exemplary substituents also include spiro-attached or fused cyclic substituents, especially cycloalkenyl or substituted cycloalkenyl.

The terms "alkoxy" or "alkylthio" refer to an alkyl group as described above bonded through an oxygen linkage (—O—) or a sulfur linkage (—S—), respectively. The terms "substituted alkoxy" or "substituted alkylthio" refer to a substituted alkyl group as described above bonded through an oxygen or sulfur linkage, respectively.

The term "alkoxycarbonyl" refers to an alkoxy group bonded through a carbonyl group.

The term "alkylcarbonyl" refers to an alkyl group bonded through a carbonyl group. The term "alkylcarbonyloxy" refers to an alkylcarbonyl group bonded through an oxygen linkage.

The terms "arylalkyl", "substituted arylalkyl," "cycloalkylalkyl," "substituted cycloalkylalkyl," "cycloalkenylalkyl", "substituted cycloalkenylalkyl", "heterocycloalkyl" and "substituted heterocycloalkyl" refer to aryl, cycloalkyl, cycloalkenyl and heterocyclo groups bonded through an alkyl group, substituted on the aryl, cycloalkyl, cycloalkenyl, or heterocyclo and/or the alkyl group where indicated as "substituted."

The term "aryl" refers to cyclic, aromatic hydrocarbon groups which have 1 to 5 aromatic rings, especially monocyclic or bicyclic groups such as phenyl, biphenyl, or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" refers to an aryl group substituted by one or more substituents, preferably 1, 2, 3, 4, or 5 substituents, at any point of attachment. Exemplary substituents include, but are not limited to, nitro, cycloalkyl, substituted cycloalkyl, cycloalkenyl, substituted cycloalkenyl, cyano, alkyl-S(O)$_m$— (m=0, 1 or 2), alkyl, and substituted alkyl, as well as those groups recited above as exemplary alkyl substituents. Exemplary substituents also include fused cyclic substituents, such as heterocyclo, cycloalkenyl, substituted heterocyclo, and cycloalkenyl groups (e.g., thereby forming a fluoroenyl, tetrahydronapthalenyl, or dihydroindenyl group).

"Carbamoyl" refers to the group —C(=O)NH— which is bonded on one end to the remainder of the molecule and on the other to hydrogen or an organic moiety (such as alkyl, substituted alkyl, aryl, substituted aryl, heterocycle, alkylcarbonyl, hydroxyl, and substituted nitrogen). "Carbamate" refers to the group —O—C(=O)—NH— which is bonded on one end to the remainder of the molecule and on the other to hydrogen or an organic moiety (such as those listed above). "Urea" refers to the group —NH—C(=O)—NH— which is bonded on one end to the remainder of the molecule and on the other to hydrogen or an organic moiety (such as those listed above). "Amidinyl" refers to the group —C(=NH)(NH$_2$). "Substituted carbamoyl," "substituted carbamate," "substituted urea", and "substituted amidinyl" refer to carbamoyl, carbamate, urea, and amidinyl groups, respectively, as described above in which one more of the hydrogen groups are replaced by an organic moiety (such as those listed above).

The terms "heterocycle", heterocyclic" and "heterocyclo" refer to fully saturated, partially saturated, or fully unsaturated, including aromatic (i.e., "heteroaryl") cyclic groups (for example, 3 to 7 membered monocyclic, 7 to 11 membered bicyclic, or 10 to 16 membered tricyclic ring systems) that have at least one heteroatom in at least one carbon atom-containing ring. Each ring of the heterocyclic group containing a heteroatom may have 1, 2, 3, or 4 heteroatoms selected from nitrogen atoms, oxygen atoms, and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. Exemplary monocyclic heterocyclic groups include ethylene oxide, azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, and the like. Exemplary bicyclic heterocyclic groups include indolyl, isoindolyl, benzothiazolyl, benzodioxolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl], or furo[2,3-b]pyridinyl), dihydrobenzodioxinyl, dihydrodioxidobenzothiophenyl, dihydroisoindolyl, dihydroindolyl, dihydroquinolinyl, dihydroquinazolinyl (such as 3,4-dihydro-4-oxo-quinazolinyl), triazinylazepinyl, tetrahydroquinolinyl, and the like. Exemplary tricyclic heterocyclic groups include carbazolyl, benzidolyl, phenanthrolinyl, dibenzofuranyl, acridinyl, phenanthridinyl, xanthenyl, and the like.

"Substituted heterocycle," "substituted heterocyclic," and "substituted heterocyclo" (such as "substituted heteroaryl") refer to heterocycle, heterocyclic, or heterocyclo groups substituted with one or more substituents, preferably 1 to 4 substituents, at any available point of attachment. "Substituted heteroaryl" refers to an aromatic heterocyclic group substituted with one or more substituents, preferably 1 to 4 substitutents, at any available point of attachment. Exemplary substituents include, but are not limited to, cycloalkyl, substituted cycloalkyl, cycloalkenyl, substituted cycloalkenyl, nitro, oxo (i.e., =O), cyano, alkyl-S(O)$_m$— (m=0, 1, or 2), alkyl, and substituted alkyl, as well as those groups recited above as exemplary alkyl substituents.

The term "quaternary nitrogen" refers to a tetravalent positively charged nitrogen atom including, for example, the positively charged nitrogen in a tetraalkylammonium group (e.g., tetramethylammonium or N-methylpyridinium), the positively charged nitrogen in protonated ammonium species (e.g., trimethylhydroammonium or N-hydropyridinium), the positively charged nitrogen in amine N-oxides (e.g., N-methyl-morpholine-N-oxide or pyridine-N-oxide), and the positively charged nitrogen in an N-amino-ammonium group (e.g., N-aminopyridinium).

The terms "halogen" or "halo" refer to fluorine, chlorine, bromine, and iodine.

The terms "hydroxylamine" and "hydroxylamide" refer to the groups —NH—OH and —C(=O)—NH—OH, respectively.

When a functional group is termed "protected", this means that the group is in modified form to mitigate, especially preclude, undesired side reactions at the protected site. Suitable protecting groups for the methods and compounds described herein include, without limitation, those described in standard textbooks, such as Greene, T. W. et al., *Protective Groups in Organic Synthesis*, Wiley, N.Y. (1991).

Unless otherwise indicated, any heteroatom with unsatisfied valences is assumed to have hydrogen atoms sufficient to satisfy the valences.

Carboxylate anion refers to a negatively charged group —C(=O)O$^-$.

The tricycloundecane compounds of formula I may form salts which are also within the scope of this invention. Reference to a tricycloundecane compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as but not limited to a pyridine or imidazole, and an acidic moiety such as but not limited to a carboxylic acid, zwitterions may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the tricycloundecane compounds of the formula I may be formed, for example, by reacting a tricycloundecane compound of formula I with an amount of acid or base, such as an equivalent amount, in a medium such as one in which the salt precipitates or in an aqueous medium followed by lyophilization.

The tricycloundecane compounds of formula I may contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The tricycloundecane compounds of formula I may contain an acidic moiety, such but not limited to a carboxylic acid, may form salts with a variety of organic and inorganic bases. Exemplary basic salts include ammonium salts; alkali metal salts such as sodium, lithium, and potassium salts; alkaline earth metal salts such as calcium and magnesium salts; salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines; and salts with amino acids such as arginine, lysine, and the like. Basic nitrogen-containing groups may be quaternized with agents such as lower alkyl halides (e.g. methyl, ethyl, propyl, and butyl chlorides, bromides, and iodides), dialkyl sulfates (e.g. dimethyl, diethyl, dibutyl, and diamyl sulfates), long chain halides (e.g. decyl, lauryl, myristyl, and stearyl chlorides, bromides, and iodides), aralkyl halides (e.g. benzyl and phenethyl bromides), and others.

Prodrugs and solvates of the tricycloundecane compounds of the invention are also contemplated herein. The term "prodrug" as employed herein denotes a compound which, upon administration to a subject, undergoes chemical conversion by metabolic or chemical processes to yield a compound of the formula I, or a salt and/or solvate thereof. Solvates of the tricycloundecane compounds of formula I include, for example, hydrates.

All stereoisomers of the present compounds (for example, those which may exist due to asymmetric carbons on various substituents), including enantiomeric forms and diastereomeric forms, are contemplated within the scope of this invention. Individual stereoisomers of the tricycloundecane compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives, or separation by chiral column chromatography. The individual optical isomers can be obtained from the racemates by any suitable method, including without limitation, conventional methods, such as, for example, salt formation with an optically active acid followed by crystallization.

All configurational isomers of the tricycloundecane compounds of the present invention are contemplated, either in admixture, or in pure or substantially pure form. As can be appreciated, the preferred configuration can be a function of the particular compound and its preferred activity. Separation of configurational isomers can be achieved by any suitable method, such as column chromatography.

Throughout the specifications, groups and substituents thereof may be chosen to provide stable moieties and compounds.

Embodiments indicated herein as exemplary or preferred are intended to be illustrative and not limiting.

In one nonlimiting embodiment, the tricycloundecane compound of formula I has a structure in which $X^1$ and $X^2$ are each $CR^1$. The tricycloundecane compound of this embodiment has the formula II:

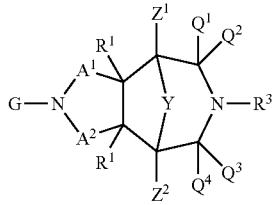
(II)

wherein $G$, $A^1$, $A^2$, each $R^1$, $Z^1$, $Z^2$, $Y$, $Q^1$, $Q^2$, $Q^3$, $Q^4$, and $R^3$ are defined herein above.

Preferably $A^1$ and $A^2$ are each CO in the tricycloundecane compound of formula II.

Preferably Y is O in the tricycloundecane compound of formula II.

Preferably, in the tricycloundecane compound of formula II, $Z^1$ and $Z^2$ are each independently hydrogen, alkyl, or substituted alkyl; more preferably hydrogen or lower alkyl; and most preferably hydrogen or methyl. Most preferably $Z^1$ and $Z^2$ are each methyl.

Preferably, in the tricycloundecane compound of formula II, G is substituted aryl, for example, a-substituted phenyl such as 3-trifluoromethyl, 4-cyano phenyl.

Preferably, in the tricycloundecane compound of formula II, $R^3$ is —C(=O)NR$^1$R$^2$, —C(=O)R$^1$, a piperazinyl group, or a substituted piperazinyl group. Examples of suitable piperazinyl groups and substituted piperazinyl groups are represented by formula (IV):

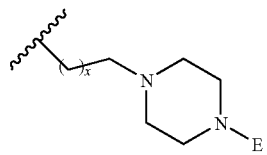
(IV)

wherein x is an integer in the range of from 1 to 8; and E is H, —C(=O)R$^1$, —C(=O)OR$^1$, —C(=O)R$^1$NH, —SO$_2$R$^1$, or —SO$_2$NHR$^1$. When $R^3$ is —C(=O)NR$^1$R$^2$ or —C(=O)R, it is more preferred that $R^1$ is aryl, substituted aryl, heteroaryl, or substituted heteroaryl, and $R^2$ is H or alkyl.

A preferred structure for the tricycloundecane compound of formula II has the formula IIa:

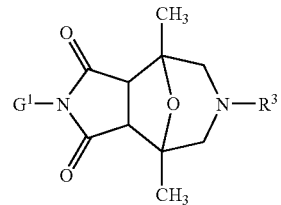
(IIa)

wherein $G^1$ is a substituted aryl. More preferably, in the tricycloundecane compound of formula IIa, $R^3$ is —C(=O)NR$^1$R$^2$, —C(=O)R$^1$, a piperazinyl group, or a substituted piperazinyl group. Preferably $R^1$ is aryl, substituted aryl, heteroaryl, or substituted heteroaryl, and $R^1$ is H or alkyl.

The structure of formula IIb represents one example of the tricycloundecane compound of formula IIa:

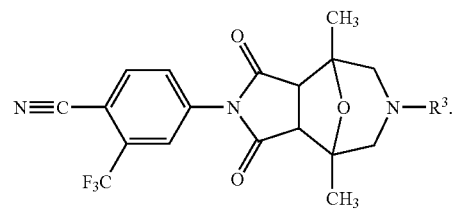
(IIb)

Preferably, $R^3$ in the tricycloundecane compound of formula IIa is —C(=O)NR$^1$R$^2$, more preferably, $R^3$ is C(=O)NHR$^2$, still more preferably, —C(=O)NHR$^2$ wherein $R^2$ is aryl or substituted aryl.

In a different nonlimiting embodiment, the tricycloundecane compound of formula I has a structure in which one of $X^1$ and $X^2$ is $CR^1$, and the other of $X^1$ and $X^2$ is N. The tricycloundecane compounds of this embodiment have the structures of formula IIIa or IIIb:

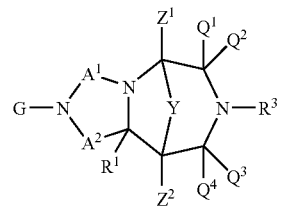
(IIIa)

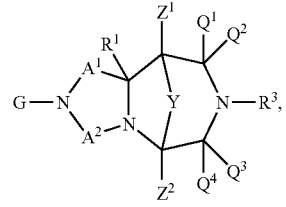
(IIIb)

wherein $G$, $A^1$, $A^2$, $Y$, $Z^1$, $Z^2$, $R^1$, $R^3$, $Q_1$, $Q_2$, $Q_3$, and $Q_4$, are defined hereinabove, with the proviso that Y is not O.

Preferably $A^1$ and $A^2$ are each CO in the tricycloundecane compounds of formulae IIIa and IIIb.

Preferably Y is CR$^1$R$^2$ in the tricycloundecane compound of formulae IIIa and IIIb. More preferably, Y is CH$_2$.

Preferably, in the tricycloundecane compound of formulae IIIa and IIIb, $Z^1$ and $Z^2$ are each independently hydrogen, alkyl, or substituted alkyl; more preferably hydrogen or lower alkyl; and most preferably hydrogen or methyl. Most preferably $Z^1$ and $Z^2$ are each methyl.

Preferably, in the tricycloundecane compound of formulae IIIa and IIIb, G is substituted aryl, for example, a substituted phenyl such as 3-trifluoromethyl, 4-cyano phenyl.

Preferably, in the tricycloundecane compound of formulae IIIa and IIIb, $R^3$ is —C(=O)NR$^1$R$^2$, —C(=O)R$^1$, a piperazinyl group, or a substituted piperazinyl group. Examples of suitable piperazinyl groups and substituted piperazinyl groups are represented by formula (IV), wherein x is an integer in the range of from 1 to 8; and E is H, —C(=O)R$^1$, —C(=O)OR$^1$, —C(=O)R$^1$NH, —SO$_2$R$^1$, or —SO$_2$NHR$^1$. Further, when $R^3$ is —C(=O)NR$^1$R$^2$ or —C(=O)R$^1$, preferably $R^1$ is preferably aryl, substituted aryl, heteroaryl, or substituted heteroaryl, and $R^2$ is H or alkyl.

Examples of preferred structures for the tricycloundecane compound of formulae IIIa and IIIb include, but are not limited to,

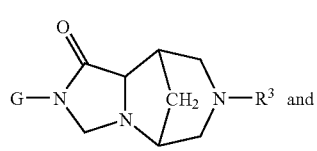

(IIIc)

and

(IIId)

In a still further non-limiting embodiment, the substituent group G of the tricycloundecane compound of formula I is selected from:

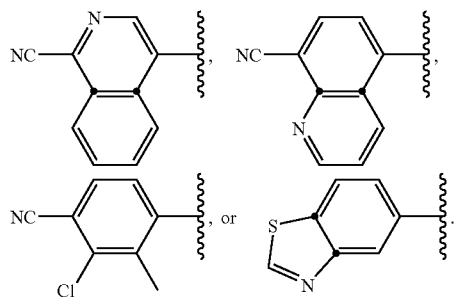

In another non-limiting embodiment, the substituent group G of the tricycloundecane compound of formula I is selected from optionally substituted phenyl, optionally substituted naphthyl, or optionally substituted fused bicyclic heterocyclic groups such as optionally substituted benzo-fused heterocyclic groups (e.g., bonded to the remainder of the molecule through the benzene portion), especially such groups wherein the heterocyclic ring bonded to benzene has five members exemplified by benzoxazole, benzothiazole, benzothiadiazole, benzoxadiazole, and benzothiophene, for example:

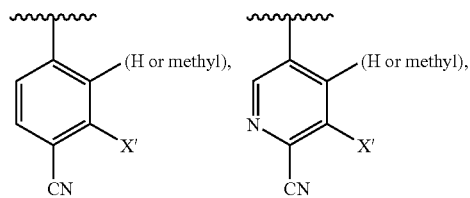

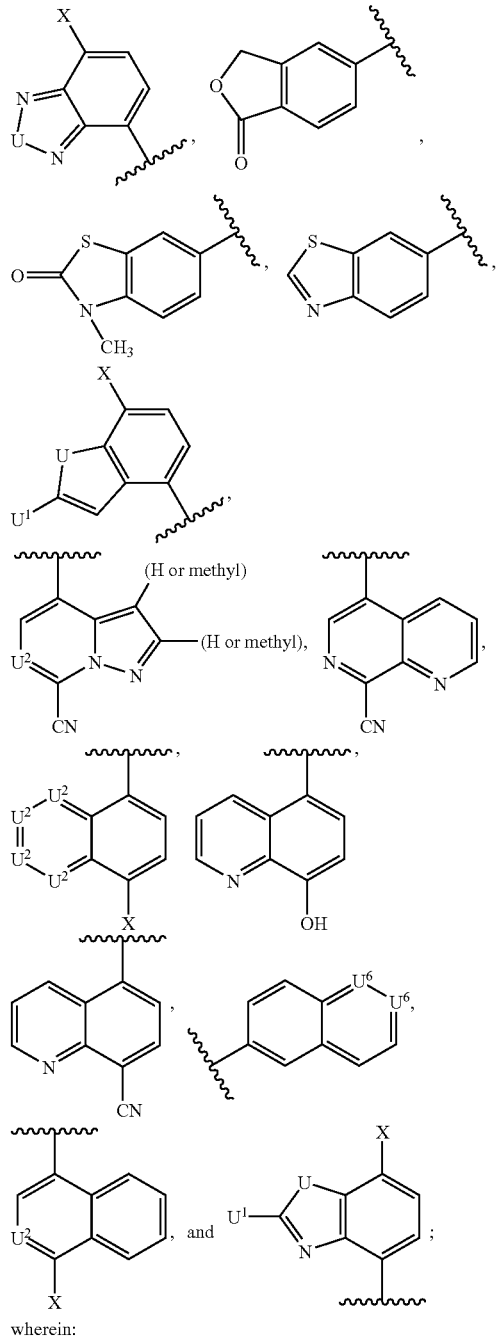

wherein:

X is halo (especially F), OH, CN, NO$_2$, or

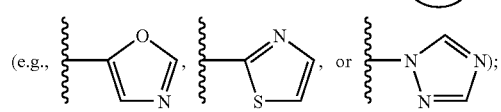

X' is halo (especially F, Cl, or I), CH$_3$, CF$_3$, CN, or OCH$_3$;
U is O or S (where S can optionally be oxygenated, e.g., to SO);
$U^1$ is CH$_3$ or CF$_3$;
each $U^2$ is independently H, CH, or CF;
$U^3$ is N, O, or S;

U[4] and U[5], together with the atoms to which they are bonded, form an optionally substituted 5-membered heterocyclic ring which can be partially unsaturated or aromatic and which contain 1 to 3 ring heteroatoms;
each U[6] is independently CH or N; and (P) denotes optional double bond(s) within the ring formed by U[3], U[4], and U[5].

In one embodiment, the tricycloundecane compound is selected from a compound in Table A:

TABLE A

| Structure | Name |
|---|---|
| 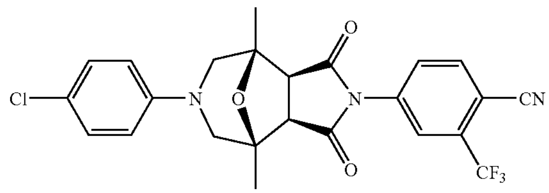 | 4-[(3aR,4R,8S,8aS)-6-(4-chlorophenyl)octahydro-4,8-dimethyl-1,3-dioxo-4,8-epoxypyrrolo[3,4-d]azepin-2(1H)-yl]-2-(trifluoromethyl)-benzonitrile |
| 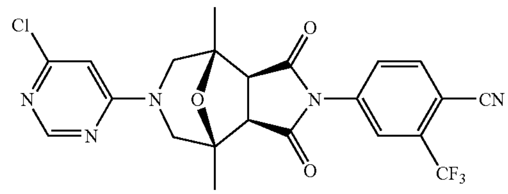 | 4-[(3aR,4R,8S,8aS)-6-(6-chloro-4-pyrimidinyl)octahydro-4,8-dimethyl-1,3-dioxo-4,8-epoxypyrrolo[3,4-d]azepin-2(1H)-yl]-2-(trifluoromethyl)-benzonitrile |
| 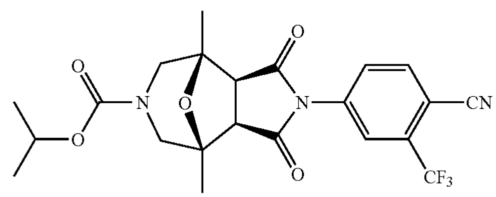 | 4,8-epoxypyrrolo[3,4-d]azepine-6(1H)-carboxylic acid,2-[4-cyano-3-(trifluoromethyl)phenyl]octahydro-4,8-dimethyl-1,3-dioxo-,1-methylethyl ester,(3aR,4R,8S,8a5)- |
| 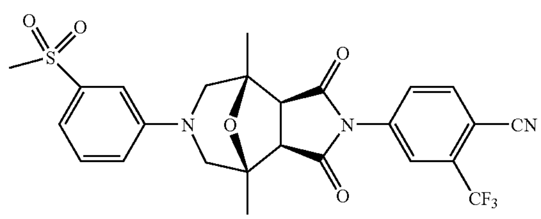 | 4-[(3aR,4R,8S,8aS)-octahydro-4,8-dimethyl-6-[3-(methylsulfonyl)phenyl]-1,3-dioxo-4,8-epoxypyrrolo[3,4-d]azepin-2(1H)-yl]-2-(trifluoromethyl)-benzonitrile |
| 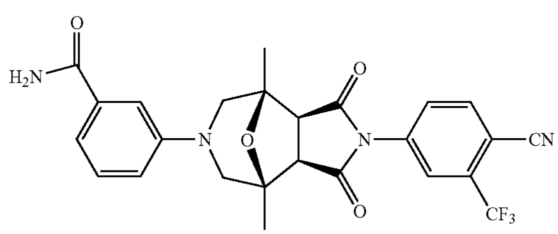 | 3-[(3aR,4R,8S,8aS)-2-[4-cyano-3-(trifluoromethyl)phenyl]octahydro-4,8-dimethyl-1,3-dioxo-4,8-epoxypyrrolo[3,4-d]azepin-6(1H)-yl]-benzamide |
| 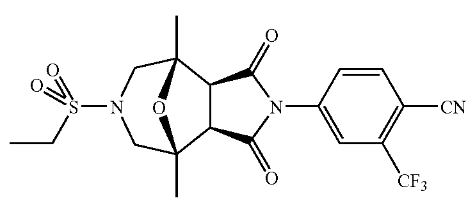 | 4-(9-Ethanesulfonyl-1,7-dimethyl-3,5-dioxo-11-oxa-4,9-diaza-tricyclo[5.3.1.0$^{2,6}$]undec-4-yl)-2-trifluoromethyl-benzonitrile |

TABLE A-continued

| Structure | Name |
|---|---|
| 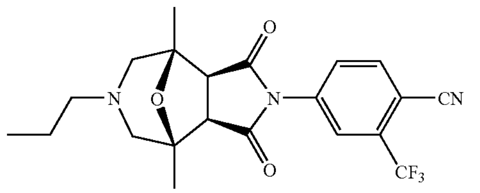 | 4-(1,7-Dimethyl-3,5-dioxo-9-propyl-11-oxa-4,9-diaza-tricyclo[5.3.1.0$^{2,6}$]undec-4-yl)-2-trifluoromethyl-benzonitrile |
| 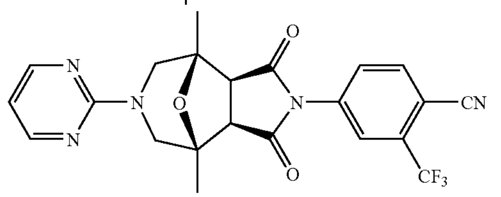 | 4-(1,7-Dimethyl-3,5-dioxo-9-pyrimidin-2-yl-11-oxa-4,9-diaza-tricyclo[5.3.1.0$^{2,6}$]undec-4-yl)-2-trifluoromethyl-benzonitrile |
| 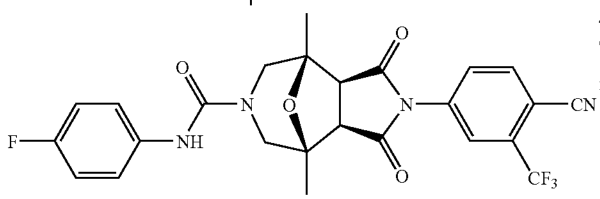 | 4,8-epoxypyrrolo[3,4-d]azepine-6(1H)-carboxamide,2-[4-cyano-3-(trifluoromethyl)phenyl]-N-(4-fluorophenyl)octahydro-4,8-dimethyl-1,3-dioxo-,(3aR,4R,8S,8aS)-benzonitrile |
| 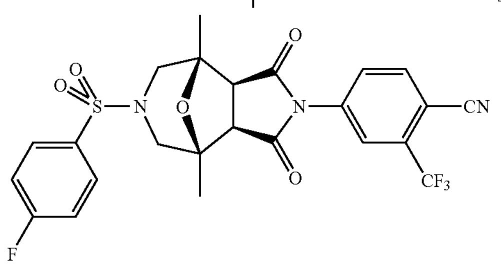 | 4,8-epoxypyrrolo[3,4-d]azepine-1,3(2H,4H)-dione,2-[4-cyano-3-(trifluoromethyl)phenyl]-6-[(4-fluorophenyl)sulfonyl]hexahydro-4,8-dimethyl-,(3aR,4R,8S,8aS)-benzonitrile |

METHODS OF PREPARATION

The compounds of the present invention may be prepared by methods such as those illustrated in the following Schemes 1 to 3. Solvents, temperatures, pressures, and other reaction conditions may readily be selected by one of ordinary skill in the art. Starting materials are commercially available or readily prepared by one skilled in the art. Combinatorial techniques may be employed in the preparation of compounds, for example, where the intermediates possess groups suitable for these techniques.

Scheme 1

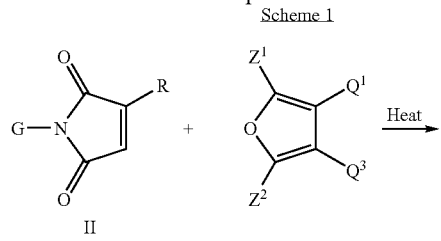

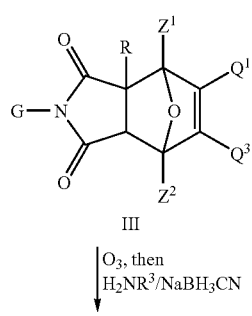

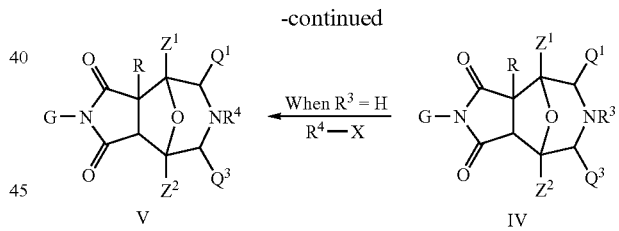

Scheme 1 demonstrates a possible synthesis of substituted 11-oxa-4,9-diaza-tricyclo[5.3.1.0$^{2,6}$]undecanes of formula V. The maleic imide of formula II can be heated with a furan to give the product of formula III via D-A reaction. Ozonolysis of the resultant double bond under conditions known to one skilled in the art will give the corresponding ozonide (Synthesis 1985 (6) 701). Reductive amination of the ozonide and the following transformations will give the substituted undecanes IV and V by methods known to one skilled in the art.

Scheme 2

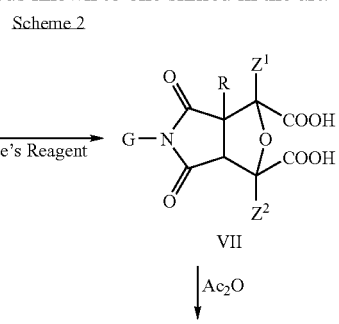

-continued

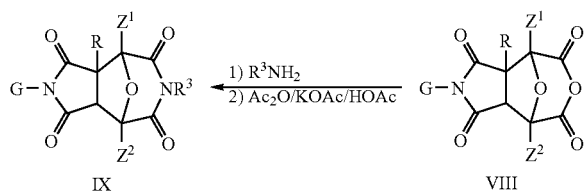

Ozonolysis of the Diels-Alder adduct of formula VI followed by Jone's oxidation under conditions known to one skilled in the art will give the acid of general formula VII. The formation of anhydride VIII, followed by coupling with an amine and dehydration under various conditions known to one skilled in the art, will give the compound of general formula IX.

followed by reduction with a reducing agent, such as sodium cyanoborohydride, in the presence of a primary amine to give compounds of general structure X.

Compound IX can also be treated directly with reducing agent such as sodium borohydride to give a compound of general structure XI. Treatment of compound XI with a base such as potassium tert-butoxide in the presence of an activating agent such as p-toluenesulfonyl chloride will generate a compound of general structure XII via cyclization. Treatment of compound XII with ozone gas in a solvent such as dichloromethane followed by a reducing agent, such as sodium cyanoborohydride, in the presence of a primary amine will give a compound of general structure XIII.

Oxidation of compound XI by Dess-Martin periodinane or other oxidants known to one skilled in the art, will give an aldehyde intermediate which can further be reacted with various organometallic agents, such as a Grignard reagent, to give a compound of general structure XIV. Treatment of compound XIV with a base such as potassium tert-butoxide in the

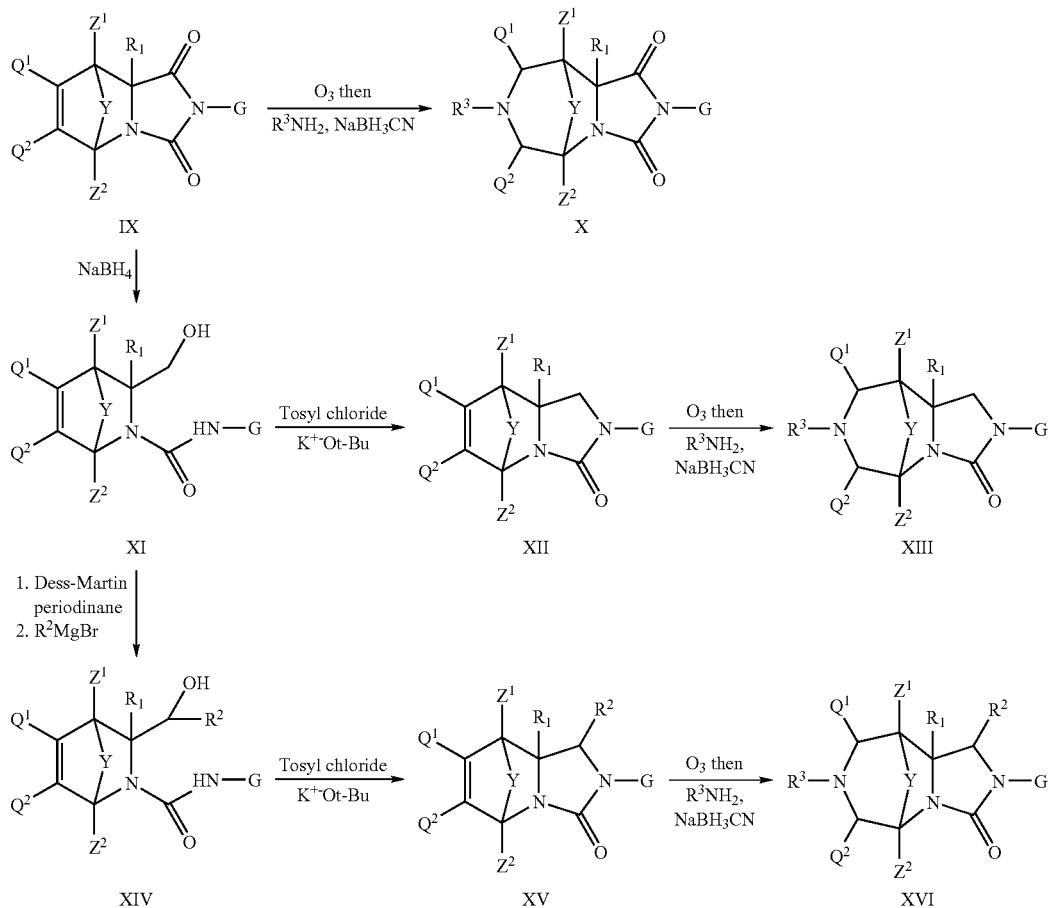

Scheme 3 depicts possible synthetic routes to compounds of general formulae X, XIII and XVI where A=C=O. A compound of general structure IX can be synthesized by methods reported in U.S. Patent Application Publication 2004/077606A1. Compound IX can be treated, by one skilled in the art, with ozone gas in a solvent such as dichloromethane presence of an activating agent such as p-toluenesulfonyl chloride will generate a compound of general structure XV via cyclization. Treatment of compound XV with ozone gas followed by a reducing agent such as sodium cyanoborohydride in the presence of a primary amine will give a compound of general structure XVI.

USE AND UTILITY

The tricycloundecane compounds of the present invention are useful for modulating the function of nuclear hormone receptors (NHR), and include compounds which are, for example, agonists, partial agonists, antagonists, or partial antagonists of the androgen receptor (AR), the estrogen receptor (ER), the progesterone receptor (PR), the glucocorticoid receptor (GR), the mineralocorticoid receptor (MR), the steroid and xenobiotic receptor (SXR), other steroid binding NHR's, the Orphan receptors, or other NHR's. Selective modulation of one such NHR relative to others within the NHR family is preferred. "Modulation" includes, for example, activation (e.g., agonist activity) or inhibition (e.g., antagonist activity).

The present tricycloundecane compounds are thus useful in the treatment of NHR-associated conditions. A "NHR-associated condition", as used herein, denotes a condition or disorder which can be treated by modulating the function of a NHR in a subject, wherein treatment comprises prevention, partial alleviation, or cure of the condition or disorder. Modulation may occur locally, for example, within certain tissues of the subject, or more extensively throughout a subject being treated for such a condition disorder.

The tricycloundecane compounds of the present invention are useful for the treatment of a variety of conditions and disorders including, but not limited to, those described following:

The tricycloundecane compounds of formula I can be applied as agonists, partial agonists, antagonists, or partial antagonists of the estrogen receptor, preferably selectively to that receptor, in an array of medical conditions which involve modulation of the estrogen receptor pathway. Applications of said compounds include but are not limited to: osteoporosis, hot flushes, vaginal dryness, prostate cancer, breast cancer, endometrial cancer, cancers expressing the estrogen receptor such as the aforementioned cancers and others, contraception, pregnancy termination, menopause, amennoreahea, and dysmennoreahea.

The tricycloundecane compounds of formula I can be applied as agonists, partial agonists, antagonists, or partial antagonists of the progesterone receptor, preferably selectively to that receptor, in an array of medical conditions which involve modulation of the progesterone receptor pathway. Applications of said compounds include but are not limited to: breast cancer, other cancers containing the progesterone receptor, endometriosis, cachexia, contraception, menopause, cyclesynchrony, meniginoma, dysmennoreahea, fibroids, pregnancy termination, labor induction, and osteoporosis.

The tricycloundecane compounds of formula I can be applied as agonists, partial agonists, antagonists, or partial antagonists of the glucocorticoid receptor, preferably selectively to that receptor, in an array of medical conditions which involve modulation of the glucocorticoid receptor pathway. Applications of said compounds include but are not limited to: inflammatory diseases, autoimmune diseases, prostate cancer, breast cancer, Alzheimer's disease, psychotic disorders, drug dependence, non-insulin dependent Diabetes Mellitus, and as dopamine receptor blocking agents or otherwise as agents for the treatment of dopamine receptor mediated disorders. Glucocorticoid receptor AP-1 ("GR AP-1") inhibitors (which compounds can, for example, avoid side effects connected with GR agonists) can be used as anti-inflammatory and immunosuppressive agents, for example, to treat a wide variety of inflammatory and autoimmune diseases. These diseases include without limitation: rheumatoid arthritis, osteoarthritis, inflammatory bowel disease, asthma, chronic obstructive pulmonary disease, prevention of transplant rejection, multiple sclerosis, and psoriasis, among others. GR AP-1 inhibitors of the present invention can be employed together with known GR AP-1 inhibitors, such as the steroid prednisone (which is used to treat the above diseases).

The tricycloundecane compounds of formula I can be applied as agonists, partial agonists, antagonists, or partial antagonists of the mineralocorticoid receptor, preferably selectively to that receptor, in an array of medical conditions which involve modulation of the mineralocorticoid receptor pathway. Applications of said compounds include but are not limited to: drug withdrawal syndrome and inflammatory diseases.

The tricycloundecane compounds of formula I can be applied as agonists, partial agonists, antagonists, or partial antagonists of the aldosterone receptor, preferably selectively to that receptor, in an array of medical conditions which involve modulation of the aldosterone receptor pathway. One application of said compounds includes but is not limited to: congestive heart failure.

The tricycloundecane compounds of formula I can be applied as agonists, partial agonists, antagonists, or partial antagonists of the androgen receptor, preferably selectively to that receptor, in an array of medical conditions which involve modulation of the androgen receptor pathway. Applications of said compounds include but are not limited to: hirsutism, acne, seborrhea, Alzheimer's disease, androgenic alopecia, hypogonadism, hyperpilosity, benign prostate hypertrophia, adenomas and neoplasies of the prostate (such as advanced metastatic prostate cancer), treatment of benign or malignant tumor cells containing the androgen receptor such as is the case for breast, brain, skin, ovarian, bladder, lymphatic, liver and kidney cancers, pancreatic cancers, modulation of VCAM expression and applications therein for the treatment of heart disease, inflammation and immune modulations, modulation of VEGF expression and the applications therein for use as antiangiogenic agents, osteoporosis, suppressing spermatogenesis, libido, cachexia, endometriosis, polycystic ovary syndrome, anorexia, androgen supplement for age related decreased testosterone levels in men, male menopause, male hormone replacement, male and female sexual dysfunction, and inhibition of muscular atrophy in ambulatory patients. For example, pan AR modulation is contemplated, with prostate selective AR modulation ("SARM") being particularly preferred, such as for the treatment of early stage prostate cancers. In one embodiment, the compounds of this invention is employed as an antagonist or partial antagonist to the androgen receptor in the treatment of prostate cancer.

The tricycloundecane compounds of formula I can be applied as (preferably, selective) antagonists of the mutated androgen receptor, for example, found in many tumor lines. Examples of such mutants are those found in representative prostate tumor cell lines such as LNCap, (T877A mutation, *Biophys. Acta,* 187, 1052 (1990)), PCa2b, (L701H & T877A mutations, *J. Urol.,* 162, 2192 (1999)) and CWR22, (H874Y mutation, *Mol. Endo.,* 11, 450 (1997)). Applications of said compounds include but are not limited to: adenomas and neoplasies of the prostate, breast cancer, and endometrial cancer.

The tricycloundecane compounds of formula I can be applied as agonists, partial agonists, antagonists, or partial antagonists of the steroid and xenobiotic receptor, preferably selectively to that receptor, in an array of medical conditions which involve modulation of the steroid and xenobiotic receptor pathway. Applications of said compounds include but are not limited to: treatment of disregulation of cholesterol homeostasis, attenuation of metabolism of pharmaceutical agents by co-administration of an agent (compound of the present invention) which modulates the P450 regulator effects of SXR.

Along with the aforementioned NHR, there also exist a number of NHR for which the activating or deactivating ligands may not be characterized. These proteins are classified as NHR due to strong sequence homology to other NHR, and are known as the Orphan receptors. Because the Orphan receptors demonstrate strong sequence homology to other NHR, compounds of formula I include those which serve as modulators of the function of the Orphan NHR. Orphan receptors that are modulated by NHR modulators such as compounds within the scope of formula I are exemplified, but not limited to, those listed in Table 1. Exemplary therapeutic applications of modulators of said Orphan receptors are also listed in Table 1, but are not limited to the examples therein.

TABLE 1

Exemplary Orphan nuclear hormone receptors, form (M = monomeric, D = heterodimeric, H = homodimeric), tissue expression and target therapeutic applications. (CNS = central nervous system)

| Receptor | Form | Tissue Expression | Target Therapeutic Application |
|---|---|---|---|
| NURR1 | M/D | Dopaminergic Neurons Muscle | Parkinson's Disease |
| RZRβ | M | Brain (Pituitary), | Sleep Disorders |
| RORα | M | Cerebellum, Purkinje Cells | Arthritis, Cerebellar Ataxia |
| NOR-1 | M | Brain, Muscle, Heart, Adrenal, Thymus | CNS Disorders, Cancer |
| NGFI-Bβ | M/D | Brain | CNS Disorders |
| COUP-Tfα | H | Brain | CNS Disorders |
| COUP-TFβ | H | Brain | CNS Disorders |
| COUP-TFγχ | H | Brain | CNS Disorders |
| Nur77 | H | Brain, Thymus, Adrenals | CNS Disorders |
| Rev-ErbAα | H | Muscle, Brain (Ubiquitous) | Obesity |
| HNF4α | H | Liver, Kidney, Intestine | Diabetes |
| SF-1 | M | Gonads, Pituitary | Metabolic Disorders |
| LXRα, β | D | Kidney (Ubiquitous) | Metabolic Disorders |
| GCNF | M/H | Testes, Ovary | Infertility |
| ERRα, β | M | Placenta, Bone | Infertility, Osteoporosis |
| FXR | D | Liver, Kidney | Metabolic Disorders |
| CARα | H | Liver, Kidney | Metabolic Disorders |
| PXR | H | Liver, Intestine | Metabolic Disorders |

The present invention thus provides methods for the treatment of NHR-associated conditions, comprising the step of administering to a subject in need thereof at least one tricycloundecane compound of formula I in an amount effective therefor. Other therapeutic agents such as those described below may be employed with the inventive compounds in the present methods (for example, separately, or formulated together as a fixed dose). In the methods of the present invention, such other therapeutic agent(s) can be administered prior to, simultaneously with, or following the administration of the tricycloundecane compound(s) of the present invention.

The present invention also provides pharmaceutical compositions comprising at least one of the tricycloundecane compounds of the formula I capable of treating a NHR-associated condition in an amount effective therefor, and a pharmaceutically acceptable carrier (vehicle or diluent). The compositions of the present invention can contain other therapeutic agents as described below, and can be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

It should be noted that the tricycloundecane compounds of the present invention are, without limitation as to their mechanism of action, useful in treating any of the conditions or disorders listed or described herein such as inflammatory diseases or cancers, or other proliferate diseases, and in compositions for treating such conditions or disorders.

The present compounds have therapeutic utility in the modulation of immune cell activation/proliferation, e.g., as competitive inhibitors of intercellular ligand/receptor binding reactions involving CAMs (Cellular Adhesion Molecules) and Leukointegrins. For example, the present compounds modulate LFA-ICAM 1, and are particularly useful as LFA-ICAM 1 antagonists, and in the treatment of all conditions associated with LFA-ICAM 1 such as immunological disorders. Preferred utilities for the present compounds include, but are not limited to: inflammatory conditions such as those resulting from a response of the non-specific immune system in a mammal (e.g., adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction or use with thrombolysis agents, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome) and conditions resulting from a response of the specific immune system in a mammal (e.g., psoriasis, organ/tissue transplant rejection, graft vs. host reactions and autoimmune diseases including Raynaud's syndrome, autoimmune thyroiditis, dermatitis, multiple sclerosis, rheumatoid arthritis, insulin-dependent diabetes mellitus, uveitis, inflammatory bowel disease including Crohn's disease and ulcerative colitis, and systemic lupus erythematosus). The present compounds can be used in treating asthma or as an adjunct to minimize toxicity with cytokine therapy in the treatment of cancers. The present compounds can be employed in the treatment of all diseases currently treatable through steroid therapy. The present compounds may be employed for the treatment of these and other disorders alone or with other immunosuppressive or antiinflammatory agents. In accordance with the invention, a compound of the formula I can be administered prior to the onset of inflammation (so as to suppress an anticipated inflammation) or after the initiation of inflammation. When provided prophylactically, the immunosupressive compound(s) are preferably provided in advance of any inflammatory response or symptom (for example, prior to, at, or shortly after the time of an organ or tissue transplant but in advance of any symptoms or organ rejection). The prophylactic administration of a compound of the formula I prevents or attenuates any subsequent inflammatory response (such as, for example, rejection of a transplanted organ or tissue, etc.) Administration of a tricycloundecane compound of the formula I attenuates any actual inflammation (such as, for example, the rejection of a transplanted organ or tissue).

The tricycloundecane compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The tricycloundecane compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol™ 934 polymer, B.F. Goodrich Co., NY). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of the tricycloundecane compound of the present invention can be determined by one of ordinary skill in the art, and includes exemplary dosage amounts for an adult human of from about 1 to 100 (for example, 15) mg/kg of body weight of active compound per day, which can be administered in a single dose or in the form of individual divided doses, such as from 1 to 4 times per day. It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to NHR-associated conditions.

As mentioned above, the tricycloundecane compounds of the present invention can be employed alone or in combination with each other and/or other suitable therapeutic agents useful in the treatment of NHR-associated conditions.

For their preferred anticancer or antiangiogenic use, the tricycloundecane compounds of the present invention can be administered either alone or in combination with other anti-cancer and cytotoxic agents and treatments useful in the treatment of cancer or other proliferative diseases, for example, where the second drug has the same or different mechanism of action than the present compounds of formula I. Examples of classes of anti-cancer and cytotoxic agents useful in combination with the present compounds include but are not limited to: alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5α reductase inhibitors; inhibitors of 17β-hydroxy steroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol®), docetaxel (Taxotere®), and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies. The tricycloundecane compounds of the invention may also be used in conjunction with radiation therapy.

Representative examples of these classes of anti-cancer and cytotoxic agents include but are not limited to mechlorethamine hydrochloride, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, etoposide phosphate, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred member of these classes include, but are not limited to, paclitaxel, cisplatin, carboplatin, doxorubicin, carminomycin, daunorubicin, aminopterin, methotrexate, methopterin, mitomycin, mitomycin C, ecteinascidin 743, or porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine and leurosine.

Examples of anticancer and other cytotoxic agents include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416 (see also U.S. Pat. No. 6,040,321); and prenyl-protein transferase inhibitors as found in WO 97/30992 and WO 98/54966; and agents such as those described generically and specifically in U.S. Pat. No. 6,011,029 (the tricycloundecane compounds of which U.S. patent can be employed together with any NHR modulators (including, but not limited to, those of present invention) such as AR modulators, ER modulators, with LHRH modulators, or with surgical castration, especially in the treatment of cancer).

The tricycloundecane compounds of the present invention can also be formulated or co-administered with other therapeutic agents that are selected for their particular usefulness in administering therapies associated with the aforementioned conditions. For example, the tricycloundecane compounds of the invention may be formulated with agents to prevent nausea, hypersensitivity and gastric irritation, such as antiemetics, and $H_1$ and $H_2$ antihistaminics.

As it pertains to the treatment of cancer, the tricycloundecane compounds of this invention are most preferably used alone or in combination with anti-cancer treatments such as radiation therapy and/or with cytostatic and/or cytotoxic agents, such as, but not limited to, DNA interactive agents, such as cisplatin or doxorubicin; inhibitors of farnesyl protein transferase, such as those described in U.S. Pat. No. 6,011,029; topoisomerase II inhibitors, such as etoposide; topoisomerase I inhibitors, such as CPT-11 or topotecan; tubulin stabilizing agents, such as paclitaxel, docetaxel, other taxanes, or epothilones; hormonal agents, such as tamoxifen; thymidilate synthase inhibitors, such as 5-fluorouracil; antimetabolites, such as methoxtrexate; antiangiogenic agents, such as angiostatin, ZD6474, ZD6126 and comberstatin A2; kinase inhibitors, such as her2 specific antibodies, Iressa and CDK inhibitors; histone deacetylase inhibitors, such as CI-994 and MS-27-275. Such compounds may also be combined with agents which suppress the production of circulating testosterone such as LHRH agonists, antagonists, or with surgical castration.

For example, known therapies for advanced metastatic prostate cancer include "complete androgen ablation therapy" wherein tumor growth is inhibited by controlling the supply of androgen to the prostate tissues via chemical castration (castration serves to inhibit the production of circulating testosterone (T) and dihydrotestosterone (DHT)) followed by the administration of androgen receptor (AR) antagonists (which inhibit the function T/DHT derived from the conversion of circulating androgen precursors to T/DHT by the prostate tissue). The tricycloundecane compounds of the present invention can be employed as AR antagonists in complete ablation therapy, alone or in combination with other AR antagonists such as Flutamide, Casodex, Nilutamide, or Cyproterone acetate.

The tricycloundecane compounds of the present invention may be employed adjuvant to surgery.

Another application of the present compounds is in combination with antibody therapy such as but not limited to antibody therapy against PSCA. An additional application is in concert with vaccine/immune modulating agents for the treatment of cancer.

The above other therapeutic agents, when employed in combination with the tricycloundecane compounds of the present invention, can be used, for example, in those amounts indicated in the Physicians' Desk Reference (PDR) or as otherwise determined by one of ordinary skill in the art.

In general, the tricycloundecane compounds of the present invention, such as particular compounds disclosed in the following examples, have been tested in one or more of the assays described below and have shown activity as modulators of nuclear hormone receptors.

Transactivation Assays

AR Specific Assay:

The tricycloundecane compounds of the present invention are tested in transactivation assays of a transfected reporter construct and using the endogenous androgen receptor of the host cells. The transactivation assay provides a method for identifying functional agonists and partial agonists that mimic, or antagonists that inhibit, the effect of native hormones, in this case, dihydrotestosterone (DHT). This assay can be used to predict in vivo activity as there is a good correlation in both series of data. See, e.g. T. Berger et al., *J. Steroid Biochem. Molec. Biol.* 773 (1992), the disclosure of which is herein incorporated by reference.

For the transactivation assay, a reporter plasmid is introduced by transfection (a procedure to induce cells to take foreign genes) into the respective cells. This reporter plasmid, comprising the cDNA for a reporter protein, such as secreted alkaline phosphatase (SEAP), is controlled by prostate specific antigen (PSA) upstream sequences containing androgen response elements (AREs). This reporter plasmid functions as a reporter for the transcription-modulating activity of the AR. Thus, the reporter acts as a surrogate for the products (mRNA then protein) normally expressed by a gene under control of the AR and its native hormone. In order to detect antagonists, the transactivation assay is carried out in the presence of constant concentration of the natural AR hormone (DHT) known to induce a defined reporter signal. Increasing concentrations of a suspected antagonist will decrease the reporter signal (e.g., SEAP production). On the other hand, exposing the transfected cells to increasing concentrations of a suspected agonist will increase the production of the reporter signal.

For this assay, LNCaP and MDA 453 cells are obtained from the American Type Culture Collection (Rockville, Md.), and maintained in RPMI 1640 or DMEM medium supplemented with 10% fetal bovine serum (FBS; Gibco) respectively. The respective cells are transiently transfected by electroporation according to the optimized procedure described by Heiser, 130 Methods Mol. Biol., 117 (2000), with the pSEAP2/PSA540/Enhancer reporter plasmid. The reporter plasmid, is constructed as follows: commercial human placental genomic DNA is used to generate by Polymerase Cycle Reaction (PCR) a fragment containing the BglII site (position 5284) and the Hind III site at position 5831 of the human prostate specific antigen promoter (Accession # U37672), Schuur, et al., *J. Biol. Chem.*, 271 (12): 7043-51 (1996). This fragment is subcloned into the pSEAP2/basic (Clontech) previously digested with BglII and HindIII to generate the pSEAP2/PSA540 construct. Then a fragment bearing the fragment of human PSA upstream sequence between positions −5322 and −3873 is amplified by PCR from human placental genomic DNA. A XhoI and a BglII sites are introduced with the primers. The resulting fragment is subcloned into pSEAP2/PSA540 digested with XhoI and BglII respectively, to generate the pSEAP2/PSA540/Enhancer construct. LNCaP and MDA 453 cells are collected in media containing 10% charcoal stripped FBS. Each cell suspension is distributed into two Gene Pulser Cuvetts (Bio-Rad) which then receive 8 μg of the reporter construct, and is electoporated using a Bio-Rad Gene Pulser at 210 volts and 960 μFaraday. Following the transfections, the cells are washed and incubated with media containing charcoal stripped fetal bovine serum in the absence (blank) or presence (control) of 1 nM dihydrotestosterone (DHT; Sigma Chemical) and in the presence or absence of the standard anti-androgen bicalutamide or compounds of the present invention in concentrations ranging from $10^{-10}$ to $10^{-5}$ M (sample). Duplicates are used for each sample. The tricycloundecane compound dilutions are performed on a Biomek 2000 laboratory workstation.

After 48 hours, a fraction of the supernatant is assayed for SEAP activity using the Phospha-Light Chemiluminescent Reporter Gene Assay System (Tropix, Inc). Viability of the remaining cells is determined using the CellTiter 96 Aqueous Non-Radioactive Cell Proliferation Assay (MTS Assay, Promega). Briefly, a mix of a tetrazolium compound (3-(4,5-dimethylthiazol-2-yl)-5-(3-carboxymethoxyphenyl)-2-(4-sulfophenyl)-2H-tetrazolium, inner salt; MTS) and an electron coupling reagent (phenazine methosulfate; PMS) are added to the cells. MTS (Owen's reagent) is bioreduced by cells into a formazan that is soluble in tissue culture medium, and therefore its absorbance at 490 nm can be measured directly from 96 well assay plates without additional processing. The quantity of formazan product as measured by the amount of 490 nm absorbance is directly proportional to the number of living cells in culture. For each replicate the SEAP reading is normalized by the Abs490 value derived from the MTS assay. For the antagonist mode, the % Inhibition is calculated as:

% Inhibition=100×(1−[(average control−average blank)/(average sample−average blank)])

Data is plotted and the concentration of the tricycloundecane compound that inhibited 50% of the normalized SEAP is quantified ($IC_{50}$).

For the agonist mode, % Control is referred as the effect of the tested compound compared to the maximal effect observed with the natural hormone, in this case DHT, and is calculated as:

% Control=100×(average sample−average blank)/(average control−average blank)

Data is plotted and the concentration of the tricycloundecane compound that activates to levels 50% of the normalized SEAP for the control is quantified ($EC_{50}$).

GR Specificity Assay:

The reporter plasmid utilized is comprised of the cDNA for the reporter SEAP protein, as described for the AR specific transactivation assay. Expression of the reporter SEAP protein is controlled by the mouse mammary tumor virus long terminal repeat (MMTV LTR) sequences that contains three hormone response elements (HREs) that can be regulated by both GR and PR see, e.g. G. Chalepakis et al., *Cell,* 53(3), 371 (1988). This plasmid is transfected into A549 cells, which expresses endogenous GR, to obtain a GR specific transactivation assay. A549 cells are obtained from the American Type Culture Collection (Rockville, Md.), and maintained in RPMI 1640 supplemented with 10% fetal bovine serum (FBS; Gibco). Determination of the GR specific antagonist activity of the tricycloundecane compounds of the present invention is identical to that described for the AR specific transactivation assay, except that the DHT is replaced with 5 nM dexamethasone (Sigma Chemicals), a specific agonist for GR. Determination of the GR specific agonist activity of the tricycloundecane compounds of the present invention is performed as described for the AR transactivation assay, wherein one measures the activation of the GR specific reporter system by the addition of a test compound, in the absence of a known GR specific agonists ligand.

PR Specific Assay:

The reporter plasmid utilized is comprised of the cDNA for the reporter SEAP protein, as described for the AR specific transactivation assay. Expression of the reporter SEAP protein is controlled by the mouse mammary tumor virus long terminal repeat (MMTV LTR) sequences that contains three hormone response elements (HREs) that can be regulated by both GR and PR. This plasmid is transfected into T47D, which expresses endogenous PR, to obtain a PR specific transactivation assay. T47D cells are obtained from the American Type Culture Collection (Rockville, Md.), and maintained in DMEM medium supplemented with 10% fetal bovine serum (FBS; Gibco). Determination of the PR specific antagonist activity of the tricycloundecane compounds of the present invention is identical to that described for the AR specific transactivation assay, except that the DHT is replaced with 1 nM Promegastone (NEN), a specific agonist for PR. Determination of the PR specific agonist activity of the tricycloundecane compounds of the present invention is performed as described for the AR transactivation assay, wherein one measures the activation of the PR specific reporter system by the addition of a test compound, in the absence of a known PR specific agonists ligand.

AR Binding Assay:

For the whole cell binding assay, human LNCaP cells (T877A mutant AR) or MDA 453 (wild type AR) in 96-well microtiter plates containing RPMI 1640 or DMEM supplemented with 10% charcoal stripped CA-FBS (Cocaleco Biologicals) respectively, are incubated at 37° C. to remove any endogenous ligand that might be complexed with the receptor in the cells. After 48 hours, either a saturation analysis to determine the $K_d$ for tritiated dihydrotestosterone, [$^3$H]-DHT, or a competitive binding assay to evaluate the ability of test compounds to compete with [$^3$H]-DHT is performed. For the saturation analysis, media (RPMI 1640 or DMEM−0.2% CA-FBS) containing [$^3$H]-DHT (in concentrations ranging from 0.1 nM to 16 nM) in the absence (total binding) or presence (non-specific binding) of a 500-fold molar excess of unlabeled DHT are added to the cells. After 4 hours at 37° C., an aliquot of the total binding media at each concentration of [$^3$H]-DHT is removed to estimate the amount of free [$^3$H]-DHT. The remaining media is removed, cells are washed three times with PBS and harvested onto UniFilter GF/B plates (Packard), Microscint (Packard) is added and plates counted in a Top-Counter (Packard) to evaluate the amount of bound [$^3$H]-DHT.

For the saturation analysis, the difference between the total binding and the non-specific binding, is defined as specific binding. The specific binding is evaluated by Scatchard analysis to determine the $K_d$ for [$^3$H]-DHT. See e.g. D. Rodbard, *Mathematics and Statistics of Ligand Assays: An Illustrated Guide*: In: J. Langon and J. J. Clapp, eds., Ligand Assay, Masson Publishing U.S.A., Inc., New York, pp. 45-99, (1981), the disclosure of which is herein incorporated by reference.

For the competition studies, media containing 1 nM [$^3$H]-DHT and compounds of the invention ("test compounds") in concentrations ranging from $10^{-10}$ to $10^{-5}$ M are added to the cells. Two replicates are used for each sample. After 4 hours at 37° C., cells are washed, harvested, and counted as described above. The data is plotted as the amount of [$^3$H]-DHT (% of control in the absence of test compound) remaining over the range of the dose response curve for a given compound. The concentration of test compound that inhibited 50% of the amount of [$^3$H]-DHT bound in the absence of competing ligand is quantified ($IC_{50}$) after log-logit transformation. The $K_I$ values are determined by application of the Cheng-Prusoff equation to the $IC_{50}$ values, where:

$$K_1 = \frac{IC_{50}}{(1 + (^3\text{H-DHT})/K_d \text{ for }^3\text{H-DHT})}.$$

After correcting for non-specific binding, $IC_{50}$ values are determined. The $IC_{50}$ is defined as the concentration of competing ligand needed to reduce specific binding by 50%. The $K_d$ values for [$^3$H]-DHT for MDA 453 and LNCaP are 0.7 and 0.2 nM respectively.

Human Prostate Cell Proliferation Assay:

Compounds of the present invention are tested ("test compounds") on the proliferation of human prostate cancer cell lines. For that, MDA PCa2b cells, a cell line derived from the metastasis of a patient that failed castration, Navone et al., *Clin. Cancer Res.*, 3, 2493-500 (1997), are incubated with or without the test compounds for 72 hours and the amount of [$^3$H]-thymidine incorporated into DNA is quantified as a way to assess number of cells and therefore proliferation. The MDA PCa2b cell line is maintained in BRFF-HPC1 media (Biological Research Faculty & Facility Inc., MD) supplemented with 10% FBS. For the assay, cells are plated in Biocoated 96-well microplates and incubated at 37° C. in 10% FBS (charcoal-stripped)/BRFF-BMZERO (without androgens). After 24 hours, the cells are treated in the absence (blank) or presence of 1 nM DHT (control) or with test compounds (sample) of the present invention in concentrations ranging from $10^{-10}$ to $10^{-5}$ M. Duplicates are used for each sample. The compound dilutions are performed on a Biomek 2000 laboratory work station. Seventy two hours later 0.44 uCi. of [$^3$H]-Thymidine (Amersham) is added per well and incubated for another 24 h followed by tripsinization, harvesting of the cells onto GF/B filters. Micro-scint PS are added to the filters before counting them on a Beckman TopCount.

The % Inhibition was calculated as:

% Inhibition=100×(1−[(average$_{control}$−average$_{blank}$)/(average$_{sample}$−average$_{blank}$)]).

Data is plotted and the concentration of compound that inhibited 50% of the [$^3$H]-Thymidine incorporation is quantified ($IC_{50}$).

C2C12 Mouse Myoblast Transactivation Assay:

Two functional transactivation assays are developed to assess the efficacy of androgen agonists in a muscle cell background using a luciferase reporter. The first assay (ARTA Stable 1) uses a cell line, Stable 1 (clone #72), which stably expresses the full length rat androgen receptor but requires the transient transfection of an enhancer/reporter. This cell line is derived from C2C12 mouse moyoblast cells. The second assay (ARTA Stable 2) uses a cell line, Stable 2 (clone #133), derived from Stable 1 which stably expresses both rAR and the enhancer/luciferase reporter.

The enhancer/reporter construct used in this system is pGL3/2XDR-1/luciferase. 2XDR-1 was reported to be an AR specific response element in CV-1 cells, Brown et. al. *The Journal of Biological Chemistry* 272, 8227-8235, (1997). It was developed by random mutagenesis of an AR/GR consensus enhancer sequence.

ARTA Stable 1:

1. Stable 1 cells are plated in 96 well format at 6,000 cells/well in high glucose DMEM without phenol red (Gibco BRL, Cat. No.: 21063-029) containing 10% charcoal and dextran treated FBS (HyClone Cat. No.: SH30068.02), 50 mM HEPES Buffer (Gibco BRL, Cat. No.: 15630-080), 1× MEM Na Pyruvate (Gibco BRL, Cat. No.: 11360-070), 0.5× Antibiotic-Antimycotic, and 800 μg/ml Geneticin (Gibco BRL, Cat. No.: 10131-035).

2. 48 hours later, the cells are transfected with pGL3/2XDR-1/luciferase using LipofectAMINE Plus™ Reagent (Gibco BRL, Cat. No.: 10964-013). Specifically, 5 ng/well pGL3/2XDR-1/luciferase DNA and 50 ng/well Salmon Sperm DNA (as carrier) are diluted with 5 μl/well Opti-MEMem media (Gibco BRL, Cat. No.: 31985-070). To this, 0.5 μl/well Plus reagent is added. This mixture is incubated for 15 minutes at room temperature. In a separate vessel, 0.385 μl/well LipofectAMINE reagent is diluted with 5 μl/well Opti-MEM. The DNA mixture is then combined with the LipofectAMINE mixture and incubated for an additional 15 minutes at room temperature. During this time, the media from the cells is removed and replaced with 60 μl/well of Opti-MEM. To this is added 10 μl/well of the DNA/LipofectAMINE transfection mixture. The cells are incubated for 4 hours.

3. The transfection mixture is removed from the cells and replaced with 90 μl of media as in #1 above.

4. 10 μl/well of appropriate drug dilution is placed in each well. 24 hours later, the Steady-Glo™ Luciferase Assay System is used to detect activity according to the manufacturer's instructions (Promega, Cat. No.: E2520).

ARTA Stable 2:

1. Stable 2 cells are plated in 96 well format at 6,000 cells/well in high glucose DMEM without phenol red (Gibco BRL, Cat. No.: 21063-029) containing 10% charcoal and dextran treated FBS (HyClone Cat. No.: SH30068.02), 50 mM HEPES Buffer (Gibco BRL, Cat. No.: 15630-080), 1× MEM Na Pyruvate (Gibco BRL, Cat. No.: 11360-070), 0.5× Antibiotic-Antimycotic, 800 μg/ml Geneticin (Gibco BRL, Cat. No.: 10131-035) and 800 μg/ml Hygromycin β (Gibco BRL, Cat. No.: 10687-010).

2. 48 hours later, the media on the cells is removed and replaced with 90 μl fresh. 10 μl/well of appropriate drug dilution is placed in each well.

3. 24 hours later, the Steady-Glo™ Luciferase Assay System is used to detect activity according to the manufacturer's instructions (Promega, Cat. No.: E2520).

Proliferation Assays

Murine Breast Cell Proliferation Assay:

The ability of the tricycloundecane compounds of the present invention ("test compounds") to modulate the function of the AR is determined by testing said compounds in a proliferation assay using the androgen responsive murine breast cell line derived from the Shionogi tumor, Hiraoka et al, *Cancer Res.*, 47, 6560-6564 (1987). Stable AR dependent clones of the parental Shionogi line are established by passing tumor fragments under the general procedures originally described in Tetuo, et. al., *Cancer Res.*, 25, 1168-1175 (1965). From the above procedure, one stable line, SC114, is isolated, characterized, and utilized for the testing of example compounds. SC114 cells are incubated with or without the test compounds for 72 hours and the amount of [$^3$H]-thymidine incorporated into DNA is quantified as a surrogate endpoint to assess the number of cells and therefore the proliferation rate as described in Suzuki et. al., *J. Steroid Biochem. Mol. Biol.* 37, 559-567 (1990). The SC114 cell line is maintained in MEM containing $10^{-8}$ M testosterone and 2% DCC-treated FCS. For the assay, cells are plated in 96-well microplates in the maintenance media and incubated at 37° C. On the following day, the medium is changed to serum free medium [Ham's F-12:MEM (1:1, v/v) containing 0.1% BSA] with (antagonist mode) or without (agonist mode) $10^{-8}$ M testosterone and the test compounds of the present invention in concentrations ranging from $10^{-10}$ to $10^{-5}$ M. Duplicates are used for each sample. The tricycloundecane compound dilutions are performed on a Biomek 2000 laboratory work station. Seventy two hours later 0.44 µCi of [$^3$H]-Thymidine (Amersham) is added per well and incubated for another 2 hr followed by tripsinization, and harvesting of the cells onto GF/B filters. Micro-scint PS is added to the filters before counting them on a Beckman TopCount. For the antagonist mode, the % Inhibition is calculated as:

% Inhibition=100×(1−[(average$_{sample}$−average$_{blank}$)/(average$_{control}$−average$_{blank}$)])

Data is plotted and the concentration of compound that inhibited 50% of the [$^3$H]-Thymidine incorporation is quantified (IC$_{50}$).

For the agonist mode % Control is referred as the effect of the tested compound compared to the maximal effect observed with the natural hormone, in this case DHT, and is calculated as:

% Control=100×(average$_{sample}$−average$_{blank}$)/(average$_{control}$−average$_{blank}$)

Data is plotted and the concentration of compound that inhibited 50% of the [$^3$H]-Thymidine incorporation is quantified (EC$_{50}$).

In Vitro Assay to Measure GR Induced AP-1 Transrepression:

The AP-1 assay is a cell based luciferase reporter assay. A549 cells, which contain endogenous glucocorticoid receptor, are stably transfected with an AP-1 DNA binding site attached to the luciferase gene. Cells are then grown in RPMI+10% fetal calf serum (charcoal-treated)+Penicillin/Streptomycin with 0.5 mg/ml geneticin. Cells are plated the day before the assay at approximately 40000 cells/well. On assay day, the media is removed by aspiration and 20 µl assay buffer (RPMI without phenol red+10% FCS (charcoal-treated)+Pen/Strep) is added to each well. At this point either 20 µl assay buffer (control experiments), the tricycloundecane compounds of the present invention ("test compounds") (dissolved in DMSO and added at varying concentrations), or dexamethasome (100 nM in DMSO, positive control) are added to each well. The plates are then pre-incubated for 15 minutes at 37° C., followed by stimulation of the cells with 10 ng/ml PMA. The plates are then incubated for 7 hrs at 37° C. after which 40 µl luciferase substrate reagent is added to each well. Activity is measured by analysis in a luminometer as compared to control experiments treated with buffer or dexamethasome. Activity is designated as % inhibition of the reporter system as compared to the buffer control with 10 ng/ml PMA alone. The control, dexamethasone, at a concentration of $\leq 10$ µM typically suppresses activity by 65%. Test compounds that demonstrate an inhibition of PMA induction of 50% or greater at a concentration of test compound of $\leq 10$ µM are deemed active.

Wet Prostate Weight Assay AR Antagonist Assay:

The activity of compounds of the present invention as AR antagonists is investigated in an immature male rat model, a standard, recognized test of antiandrogen activity of a given compound, as described in L. G. Hershberger et al., *Proc. Soc. Expt. Biol. Med.*, 83, 175 (1953); P. C. Walsh and R. F. Gittes, "Inhibition of extratesticular stimuli to prostate growth in the castrated rat by antiandrogens", *Endocrinology*, 86, 624 (1970); and B. J. Furr et al., "ICI 176,334: A novel non-steroid, peripherally selective antiandrogen", *J. Endocrinol.*, 113, R7-9 (1987), the disclosures of which are herein incorporated by reference.

The basis of this assay is the fact that male sexual accessory organs, such as the prostate and seminal vesicles, play an important role in reproductive function. These glands are stimulated to grow and are maintained in size and secretory function by the continued presence of serum testosterone (T), which is the major serum androgen (>95%) produced by the Leydig cells in the testis under the control of the pituitary luteinizing hormone (LH) and follicle stimulating hormone (FSH). Testosterone is converted to the more active form, dihydrotestosterone, (DHT), within the prostate by 5α-reductase. Adrenal androgens also contribute about 20% of total DHT in the rat prostate, compared to 40% of that in 65-year-old men. F. Labrie et al. *Clin. Invest. Med.*, 16, 475-492 (1993). However, this is not a major pathway, since in both animals and humans, castration leads to almost complete involution of the prostate and seminal vesicles without concomitant adrenalectomy. Therefore, under normal conditions, the adrenals do not support significant growth of prostate tissues. M. C. Luke and D. S. Coffey, "*The Physiology of Reproduction*" ed. by E. Knobil and J. D. Neill, 1, 1435-1487 (1994). Since the male sex organs are the tissues most responsive to modulation of the androgen activity, this model is used to determine the androgen dependent growth of the sex accessory organs in immature castrated rats.

Male immature rats (19-20 days old Sprague-Dawley, Harlan Sprague-Dawley) are castrated under metofane anesthesia. Five days after surgery these castrated rats (60-70 g, 23-25 day-old) are dosed for 3 days. Animals are dosed subcutaneously (s.c.) 1 mg/kg with Testosterone Proprionate (TP) in arachis oil vehicle and anti-androgen test compounds (compounds of the present invention) are dosed orally by gavage (p.o.) in dissolved/suspensions of 80% PEG 400 and 20% Tween 80 surfactant(PEGTW). Animals are dosed (v/w) at 0.5 ml of vehicle /100 g body weight. Experimental groups are as follows:

1. Control vehicle
2. Testosterone Propionate (TP) (3 mg/rat/day, subcutaneous)
3. TP plus Casodex (administered p.o. in PEGTW, QD), a recognized antiandrogen, as a reference compound.
4. To demonstrate antagonist activity, a compound of the present invention ("test compound") is administered (p.o. in PEGTW, QD) with TP (s.c. as administered in group 2) in a range of doses.
5. To demonstrate agonist activity a compound of the present invention ("test compound") is administered alone (p.o. in PEGTW, QD) in a range of doses.

At the end of the 3-day treatment, the animals are sacrificed, and the ventral prostate weighed. To compare data from different experiments, the sexual organs weights are first standardized as mg per 100 g of body weight, and the increase in organ weight induced by TP was considered as the maximum increase (100%). ANOVA followed by one-tailed Student or Fischer's exact test is used for statistical analysis.

The gain and loss of sexual organ weight reflect the changes of the cell number (DNA content) and cell mass (protein content), depending upon the serum androgen concentration. See Y. Okuda et al., *J. Urol.*, 145, 188-191 (1991), the disclosure of which is herein incorporated by reference. Therefore, measurement of organ wet weight is sufficient to indicate the bioactivity of androgens and androgen antagonist. In immature castrated rats, replacement of exogenous androgens increases seminal vesicles (SV) and the ventral prostate (VP) in a dose dependent manner.

The maximum increase in organ weight is 4 to 5-fold when dosing 3 mg/rat/day of testosterone (T) or 1 mg/rat/day of testosterone propionate (TP) for 3 days. The $EC_{50}$ of T and TP are about 1 mg and 0.03 mg, respectively. The increase in the weight of the VP and SV also correlates with the increase in the serum T and DHT concentration. Although administration of T shows 5-times higher serum concentrations of T and DHT at 2 hours after subcutaneous injection than that of TP, thereafter, these high levels decline very rapidly. In contrast, the serum concentrations of T and DHT in TP-treated animals are fairly consistent during the 24 hours, and therefore, TP showed about 10-30-fold higher potency than free T.

In this immature castrated rat model, a known AR antagonist (Casodex) is also administered simultaneously with 0.1 mg of TP ($ED_{80}$), inhibiting the testosterone-mediated increase in the weights of the VP and SV in a dose dependent manner. The antagonist effects are similar when dosing orally or subcutaneously. Compounds of the invention also exhibit AR antagonist activity by suppressing the testosterone-mediated increase in the weights of VP and SV.

Levator Ani & Wet Prostate Weight Assay AR Agonist Assay:

The activity of compounds of the present invention as AR agonists is investigated in an immature male rat model, a recognized test of anabolic effects in muscle and sustaining effects in sex organs for a given compound, as described in L. G. Hershberger et al., *Proc. Soc. Expt. Biol. Med.*, 83, 175 (1953); B. L. Beyler et al, "Methods for evaluating anabolic and catabolic agents in laboratory animals", *J. Amer. Med. Women's Ass.*, 23, 708 (1968); H. Fukuda et al., "Investigations of the levator ani muscle as an anabolic steroid assay", *Nago Dai. Yak. Ken. Nem.* 14, 84 (1966) the disclosures of which are herein incorporated by reference.

The basis of this assay lies in the well-defined action of androgenic agents on the maintenance and growth of muscle tissues and sexual accessory organs in animals and man. Androgenic steroids, such as testosterone (T), have been well characterized for their ability to maintain muscle mass. Treatment of animals or humans after castrations with an exogenous source of T resulted in a reversal of muscular atrophy. The effects of T on muscular atrophy in the rat levator ani muscle have been characterized, M. Masuoka et al., "Constant cell population in normal, testosterone deprived and testosterone stimulated levator ani muscles" *Am. J. Anat.* 119, 263 (1966); Z. Gori et al., "Testosterone hypertrophy of levator ani muscle of castrated rats. I. Quantitative data" *Boll. —Soc. Ital. Biol. Sper.* 42, 1596 (1966); Z. Gori et al., "Testosterone hypertrophy of levator ani muscle of castrated rats. II. Electron-microscopic observations" *Boll. —Soc. Ital. Biol. Sper.* 42, 1600 (1966); A. Boris et al., *Steroids* 15, 61 (1970). As described above, the effects of androgens on maintenance of male sexual accessory organs, such as the prostate and seminal vesicles, was described. Castration results in rapid involution and atrophy of the prostate and seminal vesicles. This effect can be reversed by exogenous addition of androgens. Since both the levator ani muscle and the male sex organs are the tissues most responsive to the effects of androgenic agents, this model is used to determine the androgen dependent reversal of atrophy in the levator ani muscle and the sex accessory organs in immature castrated rats. Sexually mature rats (200-250 g, 6-8 weeks-old, Sprague-Dawley, Harlan) are acquired castrated from the vendor (Taconic). The rats are divided into groups and treated daily for 7 to 14 days with one of the following:

1. Control vehicle
2. Testosterone Propionate (TP) (3 mg/rat/day, subcutaneous)
3. TP plus Casodex (administered p.o. in PEGTW, QD), a recognized antiandrogen, as a reference compound.
4. To demonstrate antagonist activity, a compound of the present invention ("test compound") is administered (p.o. in PEGTW, QD) with TP (s.c. as administered in group 2) in a range of doses.
5. To demonstrate agonist activity, a compound of the present invention ("test compound") is administered alone (p.o. in PEGTW, QD) in a range of doses.

At the end of the 7-14-day treatment, the animals are sacrificed by carbon dioxide, and the levator ani, seminal vesicle and ventral prostate weighed. To compare data from different experiments, the levator ani muscle and sexual organ weights are first standardized as mg per 100 g of body weight, and the increase in organ weight induced by TP is considered as the maximum increase (100%). Super-anova (one factor) is used for statistical analysis.

The gain and loss of sexual organ weight reflect the changes of the cell number (DNA content) and cell mass (protein content), depending upon the serum androgen concentration. See Y. Okuda et al., *J. Urol.*, 145, 188-191 (1991), the disclosure of which is herein incorporated by reference. Therefore, measurement of organ wet weight is sufficient to indicate the bioactivity of androgens and androgen antagonist. In immature castrated rats, replacement of exogenous androgens increase levator ani, seminal vesicles (SV) and prostate in a dose dependent manner.

The maximum increase in organ weight is 4 to 5-fold when dosing 3 mg/rat/day of testosterone (T) or 1 mg/rat/day of testosterone propionate (TP) for 3 days. The $EC_{50}$ of T and TP are about 1 mg and 0.03 mg, respectively. The increase in the weight of the VP and SV also correlates with the increase in the serum T and DHT concentration. Although administration of T shows 5-times higher serum concentrations of T and DHT at 2 hours after subcutaneous injection than that of TP, thereafter, these high levels decline very rapidly. In contrast, the serum concentrations of T and DHT in TP-treated animals are fairly consistent during the 24 hours, and therefore, TP shows about 10-30-fold higher potency than free T.

MDA PCa2b Human Prostate Zenograft Assay:

In Vivo Antitumor Testing: MDA-PCa-2b human prostate tumors are maintained in Balb/c nu/nu nude mice. Tumors are propagated as subcutaneous transplants in adult male nude mice (4-6 weeks old) using tumor fragments obtained from donor mice. Tumor passage occurs every 5-6 weeks.

For antitumor efficacy trial, the required number of animals needed to detect a meaningful response are pooled at the start of the experiment and each is given a subcutaneous implant of a tumor fragment (~50 mg) with a 13-gauge trocar. Tumors are allowed to grow to approximately 100-200 mg (tumors outside the range were excluded) and animals are evenly distributed to various treatment and control groups. Treatment of each animal is based on individual body weight. Treated animals are checked daily for treatment related toxicity/mortality. Each group of animals is weighed before the initiation of treatment ($Wt_1$) and then again following the last treatment dose ($Wt_2$). The difference in body weight ($Wt_2-Wt_1$) provides a measure of treatment-related toxicity.

Tumor response is determined by measurement of tumors with a caliper twice a week, until the tumors reach a predetermined "target" size of 0.5 gm. Tumor weights (mg) are estimated from the formula: Tumor weight=(length×width$^2$)÷2.

Tumor response end-point is expressed in terms of tumor growth inhibition (% T/C), defined as the ratio of median tumor weights of the treated tumors (T) to that of the control group (C).

To estimate tumor cell kill, the tumor volume doubling time is first calculated with the formula:

$TVDT$=(Median time (days) for control tumors to reach target size)−(Median time (days) for control tumors to reach half the target sizes) And,
Log cell kill=$(T−C)÷(3.32×TVDT)$.

Statistical evaluations of data are performed using Gehan's generalized Wilcoxon test.

Dunning Prostate Tumor:

Dunning R3327H prostate tumor is a spontaneously derived, well differentiated androgen responsive adenocarcinoma of the prostate (Smolev J K, Heston W D, Scott W W, and Coffey D S, *Cancer Treat Rep.* 61, 273-287 (1977)). The growth of the R3327H subline has been selected for its highly androgen-dependent and reproducible growth in intact male rats. Therefore, this model and other sublines of this tumor have been widely used to evaluate in vivo antitumor activities of antiandrogens such as flutamide and bacilutamide/Casodex (Maucher A., and von Angerer, *J. Cancer Res. Clin. Oncol.*, 119, 669-674 (1993), Furr B. J. A. Euro. URL. 18 (suppl. 3), 2-9 (1990), Shain S. A. and Huot R I. *J. Steroid Biochem.* 31, 711-718 (1988)).

At the beginning of the study, the Dunning tumor pieces (about 4×4 mm) are transplanted subcutaneously to the flank of mature male Copenhagen rats (6-7 weeks old, Harlan-Sprague Dawley, Indianapolis, Md.). About 6 weeks after the implantation, the animals with tumors of measurable size (about 80-120 mm$^2$) are randomized into treatment groups (8-10 rats/group) and the treatments are initiated. One group of the rats is castrated to serve as the negative control of tumor growth. Animals are treated daily with compounds of the current invention, standard antiandrogens such as bacilutamide or vehicle (control) for an average of 10 to 14 weeks. Test compounds are dissolved in a vehicle of (2.5 ml/kg of body weight) 10% polyethylene glycol and 0.05% Tween-80 surfactant in 1% carboxymethyl cellulose, PEG/CMC, (Sigma, St Louis, Mo.). Typical therapeutic experiments would include three groups of three escalating doses for each standard or test compound (in a range of 300-3 mg/kg).

Tumors in the vehicle (control) group reach a size of 1500 to 2500 mm$^3$, whereas the castrated animal group typically shows tumor stasis over the 14 weeks of observation. Animals treated orally with 20 mg/kg of bicalutamide or flutamide would be expected to show a 40% reduction in tumor volumes compared to control after 14 weeks of treatment. The size of tumors are measured weekly by vernier caliper (Froboz, Switzerland), taking perpendicular measurements of length and width. Tumor volumes are measured in mm using the formula: Length×Width×Height=Volume. Statistical differences between treatment groups and control are evaluated using multiple ANOVA analysis followed by one tail non-parametric Student t test.

Mature Rat Prostate Weight Assay:

The activity of compounds of the present invention are investigated in a mature male rat model, which is a variation of the Levator ani & wet prostate weight assay described above. The above in vivo assays are recognized assays for determining the anabolic effects in muscle and sustaining effects in sex organs for a given compound, as described in L. G. Hershberger et al., 83 *Proc. Soc. Expt. Biol. Med.*, 175 (1953); B. L. Beyler et al, "Methods for evaluating anabolic and catabolic agents in laboratory animals", 23 *J. Amer. Med. Women's Ass.*, 708 (1968); H. Fukuda et al., "Investigations of the levator ani muscle as an anabolic steroid assay", 14 *Nago Dai. Yak. Ken. Nem.* 84 (1966) the disclosures of which are herein incorporated by reference. The basis of this assay lies in the well-defined action of androgenic agents on the maintenance and growth of muscle tissues and sexual accessory organs in animals and man.

The male sexual accessory organs, such as the prostate and seminal vesicles, play an important role in reproductive function. These glands are stimulated to grow and are maintained in size and secretory function by the continued presence of serum testosterone (T), which is the major serum androgen (>95%) produced by the Leydig cells in the testis under the control of the pituitary luteinizing hormone (LH) and follicle stimulating hormone (FSH). Testosterone is converted to the more active form, dihydrotestosterone, (DHT), within the prostate by 5α-reductase. Adrenal androgens also contribute about 20% of total DHT in the rat prostate, compared to 40% of that in 65-year-old men. F. Labrie et. al. 16 *Clin. Invest. Med.*, 475-492 (1993). However, this is not a major pathway, since in both animals and humans, castration leads to almost complete involution of the prostate and seminal vesicles without concomitant adrenalectomy. Therefore, under normal conditions, the adrenals do not support significant growth of prostate tissues, M. C. Luke and D. S. Coffey, "The Physiology of Reproduction" ed. By E. Knobil and J. D. Neill, 1, 1435-1487 (1994). Since the male sex organs and the levator ani are the tissues most responsive to modulation of the androgen activity, this model is used to determine the activity of compounds that modulate the androgen receptor pathway in mature rats.

Along with its mitogenic activity on tissues such as prostate, seminal vesicle and muscle, testosterone also serves as a negative regulator for its own biosynthesis. Testosterone production in the Leydig cells of the testis is controlled by the level of circulating LH released from the pituitary gland. LH levels are themselves controlled by the level of LHRH produced in the hypothalamic region. Testosterone levels in the blood serve to inhibit the secretion of LHRH and subsequently reduce levels of LH and ultimately the levels of circulating testosterone levels. By measuring blood levels of LH as they are effected by compounds of the present invention ("test compounds"), it is possible to determine the level of agonist or antagonist activity of said compounds at the hypothalamic axis of this endocrine cycle.

Matched sets of Harlan Sprague-Dawley rats (40-42 days old, 180-220 g), are dosed orally by gavage (p.o.) with the test compounds in dissolved/suspensions of 80% PEG 400 and 20% Tween 20 surfactant (PEGTW) for 14 days. Two control groups, one intact and one castrated are doses orally only with the PEGTW vehicle. Animals are dosed (v/w) at 0.5 ml of vehicle /100 g body weight. Experimental groups are as follows:
1. Intact vehicle (p.o., PEGTW, QD)
2. Control vehicle (p.o., PEGTW, QD)
3. Bicalutamide (Casodex, a recognized antiandrogen, as a reference compound) or a compound of the present invention, p.o. in PEGTW QD. (in a range of doses).

At the end of the 14-day treatment, the animals are sacrificed, and the ventral prostate, the seminal vesicles, and the levator ani are removed surgically and weighed. To compare data from different experiments, the organs weights are first standardized as mg per 100 g of body weight, and expressed as a percentage of the value of the respective organ in the intact group.

Rat luteinizing hormone (rLH) is quantitatively determined with the Biotrak [125 I] kit (Amersham Pharmacia Biotek), following the manufacturer directions. The assay is based on the competition by the LH present in the serum of the binding of [$^{125}$I] rLH to an Amerlex-M bead/antibody suspension. The radioactivity that remains after incubation with the serum and subsequent washes is extrapolated into a standard curve to obtain a reading in ng/ml.

The gain and loss of sexual organ and levator ani weight reflect the changes of the cell number (DNA content) and cell mass (protein content), depending upon the serum androgen concentration, see Y. Okuda et al., *J. Urol.*, 145, 188-191 (1991), the disclosure of which in herein incorporated by reference. Therefore, measurement of organ wet weight is sufficient to indicate the bioactivity of androgens and androgen antagonist. In the mature rats assay, active agonist agents will have no effect or will increase the weight of one or more of the androgen responsive organs (levator ani, prostate, seminal vessicle) and will have no effect or a suppressive effect on LH secretion. Compounds with antagonist activity will decrease the weight of one or more of the androgen responsive organs (levator ani, prostate, seminal vesicle) and will have no effect or a reduced suppressive effect on LH secretion.

CWR22 Human Prostate Zenograft Assay:

In Vivo Antitumor Testing: CWR22 human prostate tumors are maintained in Balb/c nu/nu nude mice. Tumors are propagated as subcutaneous transplants in adult male nude mice (4-6 weeks old) using tumor fragments obtained from donor mice. Tumor passage occurs every 5-6 weeks.

For antitumor efficacy trial, the required number of animals needed to detect a meaningful response are pooled at the start of the experiment and each is given a subcutaneous implant of a tumor fragment (~50 mg) with a 13-gauge trocar. Tumors are allowed to grow to approx. 100-200 mg (tumors outside the range were excluded) and animals are evenly distributed to various treatment and control groups. Treatment of each animal is based on individual body weight. Treated animals are checked daily for treatment related toxicity/mortality. Each group of animals is weighed before the initiation of treatment ($Wt_1$) and then again following the last treatment dose ($Wt_2$). The difference in body weight ($Wt_2$-$Wt_1$) provides a measure of treatment-related toxicity.

Tumor response is determined by measurement of tumors with a caliper twice a week, until the tumors reach a predetermined "target" size of 0.5 gm. Tumor weights (mg) are estimated from the formula: Tumor weight=(length×width$^2$)÷2.

Tumor response end-point is expressed in terms of tumor growth inhibition (% T/C), defined as the ratio of median tumor weights of the treated tumors (T) to that of the control group (C).

To estimate tumor cell kill, the tumor volume doubling time is first calculated with the formula:

$TVDT$=[(Median time (days) for control tumors to reach target size)−(Median time (days) for control tumors to reach half the target size)].

And, Log cell kill=(T−C)÷(3.32×TVDT)

Statistical evaluations of data are performed using Gehan's generalized Wilcoxon test.

The following Examples illustrate embodiments of the present invention, and are not intended to limit the scope of the claims.

Abbreviations

The following abbreviations are used herein:
Ac=acetyl
Et=ethyl
EtOAc=ethyl acetate
h=hour
HPLC=high pressure liquid chromatography
L=liter
LC=liquid chromatography
Me=methyl
min=minute
mL=milliliter
mCPBA=3-chloroperoxybenzoic acid
In°=Indium metal
LiHMDS=lithium bis(trimethylsilyl)amide
MS=molecular sieves
MS(ES)=Electro-Spray Mass Spectrometry
Ph=phenyl
RT=retention time
t-Bu=tert-butyl
TEA=triethylamine
TFA=trifluoroacetic acid
THF=tetrahydrofuran
TLC=thin layer chromatography
TsCl=para-toluenesulfonyl chloride The following HPLC conditions were used throughout the experimental and are referenced in the tables.

Method A:

Five minute HPLC run with a YMC S5 ODS column (4.6×50 mm), eluting with a gradient of 10-90% aqueous methanol over 4 minutes containing 0.2% phosphoric acid, flow rate of 4 mL/min, and monitoring at 220 nm. Retention time reported in minutes.

Method B:

Three minute HPLC run with a Phenomenex Primesphere C18-HC column (4.6×30 mm), eluting with a gradient of 10-90% aqueous methanol over 4 minutes containing 0.1% trifluoroacetic acid, flow rate of 4 mL/min, and monitoring at 220 nm. Retention time reported in minutes.

Method C:

HPLC chromatograms were obtained using a Hypersil C18 BDS column, 250×4.6 mm, 5 µm, a detection wavelength of 254 nm, and a flow rate of 1 mL/min. A linear gradient of 90% of 0.1 % trifluoroacetic acid in water, 10% acetonitrile (start) to 100% acetonitrile over 15 min, then 100% acetonitrile for 5 min was used.

$^1$H NMR spectra were recorded at room temperature on a Bruker 500 MHz spectrometer in CDCl$_3$ unless otherwise stated, and tetramethylsilane was used as an internal standard. Mass spectra were performed on a Varian 1200L Quadrupole LC-MS.

PREPARATION 1

4-(1,7-Dimethyl-3,5-dioxo-10-oxa4-aza-tricyclo[5.2.1.0$^{2,6}$]dec-8-en4-yl)-2-trifluoromethyl-benzonitrile

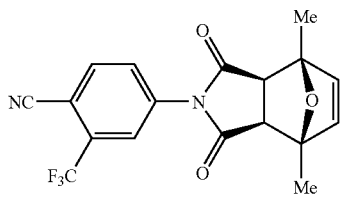

A slurry of 4-(2,5-Dioxo-2,5-dihydro-pyrrol-1-yl)-2-trifluoromethyl-benzonitrile (30 g, 113 mmol) and 2,5-dimethylfuran (70 mL) was stirred at 60° C. for 0.5 h. After toluene (40 mL) was added, the reaction mixture was stirred at 60° C. for 3 h. The mixture was then cooled in ice bath. The solid was collected by filtration and washed with cold toluene (30 mL) to give Preparation 1 as an off white solid (36.8 g, 102 mmol, 90% yield).

EXAMPLE 1

4-[9-(4-Chloro-phenyl)-1,7-dimethyl-3,5-dioxo-11-oxa4,9-diazatricyclo[5.3.1.0$^{2,6}$]undec4-yl]-2-trifluoromethyl-benzonitrile

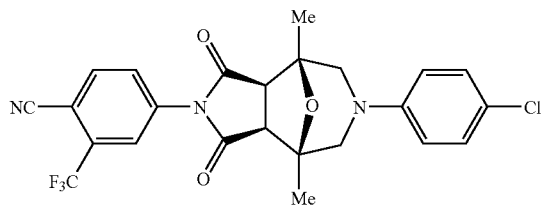

A clear solution of Preparation 1 (1.8 g, 5 mmol) in methanol (25 mL) and methylene chloride (25 mL) was cooled to −78° C. while ozone was bubbled through the reaction mixture. When the reaction mixture turned blue, the flow of ozone was stopped and nitrogen was bubbled through the mixture to get a yellow solution. Next, 3 mL (0.3 mmol) of the solution was reduced with sodium cyanoborohydride (45 mg, 0.72 mmol) at 0° C. for 15 min and then maintained at room temperature for 15 min. After 4-chloroaniline (80 mg, 0.63) and acetic acid (1 mL) were added, the mixture was stirred at room temperature for 1 day and then concentrated. The residue was partitioned between EtOAc and saturated aqueous sodium bicarbonate solution. The organic solution was separated, dried (Na$_2$SO$_4$), and concentrated. The crude product was purified by flash chromatography on silica using gradient elution (0-100% EtOAc in heptane). The product obtained was dissolved in EtOAc and precipitated out with heptane to give Example 1 as a white solid (61 mg, 0.12 mmol, 40% yield). $^1$H NMR (400 MHz) (CD3COCD3) δ 8.24 (d, J=8.3 Hz, 1H), 8.04 (s, 1H), 7.97 (d, J=8.3 Hz, 1H), 7.25 (d, J=9 Hz, 2H), 7.05 (d, J=9 Hz, 2H), 3.74 (d, J=12.1 Hz, 2H), 3.57 (s, 2H), 2.68 (d, J=12.1 Hz, 2H), 1.50 (s, 6H). HPLC: 100% at 3.96 min (retention time) (YMC S5 ODS column 4.6×50 mm, 10-90% aqueous methanol over 4 minutes containing 0.2% phosphoric acid, 4 mL/min, monitoring at 220 nm), HiRes MS (ES): m/z 490.1137 [M+H]$^+$.

The remainder of the ozonolysis reaction solution was concentrated to give a white solid (2.2 g, containing about 4.7 mmol ozonide).

EXAMPLE 2

4-(9-Hydroxy-1,7-dimethyl-3,5-dioxo-11-oxa4,9-diaza-tricyclo[5.3.1.0$^{2,6}$]undec-4-yl)-2-trifluoromethyl-benzonitrile

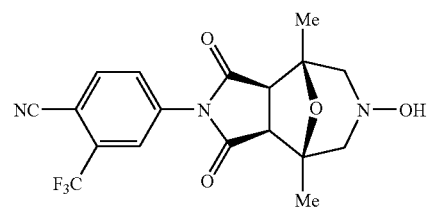

Preparation 1 (28.3 g, 0.078 mol), methanol (566 mL), and 1,2-dichloroethane (425 mL) were added to a nitrogen-purged, dry 3 L three-necked round bottomed flask equipped with a mechanical stirrer and a temperature probe. The solution was stirred vigorously and cooled to −70° C. (a suspension forms at about −45° C.) and the temperature probe was replaced by an ozone inlet. Ozone was then bubbled directly into the suspension at −70° C. for 4 h. After this time, the flow of ozone was ceased and nitrogen was bubbled into the suspension as the reaction warmed to −5° C. (the reaction became a pale yellow solution at −45° C.). Sodium cyanoborohydride (21.6 g, 0.343 mol) was then added portionwise over 5 minutes keeping the reaction temperature below 5° C. with an ice water bath. Once addition was complete, the bath was removed and the solution warmed to room temperature over 0.5 h, then stirred at room temperature for 15 minutes. The reaction was then re-cooled to 0° C. and acetic acid (32 mL), 50% NH$_2$OH in water (19.0 mL, 0.287 mol) and acetic acid (125 mL) were added successively. The reaction was then heated to 60° C. over 0.5 h and kept at 60° C. for 1 h. A second portion of sodium cyanoborohydride (15.7 g, 0.250 mol) was added slowly and the solution heated another hour at 60° C. A third portion of sodium cyanoborohydride (15.7 g, 0.250 mol) was added and the reaction stirred at 60° C. for 0.5 h. The reaction was cooled and the solvent was removed under reduced pressure. The remaining yellow oil was diluted with ethyl acetate (1 L) and the resulting solution was poured equally into two 4-L Erlenmeyer flasks, each containing a stirred solution of 2.0 L of saturated aqueous NaHCO$_3$. Solid NaHCO$_3$ was added to each flask until the aqueous phase reached pH 8 and the layers were separated. The aqueous phase was extracted with EtOAc (2×500 mL) and the combined EtOAc layers were dried over Na$_2$SO$_4$ and filtered. After concentration and adsorption onto silica gel (150 g) the material was loaded onto a silica gel column and eluted with a solution of 70% EtOAc in hexanes. This afforded 11.5 g (37%) of the title compound as a white solid. R$_f$=0.35 (SiO$_2$, 70% EtOAc in hexanes). HPLC: R$_t$=12.6 min. $^1$H NMR (300 MHz, CDCl$_3$): δ=7.94 (d, J=8.3 Hz, 1H), 7.86 (d, J=1.6 Hz, 1H), 7.77 (dd, J=8.0 and 2.0 Hz, 1H), 5.40 (br s, 1H), 3.40 (s, 2H), 3.25 (d, J=10.5 Hz, 2H), 2.58 (d, J=10.5 Hz, 2H) and 1.49 (s, 6 H). m/z=396 [M+H]+. HiRes MS (ES): m/z 394.1011 [M−H]−.

EXAMPLE 3

4-(1,7-Dimethyl-3,5-dioxo-11-oxa-4,9-diaza-tricyclo[5.3.1.0$^{2,6}$]undec-4-yl)-2-trifluoromethyl-benzonitrile

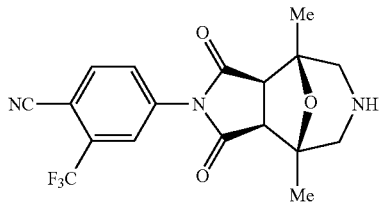

To a 1 L, three-necked round-bottomed flask with a magnetic stirring bar were added Example 2 (10.0 g, 0.025 mol) and methanol (360 mL). The suspension was stirred for 15 minutes then cooled to 0° C. A solution of TiCl$_3$ (12.1 g, 0.078 mol) in water (250 mL) was added dropwise to the stirred solution and the reaction temperature increased to 10° C. Once this addition was complete, the reaction was warmed to room temperature over 1 h and stirred at room temperature for 1 h. The resulting solution was then concentrated to remove the methanol, and then poured into a rapidly stirred biphasic system of EtOAc (1 L) and saturated aqueous NaHCO$_3$ (1 L). A thick suspension resulted, which was filtered through a Celite pad and the phases were separated. The aqueous phase was extracted with EtOAc (2×500 mL) and the combined EtOAc layers dried over Na$_2$SO$_4$, filtered and concentrated to give 9.51 g of a crude tan solid. This material was chromatographed on silica gel using 5% MeOH in methylene chloride as the eluent to give 7.22 g (75%) of the title compound as a white solid. R$_f$=0.35 (SiO$_2$, 5% MeOH in CH$_2$Cl$_2$). HPLC: R$_t$=11.2 min. $^1$H NMR (500 MHz, CDCl$_3$): δ=7.94 (d, J=8.3 Hz, 1H), 7.88 (d, J=1.8 Hz, 1H), 7.77 (dd, J=8.0 and 2.0 Hz, 1H), 3.43 (s, 2H), 2.80 (s, 4H) and 1.42 (s, 6H). m/z=380 [M+H]+. HiRes MS (ES): m/z 378.1051 [M−H]−.

EXAMPLE 4

4-(9-Isobutyryl-1,7-dimethyl-3,5-dioxo-11-oxa-4,9-diaza-tricyclo[5.3.1.0$^{2,6}$]undec-4-yl)-2-trifluoromethyl-benzonitrile

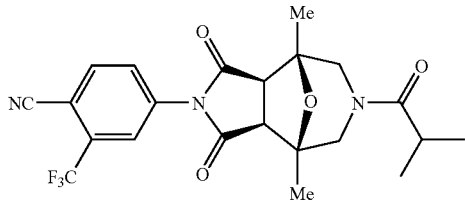

To a clear solution of Example 3 (20 mg, 0.05 mmol) and pyridine (0.04 mL, 0.5 mmol) in anhydrous methylene chloride (1 mL) was added isobutyryl chloride (0.026 mL, 0.25 mmol) under Ar. The mixture was stirred at room temperature till the reaction was completed. The reaction was quenched with saturated aqueous sodium bicarbonate solution (1 mL). The organic solution was dried. Flash chromatography purification on silica using gradient elution (0-100% EtOAc in heptane) gave 19 mg (85% yield) of Example 4. $^1$H NMR 400 MHz (CDCl$_3$) δ 7.88 (d, J=8.4 Hz, 1H), 7.79 (d, J=1.7 Hz, 1H), 7.68 (dd, J=1.9, 8.4 Hz, 1H), 4.14 (d, J =8 Hz, 1H), 3.82-3.97 (m, 1H), 3.67 (d, J=12.8 Hz, 2H), 3.25 (s, 2H), 2.80 (d, J=12.7 Hz, 2H), 1.43 (s, 6H), 1.11 (d, J=6.5 Hz, 6H). HPLC: 100% at 3.17 min (retention time) (YMC S5 ODS column 4.6×50 mm, 10-90% aqueous methanol over 4 minutes containing 0.2% phosphoric acid, 4 mL/min, monitoring at 220 nm), HiRes MS (ES): m/z 450.1648 [M−H]−.

EXAMPLE 5

4-[9-(2-Hydroxy-2-methyl-propyl)-1,7-dimethyl-3,5-dioxo-11-oxa-4,9-diaza-tricyclo[5.3.1.0$^{2,6}$]undec-4-yl]-2-trifluoromethyl-benzonitrile

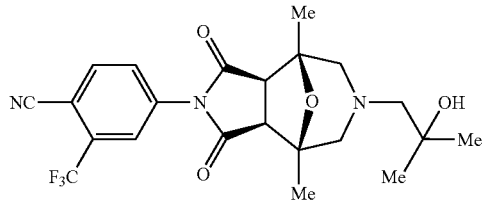

A mixture of Example 3 (30 mg, 0.08 mmol), isobutylene oxide (0.4 mL), isopropanol (0.5 mL), acetone (0.5 mL), and EtOAc (1 mL) was stirred at 100° C. in a seal tube for 40 h. Concentration and flash chromatography purification on silica using gradient elution (0-50% EtOAc in heptane) gave Example 5 as a white solid (18 mg, 0.04 mmol, 50% yield). HPLC: 100% at 3.17 min (retention time) (YMC S5 ODS column 4.6×50 mm, 10-90% aqueous methanol over 4 minutes containing 0.2% phosphoric acid, 4 mL/min, monitoring at 220 nm), MS (ES): mn/z 452.27 [M+H]+.

EXAMPLE 6

4-(9-Isopropyl-1,7-dimethyl-3,5-dioxo-11-oxa-4,9-diaza-tricyclo[5.3.1.0$^{2,6}$]undec-4-yl)-2-trifluoromethyl-benzonitrile

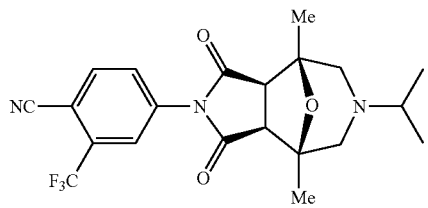

A mixture of Example 3 (50 mg, 0.13 mmol), acetone (0.25 mL), 1,2-dichloroethane, and sodium triacetoxyborohydride (100 mg, 0.47 mmol) was stirred at room temperature for 1 day. The reaction was quenched with aqueous sodium bicarbonate solution. The aqueous solution was extracted with methylene chloride. Combined organic solutions were dried (Na$_2$SO$_4$) and chromatographed on silica using gradient elution (0-50% EtOAc in heptane) to give Example 6 as a white solid (45 mg, 0.11 mmol, 82% yield). HPLC: 98% at 2.12 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 422.29 [M+H]+.

EXAMPLE 7

4-(9-Isopropyl-1,7-dimethyl-3,5-dioxo-9-oxy-11-oxa-4,9-diaza-tricyclo[5.3.1.0$^{2,6}$]undec-4-yl)-2-trifluoromethyl-benzonitrile

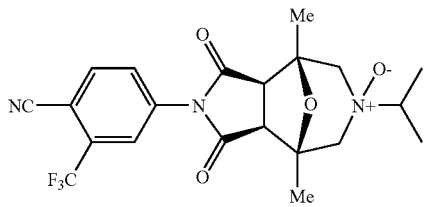

To a solution of Example 6 (27 mg, 0.064 mmol) in methylene chloride (5 mL) was added mCPBA (60%, 28 mg, 0.097 mmol). After the mixture was stirred at room temperature for 2 h, saturated aqueous sodium bicarbonate solution was added. The aqueous solution was extracted with EtOAc. Combined organic solutions were dried (Na$_2$SO$_4$) and concentrated. Preparative HPLC gave Example 7 as a trifluoroacetic acid salt (26 mg, 0.047 mmol, 74% yield). HPLC: 96% at 2.12 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 438.30 [M+H]+.

EXAMPLE 8

4-[9-(6-Chloro-pyrimidin4-yl)-1,7-dimethyl-3,5-dioxo-1 1-oxa-4,9-diaza-tricyclo[5.3.1.0$^{2,6}$]undec-4-yl]-2-trifluoromethyl-benzonitrile

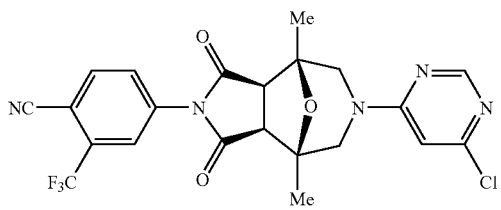

A solution of Example 3 (20 mg, 0.053 mmol) and 4,6-dichloropyrimidine (15 mg, 0.1 mmol) in DMF (0.3 mL) was stirred at 100IC for 3 h. Pyridine (0.1 mL) was then added. The mixture was stirred at 100° C. for 1 h and then cooled to room temperature. Sat aqueous sodium bicarbonate solution was added. The mixture was extracted with EtOAc. Combined organic solutions were dried (Na$_2$SO$_4$) and concentrated. The crude product was purified by flash chromatography on silica using gradient elution (0-50% EtOAc in heptane) to give Example 8 as a white solid (14 mg, 0.028 mmol, 54% yield). HPLC: 100% at 3.36 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 492.04 [M+H]+.

EXAMPLE 9

2-[4-(4-Cyano-3-trifluoromethyl-phenyl)-1,7-dimethyl-3,5-dioxo-11-oxa-4,9-diaza-tricyclo[5.3.1.0$^{2,6}$]undec-9-yl]-2-methyl-propionic acid methyl ester

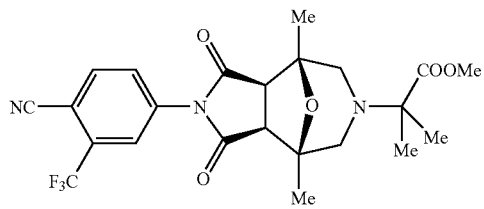

A solution of Preparation 1 (1.8 g, 5 mmol) in methylene chloride (30 mL) was cooled to −78° C. while ozone was bubbled through the reaction mixture. When the reaction mixture turned blue, the flow of ozone was stopped and nitrogen was bubbled through the mixture to remove ozone. Dimethyl sulfide (0.9 mL) was then added. The mixture was stirred at room temperature under argon for 2 h to give a clear solution (31 mL). Next, 3 mL (0.5 mmol) of the solution was mixed with alpha-aminoisobutyric acid methyl ester hydrochloride (100 mg, 0.65 mmol), triethylamine (0.1 mL, 0.72 mmol), sodium cyanoborohydride (100 mg, 1.6 mmol), and DMF (0.1 mL). The mixture was stirred at room temperature for 3 days and then concentrated. The residue was partitioned between EtOAc and water. The aqueous solution was separated and extracted with EtOAc. Combined organic solutions were dried (Na$_2$SO$_4$) and concentrated. Preparative HPLC purification and removal of trifluoroacetic acid gave Example 9 as a white solid (66 mg, 0.14 mmol, 27% yield). ). HPLC: 98% at 3.51 min (retention time) (YMC S5 ODS column 4.6×50 mm, 10-90% aqueous methanol over 4 minutes containing 0.2% phosphoric acid, 4 mL/min, monitoring at 220 nm), HiRes MS (ES): m/z 480.1748 [M+H]+.

26 mL of the ozonolysis solution was mixed with water (0.08 mL) and concentrated to give the corresponding dialdehyde acetal as a waxy solid (1.86 g, containing ca 4.2 mmol of the dialdehyde)

EXAMPLE 10

4-(9-Cyclopropylmethyl-1,7-dimethyl-3,5,8,10-tetraoxo-11-oxa-4,9-diaza-tricyclo[5.3.1.0$^{2,6}$]undec-4-yl)-2-trifluoromethyl-benzonitrile

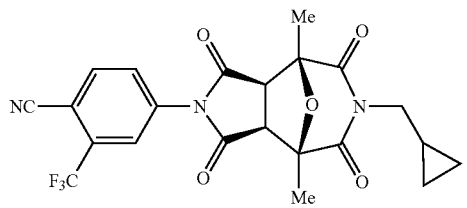

A solution of the dialdehyde acetal (0.62 g, 1.4 mmol), prepared in Example 9, in acetone (10 mL) was treated with Jone's Reagent (1.3 mL, prepared according to Froborg, J. et al. J. Org.Chem. 1975 40 122) at 0° C. After the resultant mixture was stirred at 0° C. for 30 min, isopropanol (0.5 mL) was added. The mixture was stirred at room temperature for 10 min and then filtered. The filtrate was concentrated and partitioned between EtOAc and water. The aqueous solution was extracted with EtOAc. Combined organic solutions were dried (Na$_2$SO$_4$) and concentrated. One sixth of the residue (0.23 mmol) was dissolved in acetic anhydride (0.5 mL). The mixture was stirred at 100° C. for 30 min and then concentrated. Next, 5 mL of anhydrous toluene was added and the mixture was concentrated again to give a yellow foam. The yellow foam was dissolved in anhydrous THF (2 mL). Cyclopropanemethylamine (0.04 mL, 0.46 mmol) was then added dropwise at 0° C. under argon. The mixture was stirred at 0° C. for 45 min and then concentrated. The residue was mixed with acetic acid (0.6 mL) acetic anhydride (0.6 mL), and potassium acetate (0.24 g). The mixture was stirred at 100° C. for 100 min and then concentrated. The residue was partitioned between EtOAc and water. The aqueous solution was separated and extracted with EtOAc. The combined organic solutions were washed with saturated aqueous sodium bicarbonate solution, dried (Na$_2$SO$_4$), and concentrated. The crude product was purified by flash chromatography on SiO$_2$ using gradient elution (0-50% EtOAc in heptane). Recrystallization in EtOAc-heptane gave Example 10 as a white solid (50 mg, 0.11 mmol, 47% yield). HPLC: 98% at 3.83 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z 460.00 [M−H]$^-$.

EXAMPLE 11

Isopropyl 4-(4-Cyano-3-trifluoromethylphenyl)-1,7-dimethyl-3,5-dioxo-11-oxa-4,9-diazatricyclo[5.3.1.0$^{2,6}$]undecane-9-carboxylate

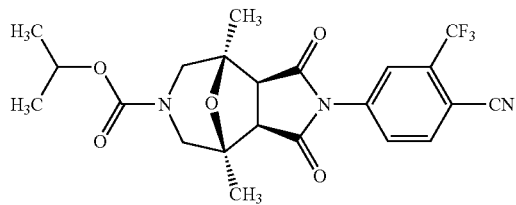

To a dry, nitrogen purged two dram amber vial with a magnetic stirring bar was added Example 3 (75 mg, 0.198 mmol), triethylamine (24 mg, 0.237 mmol), and dry CH$_2$Cl$_2$ (2 mL). The solution was stirred at room temperature and isopropyl chloroformate (1.0 M in toluene, 217 μL, 0.217 mmol) was added slowly via syringe. Once addition was complete, the reaction was stirred for 15 h at room temperature then the reaction mixture was directly loaded onto a silica gel plug. Elution with 1:1 EtOAc/hexanes afforded the Example 11 (82.3 mg) with 88% purity. This material was further purified by preparative HPLC. Concentration of the product fractions afforded 75.5 mg (82%) of the title compound as a white solid. R$_f$=0.60 (SiO$_2$, 1:1 EtOAc/hexanes). HPLC: R$_t$=15.3 min. $^1$H NMR (300 MHz, CDCl$_3$): δ=7.95 (d, J=8.0 Hz, 1H), 7.85 (d, J=1.8 Hz, 1H), 7.74 (dd, J=8.0 and 1.8 Hz, 1H), 4.9 (sept, J=6.3 Hz, 1H), 3.95 (m, 2H), 3.27 (m, 2H), 2.89 (m, 2H), 1.49 (s, 6H), and 1.27 (d, J=6.3 Hz, 6H). m/z=466 [M+H]$^+$.

EXAMPLE 12

4-(9-Methanesulfonyl-1,7-dimethyl-3,5-dioxo-11-oxa4,9-diazatricyclo[5.3.1.0$^{2,6}$]undec4-yl)-2-trifluoromethylbenzonitrile

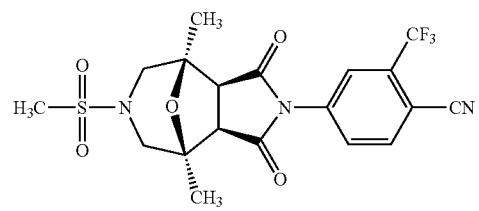

To a dry, nitrogen purged two dram amber vial with a magnetic stirring bar was added Example 3 (75 mg, 0.198 mmol), triethylamine (30 mg, 0.297 mmol), and dry CH$_2$Cl$_2$ (2 mL). The solution was stirred at room temperature and methanesulfonic chloride (34 mg, 0.297 mmol) was added slowly via syringe. The reaction was stirred for 15 h under nitrogen at room temperature and the mixture was directly loaded onto a silica gel plug. Subsequent elution with 1:1 EtOAc/hexanes afforded the product (87.0 mg) with 91% purity. This material was further purified by preparative HPLC. Concentration of the product fractions afforded 63 mg (71%) of the title compound as a white solid. R$_f$=0.28 (SiO$_2$, 1:1 EtOAc/hexanes). HPLC: R$_t$=13.4 min. $^1$H NMR (300 MHz, CDCl$_3$): δ=7.94 (d, J=8.3 Hz, 1H), 7.85 (s, 1H), 7.75 (dd, J=8.0 and 2.0 Hz, 1H), 3.65 (d, J=12.1 Hz, 2H), 3.51 (s, 2H), 2.84 (s, 2H), 2.79 (d, J=11.9 Hz, 2H) and 1.51 (s, 6H). m/z=458 [M+H]$^+$.

EXAMPLE 13

4-(4-Cyano-3-trifluoromethylphenyl)-1,7-dimethyl-3,5-dioxo-11-oxa4,9-diazatricyclo[5.3.1.0$^{2,6}$]undecane-9-carboxylic acid ethyl amide

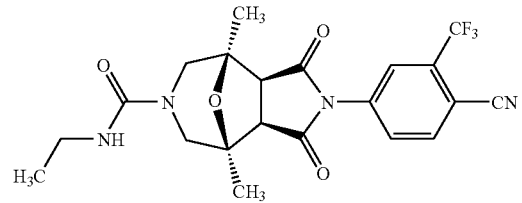

To a nitrogen purged 25 mL round bottomed flask with a magnetic stirring bar was added Example 3 (75 mg, 0.198 mmol) and THF (2 mL). Ethyl isocyanate (42 mg, 0.593 mmol) was then added and the reaction stirred at room temperature for 1 h. The solvent was removed under reduced pressure and the reaction residue diluted in 1:1 ethyl acetate/hexanes (2 mL) and loaded onto a silica gel plug. Subsequent elution with 1:1 EtOAc/hexanes afforded the product (91 mg) with 87% purity. This material was further purified by preparative HPLC. Concentration of the product fractions afforded 75 mg (84%) of Example 13 as a white solid. R$_f$=0.19 (SiO$_2$, 80% EtOAc in hexanes). HPLC: R$_t$=12.6 min. $^1$H NMR (300 MHz, CDCl$_3$): δ=7.95 (d, J=8.4 Hz, 1H), 7.85 (d, J=1.8 Hz, 1H), 7.75 (dd, J=8.0 and 2.0 Hz, 1H), 4.35 (m, 1H), 3.75 (d, J=12.9 Hz, 2H), 3.33 (s, 2H), 3.30 (m, 2H), 2.89 (d, J=12.7 Hz, 2H), 1.50 (s, 3H) and 1.17 (t, J=7.2 Hz, 3H). m/z=451 [M+H]$^+$.

PREPARATION 2

Benzyl 4-(2-Hydroxyethyl)piperazine-1-carboxylate

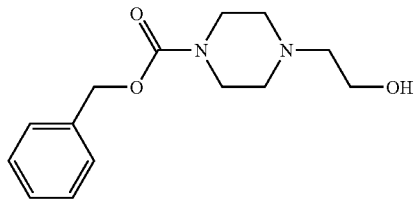

A 250 mL round bottomed flask was charged with N-(2-hydroxyethyl)piperazine (3.00 g, 24.4 mmol) followed by anhydrous THF (150 mL) and triethylamine (3.40 mL, 24.4 mmol). The resulting solution was cooled to 0° C. and a solution of benzyl chloroformate (3.10 mL, 21.8 mmol) in anhydrous THF (10 mL) was slowly added via syringe resulting in the formation of a cloudy white suspension. This suspension was stirred at 0° C. for 30 minutes, then allowed to warm to room temperature with stirring over 3 h. The reaction mixture was then concentrated under reduced pressure. Purification of the residue by silica gel chromatography, eluting with 5% MeOH in CH$_2$Cl$_2$, afforded 5.76 g (100%) of Preparation 2 as a colorless oil. R$_f$=0.60 (SiO$_2$, 5% MeOH in CH$_2$Cl$_2$). $^1$H NMR (500 MHz, CDCl$_3$): δ=7.34 (m, 5H), 5.13 (s, 2H), 3.62 (t, J=5.2 Hz, 2H), 3.52 (t, J=5.2 Hz, 4H), 2.64 (br s, 1H), 2.55 (t, J=5.2 Hz, 2H) and 2.47 (br s, 4H). m/z=265 [M+H]$^+$.

PREPARATION 3

Benzyl 4-(2-Chloroethyl)piperazine-1-carboxylate Hydrochloride

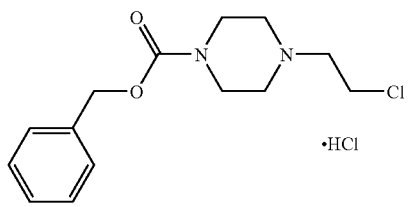

A 100 mL round bottomed flask was charged with benzyl 4-(2-hydroxyethyl) piperazine-1-carboxylate (1.02 g, 3.85 mmol) and the flask cooled to 0° C. Thionyl chloride (2 mL, 27.4 mmol) was slowly added and the resulting yellow solution warmed to room temperature with stirring over 2 h. After this time, the mixture was concentrated under reduced pressure and the residual thionyl chloride was removed by coevaporation with toluene (3×15 mL). This afforded 1.17 g (95%) of the title compound as an off-white solid. $^1$H NMR (500 MHz, CD$_3$OD): δ=7.35 (m, 5H), 5.55 (s, 2H), 4.27 (m, 2H), 3.99 (t, J=6.1 Hz, 2H), 3.61 (t, J=6.1 Hz, 4H), 3.38 (m, 2H) and 3.19 (m, 2H). m/z=283 [M+H]$^+$.

EXAMPLE 14

Benzyl 4-{2-[4-(4-Cyano-3-trifluoromethylphenyl)-1,7-dimethyl-3,5-dioxo-11-oxa4,9-diazatricyclo [5.3.1.0$^{2,6}$]undec-9-yl]-ethyl}piperazine-1-carboxylate

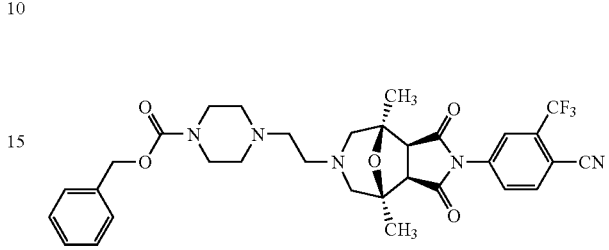

A 250 mL round bottomed flask was charged with Example 3 (1.00 g, 2.63 mmol), Preparation 3 (0.848 g, 2.65 mmol), anhydrous N,N-dimethylformamide (60 mL), and N,N-diisopropylethylamine (1.40 mL, 8.03 mmol). The resulting mixture was heated at 100° C. for 3 days. After this time the reaction mixture was cooled and concentrated under reduced pressure to afford an amber solid. Purification of this solid by silica gel chromatography, eluting with 80% EtOAc in hexanes to 100% EtOAc afforded 466 mg (28%) of the title compound as an off-white solid. R$_f$=0.56 (SiO$_2$, 100% EtOAc). HPLC: R$_t$=14.1 min. $^1$H NMR (500 MHz, CDCl$_3$): δ=7.93 (d, J=8.0 Hz, 1H), 7.87 (d, J=1.8 Hz, 1H), 7.75 (dd, J=8.0 and 1.8 Hz, 1H), 7.34 (m, 5H), 5.13 (s, 2H), 3.51 (t, J=5.0 Hz, 4H), 3.36 (s, 2H), 2.77 (d, J=11.3 Hz, 2H), 2.55 (t, J=6.1 Hz, 2H), 2.49 (t, J=6.1 Hz, 2H), 2.43 (br s, 4H), 2.15 (d, J=11.3 Hz, 2H) and 1.43 (s, 6H). m/z=626 [M+H]$^+$.

EXAMPLE 15

4-[1,7-Dimethyl-3,5-dioxo-9-(2-piperazin-1-yl-ethyl)-11-oxa4,9-diazatricyclo[5.3.1.0$^{2,6}$]undec4-yl]-2-trifluoromethylbenzonitrile

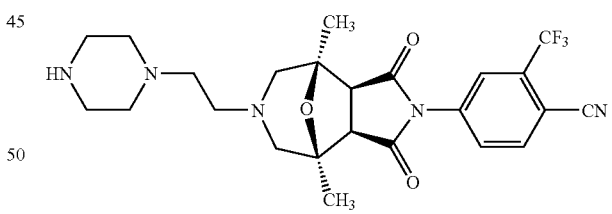

A 250 mL Parr hydrogenation bottle was charged with Example 14 (89.3 mg, 0.116 mmol), EtOH (15 mL) and palladium on carbon (39.0 mg, 10% Pd, 50% wet). The bottle was placed on a Parr hydrogenation apparatus and shook under a 30 psi hydrogen atmosphere for 2 h. Subsequent filtration of the contents over celite and concentration of the filtrate afforded an amber solid. This solid was purified by silica gel chromatography, eluting with 20-40% MeOH in CH$_2$Cl$_2$, affording 47 mg (67%) of the title compound as an off-white solid. R$_f$=0.40 (SiO$_2$, 10% MeOH in CH$_2$Cl$_2$). HPLC: R=t10.4 min. $^1$H NMR (500 MHz, CDCl$_3$): δ=7.93 (d, J=8.3 Hz, 1H), 7.87 (d, J=1.8 Hz, 1H), 7.75 (dd, J=8.3 and 1.8 Hz, 1H), 3.38 (s, 2H), 2.88 (t, J=4.8 Hz, 4H), 2.78 (d, J=11.4 Hz, 2H), 2.55 (m, 2H), 2.46 (m, 2H), 2.43 (br s, 4H), 2.16 (d, J=11.4 Hz, 2H) and 1.43 (s, 6H). m/z=492 [M+H]$^+$.

EXAMPLE 16

4-(4-Cyano-3-trifluoromethylphenyl)-1,7-dimethyl-3,5-dioxo-11-oxa4,9-diazatricyclo[5.3.1.0$^{2,6}$]undecane-9-carboxylic Acid 2-(4-tert-Butoxycarbonyl-piperazin-1-yl)-ethyl Ester

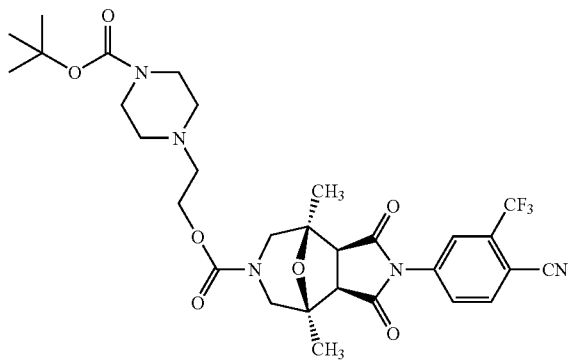

To a dry, nitrogen purged 100 mL round-bottomed flask equipped with a magnetic stirring bar was added dry CH$_2$Cl$_2$ (15 mL) and a 20% solution of phosgene in toluene (4.20 mL, 7.90 mmol). The resulting solution was stirred and cooled to 0° C. and pyridine (640 µL, 7.90 mmol) was added to afford a yellow suspension. Additional CH$_2$Cl$_2$ (10 mL) was added and a solution of tert-butyl-4-(2-hydroxyethyl)piperazine-1-carboxylate (1.67 g, 7.20 mmol) in CH$_2$Cl$_2$ (10 mL) was added dropwise via syringe over 15 min. The reaction was then warmed to room temperature over 0.5 h and a solution of Example 3 (2.50 g, 6.60 mmol) in CH$_2$Cl$_2$ (20 mL) was added dropwise over 20 min. followed by pyridine (640 µL, 7.90 mmol). The reaction was stirred at room temperature for 15 h, concentrated and the resulting material purified by silica gel chromatography using 95% EtOAc in hexanes to 100% EtOAc as the eluent. The title compound, 2.45 g (59%), was a white solid. R$_f$=0.13 (SiO$_2$, 80% EtOAc in hexanes). HPLC: R$_t$=13.5 min. $^1$H NMR (500 MHz, CDCl$_3$): δ=7.95 (d, J=8.3 Hz, 1H), 7.85 (d, J=1.6 Hz, 1H), 7.74 (dd, J=8.3 and 2.0 Hz, 1H), 4.60 (br s, 1H), 4.05 (br s, 1H), 3.90 (br s, 1H), 3.41 (br s, 4H), 3.30 (s, 2H), 2.92 (m, 2H), 2.65 (t, J=5.4 Hz, 2H), 2.45 (br s, 4H), 1.48 (s, 6H) and 1.45 (s, 9H). m/z=636 [M+H]$^+$.

EXAMPLE 17

4-(4-Cyano-3-trifluoromethylphenyl)-1,7-dimethyl-3,5-dioxo-11-oxa4,9-diazatricyclo[5.3.1.0$^{2,6}$]undecane-9-carboxylic Acid 2-Piperazin-1-yl-ethyl Ester

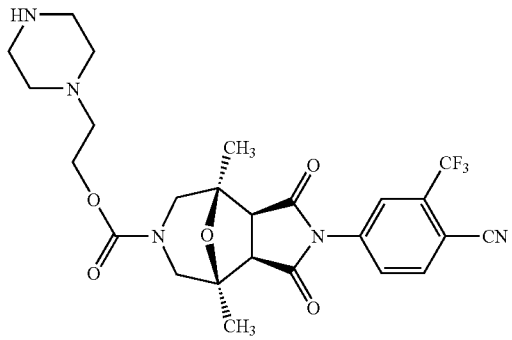

To a dry, nitrogen purged 100 mL round-bottomed flask equipped with a magnetic stirring bar was added Example 16 (2.24 g, 3.52 mmol) and dry CH$_2$Cl$_2$ (20 mL). The solution was stirred and trifluoroacetic acid (4 mL) was added slowly over 5 min. After stirring at room temperature for 5 h, saturated aqueous Na$_2$CO$_3$ was added until the aqueous layer reached pH 9. The two phases were separated and the aqueous phase extracted with CH$_2$Cl$_2$ (2×50 mL). After combining, the CH$_2$Cl$_2$ layers were dried over Na$_2$SO$_4$, filtered, and concentrated. The resulting residue was chromatographed on silica gel using 20-40% MeOH in CH$_2$Cl$_2$ as the eluent to give 1.67 g (88%) of the title compound as a white solid. R$_f$=0.26 (SiO$_2$, 10% MeOH in CH$_2$Cl$_2$). HPLC: R$_t$=10.6 min. $^1$H NMR (500 MHz, CDCl$_3$): δ=7.95 (d, J=8.3 Hz, 1H), 7.85 (d, J=1.7 Hz, 1H), 7.74 (dd, J=8.3 and 2.0 Hz, 1H), 4.33 (m, 1H), 4.21 (m, 1H), 4.04 (d, J=11.3 Hz, 1H), 3.91 (d, J=11.3 Hz, 1H), 3.33 (s, 2H), 2.95 (m, 1H), 2.87 (t, J=4.8 Hz, 4H), 2.63 (m, 2H), 2.50 (br s, 4H), 1.98 (s, 2H) and 1.48 (s, 6H). m/z=536 [M+H]$^+$.

EXAMPLE 18

Ethyl 4-{2-[4-(4-Cyano-3-trifluoromethylphenyl)-1,7-dimethyl-3,5-dioxo-11-oxa-4,9-diazatricyclo[5.3.1.0$^{2,6}$]undec-9-yl]-ethyl}piperazine-1-carboxylate

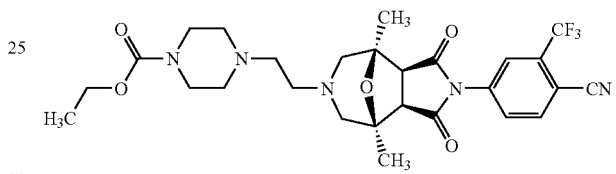

To a dry, nitrogen purged two dram amber vial with a magnetic stirring bar was added Example 15 (30 mg, 0.061 mmol), triethylamine (8 mg, 0.079 mmol) and dry CH$_2$Cl$_2$ (2 mL). The solution was stirred at room temperature and ethyl chloroformate (8 mg, 0.073 mmol) added slowly via syringe. Once addition was complete, the reaction was stirred for 15 h at room temperature and then directly loaded onto a silica gel plug. Elution with 100% EtOAc afforded the crude product, which was further purified by preparative HPLC. Concentration of the product fractions afforded 26.2 mg (76%) of the title compound as a white solid. R$_f$=0.48 (SiO$_2$, 5% MeOH in CH$_2$Cl$_2$). HPLC: R$_t$=12.5 min. $^1$H NMR (500 MHz, CDCl$_3$): δ=7.94 (d, J=8.3 Hz, 1H), 7.87 (d, J=1.7 Hz, 1H), 7.75 (dd, J=8.3 and 1.7 Hz, 1H), 4.13 (q, J=7.1 Hz, 2H), 3.48 (m, 4H), 3.37 (s, 2H), 2.77 (d, J=11.3 Hz, 2), 2.56 (m, 2H), 2.49 (m, 2H), 2.42 (m, 4H), 2.16 (d, J=11.3 Hz, 2H), 1.44 (s, 6H) and 1.26 (t, J=7.1 Hz, 3H). m/z=564 [M+H]$^+$.

EXAMPLE 19

4-(1,7-Dimethyl-3,5-dioxo-9-{2-[4-(3,3,3-trifluoropropionyl)-piperazin-1-yl]-ethyl}-11-oxa4,9-diazatricyclo[5.3. 1.0$^{2,6}$] undec4-yl)-2-trifluoromethylbenzonitrile

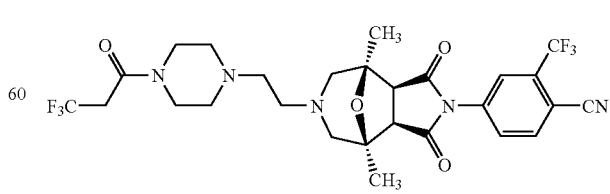

To a dry, nitrogen purged two dram amber vial with a magnetic stirring bar was added Example 15 (30 mg, 0.061 mmol), triethylamine (8 mg, 0.079 mmol) and dry CH$_2$Cl$_2$ (2 mL). The solution was stirred at room temperature and 3,3,3-trifluoropropionic acid chloride (10 mg, 0.068 mmol) added slowly. Once addition was complete, the reaction was stirred for 15 h at room temperature and the reaction mixture directly loaded onto a silica gel plug. Elution with 4% MeOH in CH$_2$Cl$_2$ afforded the crude product, which was further purified by preparative HPLC. Concentration of the product fractions afforded 24.2 mg (66%) of the title compound as a white solid. R$_f$=0.48 (SiO$_2$, 5% MeOH in CH$_2$Cl$_2$). HPLC: R$_t$=12.7 min. $^1$H NMR (500 MHz, CDCl$_3$): δ=7.94 (d, J=8.3 Hz, 1H), 7.87 (d, J=1.8 Hz, 1H), 7.75 (dd, J=8.3 and 1.8 Hz, 1H), 3.66 (m, 2H), 3.48 (m, 2H), 3.36 (s, 2H), 3.23 (q, J$_{H-F}$=10.0 Hz, 2H), 2.77 (d, J=11.3 Hz, 2H), 2.56 (m, 2H), 2.52-2.46 (m, 6H), 2.16 d, J=11.3 Hz, 2H) and 1.44 (s, 6H). m/z=602 [M+H]$^+$.

EXAMPLE 20

4-{9-[2-(4-Ethanesulfonylpiperazin-1-yl)ethyl]-1,7-dimethyl-3,5-dioxo-11-oxa-4,9-diazatricyclo[5.3.1.0$^{2,6}$]undec4-yl}-2-trifluoromethylbenzonitrile

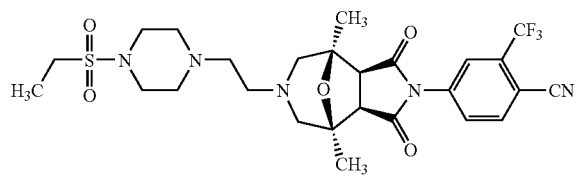

To a dry, nitrogen purged two dram amber vial with a magnetic stirring bar was added Example 15 (30 mg, 0.061 mmol), triethylamine (10 mg, 0.093 mmol) and dry CH$_2$Cl$_2$ (2 mL). The solution was stirred at room temperature and ethanesulfonyl chloride (14 mg, 0.105 mmol) added slowly via syringe. The reaction was stirred at room temperature for 3 h under nitrogen then loaded onto a silica gel plug. Elution with 3% MeOH in methylene chloride afforded 30.5 mg (86%) of the title compound as a white solid. R$_f$=0.39 (SiO$_2$, 5% MeOH in CH$_2$Cl$_2$). HPLC: R$_t$=12.6 min. $^1$H NMR (500 MHz, CDCl$_3$): δ=7.94 (d, J=8.3 Hz, 1H), 7.87 (d, J=1.8 Hz, 1H), 7.75 (dd, J=8.3 and 1.8 Hz, 1H), 3.36 (s, 2H), 3.32 (m, 4H), 2.95 (q, J=7.4 Hz, 2H), 2.77 (d, J=11.4 Hz, 2H), 2.54 (br s, 8H), 2.15 (d, J=11.4 Hz, 2H), 1.44 (s, 6H) and 1.37 (t, J=7.4 Hz, 3H). m/z=584 [M+H]$^+$.

EXAMPLE 21

4-{2-[4-(4-Cyano-3-trifluoromethylphenyl)-1,7-dimethyl-3,5-dioxo-11-oxa4,9-diazatricyclo[5.3.1.0$^{2,6}$]undec-9-yl]-ethyl}piperazine-1-carboxylic acid isopropylamide

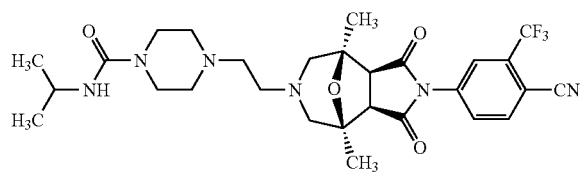

To a dry, nitrogen purged two dram amber vial with a screw top Teflon cap and a magnetic stirring bar was added Example 15 (30 mg, 0.061 mmol) and dry tetrahydrofuran (2 mL). The solution was stirred at room temperature and isopropylisocyanate (16 mg, 0.183 mmol) added slowly via syringe. The reaction was stirred for 3 h under nitrogen at room temperature after which time the reaction solution loaded directly onto a silica gel plug. Elution with 3% MeOH in methylene chloride and concentrating the eluent under reduced pressure afforded 30.9 mg (88%) of the title compound as a white solid. R$_f$=0.33 (SiO$_2$, 5% MeOH in CH$_2$Cl$_2$). HPLC: R$_t$=12.0 min. $^1$H NMR (500 MHz, CDCl$_3$): δ=7.94 (d, J=8.3 Hz, 1H), 7.87 (s, 1H), 7.75 (dd, J=8.3 and 1.9 Hz, 1H), 4.18 (d, J=7.1 Hz, 1H), 3.97 (sept, J=6.5 Hz, 1H), 3.37 (s, 2H), 3.34 (m, 4H), 2.77 (d, J=11.3 Hz, 2H), 2.56 (m, 2H), 2.50 (m, 2H), 2.45 (m, 4H), 2.16 (d, J=11.3 Hz, 2H), 1.43 (s, 6H) and 1.15 (d, J=6.5 Hz, 6H). m/z=577 [M+H]$^+$.

PREPARATION 4

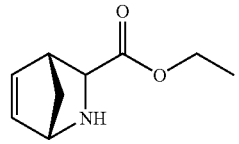

Ethyl-gloxylate (50% in toluene, 48.0 g, 207.0 mmol) and freshly cracked cyclopentadiene (32.0 g, 485 mmol) were mixed in saturated NH$_4$Cl solution (100 mL) and stirred at 22° C. for 16 h. The reaction mixture was washed with diethyl ether (2×250 mL). Then pH was adjusted to 8 with saturated NaHCO$_3$ and extracted with CH$_2$Cl$_2$ (3×300 mL). The combined organic layers were washed with brine, dried over MgSO$_4$ and filtered. The filtrate was concentrated in vacuo to give 24 g of Preparation 4 as a light brown liquid in 69% yield. NMR: CDCl$_3$ (ppm) 6.28 (1H, m), 5.84 (1H, m), 4.1 (2H, m), 4.0 (1H, s), 3.9 (1H, d, J=3.2 Hz), 3.41 (1H, s), 1.6 (1H, d, J=8.4 Hz), 1.41 (1H, d, J=8.4 Hz), 1.26 (3H, m).

PREPARATION 5

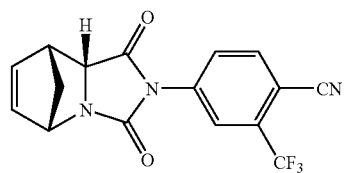

Preparation 4 (above) (2.2 g, 13.0 mmol) and 4-isocyanato-2-(trifluoromethyl) benzonitrile (2.76 g, 13.0 mmol) were mixed in toluene (80 mL). The reaction mixture was stirred at 22° C. under nitrogen for 16 h. 4 Å molecular sieves (3.0 g) was added and the reaction mixture was heated at 80° C. for 2 h. Next, the reaction mixture was cooled to 22° C. and filtrated through celite. The filtrate was partitioned between saturated NH$_4$Cl solution (100 mL) and EtOAc (100 mL). The organic layer was separated and washed with brine, dried over MgSO$_4$ and filtered. The filtrate was concentrated in vacuo to give a crude white solid which was purified with flash chromatography in ISCO using 120 g column, Flow rate: 85 mL/min, solvent A: CH$_2$Cl$_2$, solvent B: 10% MeOH/CH$_2$Cl$_2$. Gradient: 0% B to 15% B in 25 minutes to give 2.15 g of white solid in 50% yield. 98% at 2.830 min (retention times) (YMC ODS-A column 4.6×50 mm eluting with 10-90% aqueous methanol over 4 minutes containing 0.1% H$_3$PO$_4$, 4 mL/min, monitoring at 220 nm). MS (ES): m/z 332.27 [M−H]$^{30}$. NMR: CDCl$_3$ (ppm) 7.85 (2H, m), 7.7 (1H, d, J=6.5 Hz), 6.51 (1H, m), 6.29 (1H, m), 4.8 (1H, s), 4.4 (1H, d, J=3.3 Hz), 3.7 (1H, s), 1.98 (1H, d, J=9.2 Hz), 1.86 (1H, d, J=9.2 Hz).

PREPARATION 6

N-(4-cyano-3-(trifluoromethyl)phenyl)-3-(hydroxymethyl)-2-aza-bicyclo[2.2.1]hept-5-ene-2-carboxamide

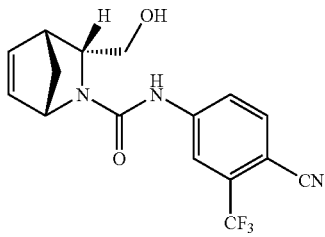

To a solution of Preparation 5 (2.00 g, 6.01 mmol) in tetrahydrofuran (THF, 20 mL) and methanol (20 mL) at 22° C. was added NaBH$_4$ (0.90 g, 24.0 mmol). The resulting reaction mixture was stirred for 30 min, then acidified by addition of saturated NH$_4$Cl solution (200 mL), and extracted with CH$_2$Cl$_2$ (3×250 mL). The organic phases were combined, dried over anhydrous sodium sulfate, and filtered. The filtrate was concentrated in vacuo to give the crude ring opened alcohol-urea intermediate 2.0 g as a white solid. 98% at 3.0 min (retention times) (YMC ODS-A column 4.6×50 mm eluting with 10-90% aqueous methanol over 4 minutes containing 0.1% H$_3$PO$_4$, 4 mL/min, monitoring at 220 nm). MS (ES): m/z 336.22 [M−H]$^+$. MS (ES): m/z 338.27 [M+H]$^+$. NMR: CDCl$_3$ (ppm) 7.77 (1H, s), 7.66 (1H, s), 7.64 (1H, d, J=1.1 Hz), 5.91 (1H, m), 5.71 (1H, m), 5.32 (IH, d, 9.33 Hz), 5.13 (1H, d, 7.88 Hz), 4.51 (1H, m), 3.80 (1H, m), 3.66 (1H, dd, J=1.51, 1.48 Hz), 3.13 (1H, m), 2.41 (1H, m) and 2.30 (1H, m).

PREPARATION 7

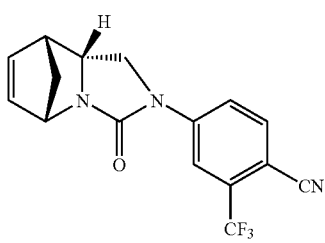

To a solution of Preparation 6 (2.00 g, 6.01 mmol) in tetrahydrofuran (THF, 85 mL) at 0° C. was added LiHMDS (1.0M solution in THF, 19.6 mL, 19.6 mmol) drop wise followed by TsCl (2.50 g, 13.0 mmol) in THF (15 mL) solution. The reaction mixture was then warmed up to 22° C. and left at 22° C. under nitrogen for 16 h. Next, the reaction mixture was partitioned between water (150 mL) and EtOAc (200 mL). The organic layer was separated and washed with brine, dried over MgSO$_4$ and filtered. The filtrate was concentrated in vacuo to give a light brown color solid which was purified with flash chromatography in ISCO using 120 g column, Flow rate: 85 mL/min, solvent A: CH$_2$Cl$_2$, solvent B: 2% MeOH in CH$_2$Cl$_2$. Gradient: 0% B to 50% B in 25 minutes to give 1.4 g of ring closed urea as a white solid in 74% yield. 100% at 2.932 min (retention times) (YMC ODS-A column 4.6×50 mm eluting with 10-90% aqueous methanol over 4 minutes containing 0.1% H$_3$PO$_4$, 4 mL/min, monitoring at 220 nm). MS (ES): m/z 378.27 [M−H+OAc]$^+$. NMR: CDCl$_3$ (ppm) 7.71 (1H, d, J=1.85 Hz), 7.56 (2H, m), 6.55 (1H, m), 6.03 (1H, m), 4.39 (1H,s), 4.15 (1H, m), 3.65 (1H, t, J=9.5 Hz), 3.32 (1H, m), 3.26 (1H, s), 1.77 (1H, d, J=8.85 Hz) 1.62 (1H, d, J=8.88 Hz).

EXAMPLE 22

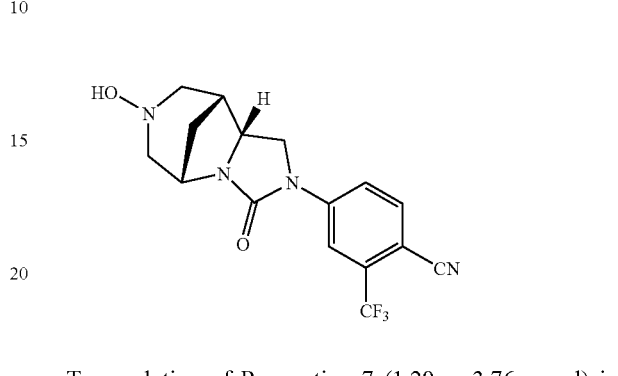

To a solution of Preparation 7 (1.20 g, 3.76 mmol) in methanol (15 mL) and CH$_2$Cl$_2$ (15 mL) at −78° C. was passed through ozone until the color of the solution changed to light blue for 5 min. Nitrogen was passed through until the light blue color disappeared. NaCNBH$_3$ (0.468 g, 7.52 mmol) was added at 0° C. The reaction was stirred at 0° C. for 15 min. Acetic acid (1.0 mL), NH$_2$OH (50% in water, 0.92 mL, 15.0 mmol) and acetic acid (4.0 mL) were added. The reaction mixture was then heated to reflux (53° C.) for 2 h. During the heating, another 0.600 g of NaCNBH$_3$ in 3 portions was added. The reaction was cooled to 22° C., concentrated in vacuo, and partitioned between saturated sodium bicarbonate (150 mL) and EtOAc (200 mL). The organic layer was separated and washed with brine, dried over MgSO$_4$, and filtered. The filtrate was concentrated in vacuo to give crude white solid which was purified with flash chromatography in ISCO using 120 g column, Flow rate: 85 mL/min, solvent A: CH$_2$Cl$_2$, solvent B: EtOAc. Gradient: 0% B to 100% B in 25 minutes to give 0.530 g of white solid in 41% yield. 98% at 2.568 min (retention times) (YMC ODS-A column 4.6×50 mm eluting with 10-90% aqueous methanol over 4 minutes containing 0.1% H$_3$PO$_4$, 4 mL/min, monitoring at 220 nm). MS (ES): m/z 411.30 [M−H+OAc]$^+$. NMR: CD$_3$COCD$_3$ (ppm) 8.33 (1H, s), 7.98 (1H, d, J=8.7 Hz), 7.82 (1H, dd, J=2.2 Hz), 4.2 (2H, m), 4.16 (1H, m), 3.91 (1H, m), 3.71 (1H, m), 3.57 (1H, m), 2.85 (1H, m), 2.48 (2H, m), 2.2 (1H, m), 1.98 (1H, m).

EXAMPLE 23

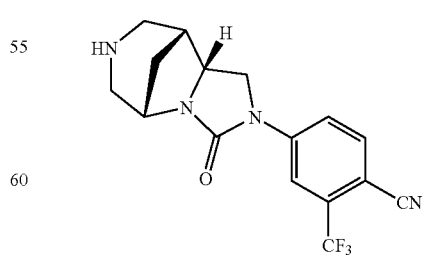

Example 22 (0.360 g, 1.023 mmol) was dissolved in hot EtOH (14 mL), saturated NH$_4$Cl (7.0 mL) was added followed by In$^0$ (0.230 g, 2.0 mmol). The reaction mixture was heated (93° C.) to reflux under nitrogen for 16 h. Cooled to 22° C., partitioned between 3M Na$_2$CO$_3$ (pH~12)(150 mL) and EtOAc (100 mL). The organic layer was separated and washed with brine, dried over MgSO$_4$, and filtered. The filtrate was concentrated in vacuo to give 0.034 g of Example 23 as a white solid in 99% yield. 97% at 1.940 min (retention times) (YMC ODS-A column 4.6×50 mm eluting with 10-90% aqueous methanol over 4 minutes containing 0.1% H$_3$PO$_4$, 4 mL/min, monitoring at 220 nm). MS (ES): m/z 395.29 [M−H+OAc]$^+$. NMR: CDCl$_3$ (ppm) 7.87 (1H, d, J=2.0 Hz), 7.75 (1H, dd, J=2.1 Hz), 7.68 (1H, m), 4.25 (1H, m), 4.08 (1H, t, J=8.3 Hz), 3.86 (1H, m), 3.81 (1H, t, J=8.6 Hz), 3.35 (1H, m), 3.19 (1H, m), 2.98 (1H, d, J=11.6Hz), 2.58 (1H, d, J=11.1 Hz) 2.27 (1H, m), 2.12 (1H, d, J=3.4 Hz), 1.91 (1H, d, J=11.6 Hz).

EXAMPLE 24

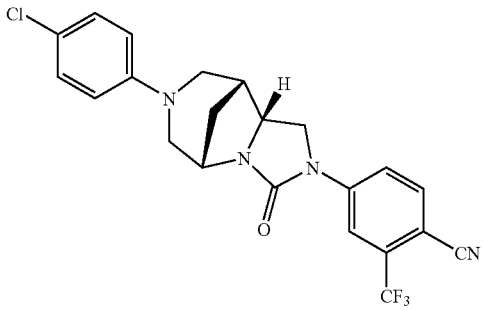

To a solution of Preparation 7 (0.100 g, 0.313 mmol) in methanol (1.5 mL) and CH$_2$Cl$_2$ (1.5 mL) at −78° C. was passed through ozone until the color of the solution changed to light blue for 5 min. Nitrogen was passed through until the light blue color disappeared NaCNBH$_3$ (0.120 g, 1.90 mmol) was added followed by 4-chlorobenzenamine (0.080 mg, 0.63 mmol) and acetic acid (0.200 mL). The reaction mixture was stirred at 22° C. under nitrogen for 3 h. Saturated NaHCO$_3$ (25 mL) was added, extracted with EtOAc (3×25 mL). The organic layers were combined, dried over sodium sulfate, and filtered. The filtrate was concentrated in vacuo to give crude. material which was purified by flash chromatography in ISCO using 40 g column, 40 mL/min A: Hexane, B: EtOAc. Gradient: 0% to 100% B in 25 min to give 0.075 g of light purple solid in 54% yield. 98% at 3.573 min (retention times) (YMC ODS-A column 4.6×50 mm eluting with 10-90% aqueous methanol over 4 minutes containing 0.1% H$_3$PO$_4$, 4 mL/min, monitoring at 220 nm). MS (ES): m/z 505.25 [M−H+OAc]$^+$. NMR: CDCl$_3$ (ppm) 7.78 (1H, s), 7.58 (2H,s), 7.00 (1H, d, J=6.95 Hz), 6.63 (1H, d, J=8.9 Hz), 4.2 2H, m), 4.06 (1H, m), 3.85 (1H, t, J=9.2 Hz), 3.71 (1H, t, J=8.5 Hz), 3.62 (1H, d, J=12.0 Hz), 3.04 (1H, d, J=11.8 Hz), 2.65 (1H, d, J=11.7 Hz) 1.95 (1H, m).

EXAMPLE 25

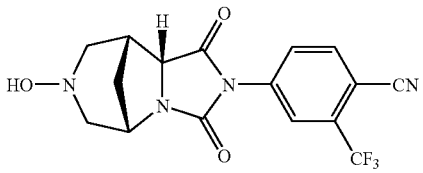

To a solution of Preparation 5 (1.20 g, 3.60 mmol) in methanol (15 mL) and CH$_2$Cl$_2$ (15 mL) at −78° C. was passed through ozone until the color of the solution changed to light blue for 5 min. Nitrogen was passed through until the light blue color disappeared. NaCNBH$_3$ (0.600 g, 9.50 mmol) was added at 0° C. The reaction was stirred at 0° C. for 15 min. Acetic acid (1.0 mL), NH$_2$OH (50% in water, 0.88 mL, 14.4 mmol) and acetic acid (4.0 mL) were added. The reaction mixture was then heated to reflux (53° C.) for 2 h. During the heating, another 0.600 g of NaCNBH$_3$ in 3 portions was added. Next, the reaction mixture was cooled to 22° C., concentrated in vacuo, and partition between saturated sodium bicarbonate (150 mL) and EtOAc (200 mL). The organic layer was separated and washed with brine, dried over MgSO$_4$, and filtered. The filtrate was concentrated in vacuo to give crude white solid which was purified by flash chromatography in ISCO using 120 g column, Flow rate: 85 mL/min, solvent A: CH$_2$Cl$_2$, solvent B: EtOAc. Gradient: 0% B to 50% B in 25 minutes to give 0.170 g of white solid in 13% yield. 98% at 2.467 min (retention times) (YMC ODS-A column 4.6×50 mm eluting with 10-90% aqueous methanol over 4 minutes containing 0.1% H$_3$PO$_4$, 4 mL/min, monitoring at 220 nm). MS (ES): m/z 365.19 [M−H]$^+$. NMR: CDCl$_3$ (ppm) 8.15 (2H, m), 8.07 (1H, d, J=8.3 Hz), 4.58 (1H, d, J=5.3 Hz), 4.11 (1H, t, J=4.3 Hz), 3.76 (1H, m), 3.41 (1H, m), 2.8 (3H, m), 2.57 (1H, d, J=10.6 Hz), 2.30 (1H, m), 2.05 (2H, m).

EXAMPLE 26

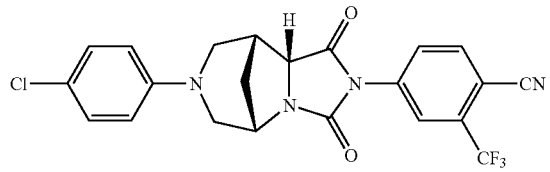

To a solution of Preparation 5 (0.160 g, 0.48 mmol) in methanol (1.5 mL) and CH$_2$Cl$_2$ (1.5 mL) at −78° C. was passed through ozone until the color of the solution changed to light blue for 5 min. Nitrogen was passed through until the light blue color disappeared. NaCNBH$_3$ (0.150 g, 2.39 mmol) was added followed by 4-chlorobenzenamine (0.120 mg, 0.96 mmol) and acetic acid (0.500 mL). The reaction mixture was stirred at 22° C. under nitrogen for 3 h. Saturated NaHCO$_3$ (25 ml) was added, and the reaction mixture was extracted with EtOAc (3×25 mL). The organic layers were combined, dried over anhydrous sodium sulfate, and filtered. The filtrate was concentrated in vacuo to give a crude material, which was purified by flash chromatography in ISCO using 40 g column, 40 mL/min A: Hexane, B: EtOAc. Gradient: 0% to 100% B in 25 min to give 0.036 g of white solid in 18% yield. 95% at 3.463 min (retention times) (YMC ODS-A column 4.6×50 mm eluting with 10-90% aqueous methanol over 4 minutes containing 0.1% H$_3$PO$_4$, 4 mL/min, monitoring at 220 nm). MS (ES): m/z 459.23 [M−H]$^+$. NMR: CDCl$_3$ (ppm) 8.12 (1H, d, J=8.3 Hz), 7.7 (1H, m), 7.67 (1H, d, J=1.4 Hz), 7.17 (2H, d, J=6.8 Hz), 6.8 (2H, d, J=9.0 Hz), 4.7 (1H, d, J=5.3 Hz), 4.3 (2H, m), 3.13 (1H, d, J=11.8 Hz), 2.9 (2H, m), 2.8 (1H, d, J=13.3 Hz), 2.06 (1H, m), 2.3 (1H, d, 11.9Hz), 2.07 (1H, m).

EXAMPLE 27

2,2,3,3,3-Pentafluoropropyl 4-{2-[4-(4-Cyano-3-trifluoromethylphenyl)-1,7-dimethyl-3,5-dioxo-11-oxa-4,9-diazatricyclo[5.3.1.0$^{2,6}$]undec-9-yl]-ethyl}piperazine-1-carboxylate

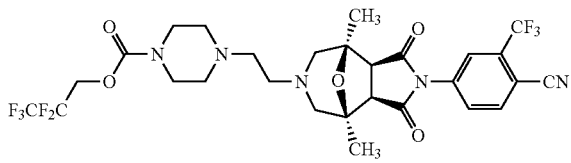

To a dry, nitrogen purged 10 mL round bottomed flask equipped with a magnetic stirring bar was added dry CH$_2$Cl$_2$ (2 mL) and 20% phosgene in toluene (64 µL, 0.122 mmol), and the stirred solution was cooled to 0° C. 2,2,3,3,3-Pentafluoropropanol (16.7 mg, 0.112 mol) was added slowly via syringe, followed by pyridine (10 mg, 0.122 mol). The reaction was warmed to room temperature over 0.5 h and stirred for a further 0.5 h at room temperature. A solution of Example 15 (50 mg, 0.102 mmol) in CH$_2$Cl$_2$ (2 mL) was added along with additional pyridine (10 mg, 0.122 mol). The reaction was stirred at room temperature for 15 h and the solution was directly applied to a silica gel plug. After elution with 3% MeOH in CH$_2$Cl$_2$, fractions containing the title compound were combined and concentrated. The resulting residue was diluted in acetonitrile (2 mL) and was further purified by preparative HPLC. After combining and concentrating the product containing fractions, 30.5 mg (45%) of Example 27 was isolated as a white solid. R$_f$=0.20 (SiO$_2$, 1:1 EtOAc/hexanes). HPLC: R$_t$=14.3 min. $^1$H NMR (500 MHz, CDCl$_3$): δ=7.94 (d, J=8.3 Hz, 1H), 7.86 (d, J=1.6 Hz, 1H), 7.75 (dd, J=8.3 and 1.9 Hz, 1H), 4.60 (t, J$_{H-F}$=12.5 Hz, 2H), 3.81 (br s, 4H), 3.46 (s, 2H), 3.06 (m, 6H), 2.85 (d, J=11.1 Hz, 2H), 2.77 (m, 2H), 2.16 (d, J=11.1 Hz, 2H) and 1.45 (s, 6H). m/z=668 [M+H]$^+$.

EXAMPLES 28 to 60

Examples 28 to 60 were prepared according to the general procedure indicated in Table 1 and had the general formula represented by

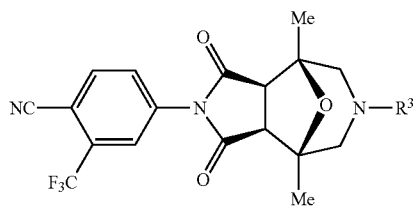

wherein R$^3$ is defined in Table 1.

Examples 28-46 were evaluated by HPLC method A. Examples 47-60 were evaluated by HPLC method C.

TABLE 1

| Ex. No. | G | Compound Name | Retention Time Min. | Procedure of Example |
|---|---|---|---|---|
| 28 | ![3-methanesulfonyl-phenyl] | 4-[9-(3-Methanesulfonyl-phenyl)-1,7-dimethyl-3,5-dioxo-11-oxa-4,9-diaza-tricyclo[5.3.1.0$^{2,6}$]undec-4-yl]-2-trifluoromethyl-benzonitrile | 3.38 LC 532.01 [M − H]$^-$ | 2 |
| 29 | ![3-sulfonamide-phenyl] | 3-[4-(4-Cyano-3-trifluoromethyl-phenyl)-1,7-dimethyl-3,5-dioxo-11-oxa-4,9-diaza-tricyclo[5.3.1.0$^{2,6}$]undec-9-yl]-benzenesulfonamide | 3.25 LC 533.01 [M − H]$^-$ | 2 |
| 30 | ![3-carboxamide-phenyl] | 3-[4-(4-Cyano-3-trifluoromethyl-phenyl)-1,7-dimethyl-3,5-dioxo-11-oxa-4,9-diaza-tricyclo[5.3.1.0$^{2,6}$]undec-9-yl]-benzamide | 3.29 LC 499.1588 [M + H]$^+$ | 3 |
| 31 | ![4-bromo-2-trifluoromethyl-phenyl] | 4-[9-(4-Bromo-3-trifluoromethyl-phenyl)-1,7-dimethyl-3,5-dioxo-11-oxa-4,9-diaza-tricyclo[5.3.1.0$^{2,6}$]undec-4-yl]-2-trifluoromethyl-benzonitrile | 4.09 LC 600.0337 [M − H]$^-$ | 3 |

TABLE 1-continued

| Ex. No. | G | Compound Name | Retention Time Min. | Procedure of Example |
|---|---|---|---|---|
| 32 | 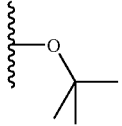 | 4-(9-tert-Butoxy-1,7-dimethyl-3,5-dioxo-11-oxa-4,9-diaza-tricyclo[5.3.1.0$^{2,6}$]undec-4-yl)-2-trifluoromethyl-benzonitrile | 3.70 LC 452.30 [M + H]$^+$ | 3 |
| 33 | 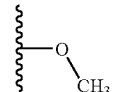 | 4-(9-Methoxy-1,7-dimethyl-3,5-dioxo-11-oxa-4,9-diaza-tricyclo[5.3.1.0$^{2,6}$]undec-4-yl)-2-trifluoromethyl-benzonitrile | 3.25 LC 410.24 [M + H]$^+$ | 3 |
| 34 | 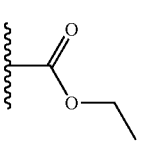 | 4-(4-Cyano-3-trifluoromethyl-phenyl)-1,7-dimethyl-3,5-dioxo-11-oxa-4,9-diaza-tricyclo[5.3.1.0$^{2,6}$]undecane-9-carboxylic acid ethyl ester | 3.33 LC 450.1291 [M − H]$^-$ | 11 |
| 35 | 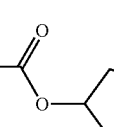 | 4-(4-Cyano-3-trifluoromethyl-phenyl)-1,7-dimethyl-3,5-dioxo-11-oxa-4,9-diaza-tricyclo[5.3.1.0$^{2,6}$]undecane-9-carboxylic acid cyclopentyl ester | 3.66 LC 490.07 [M − H]$^-$ | 11 |
| 36 | 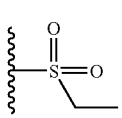 | 4-(9-Ethanesulfonyl-1,7-dimethyl-3,5-dioxo-11-oxa-4,9-diaza-tricyclo[5.3.1.0$^{2,6}$]undec-4-yl)-2-trifluoromethyl-benzonitrile | 3.05 LC 489.1424 [M + NH$_4$]$^+$ | 12 |
| 37 | 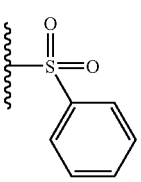 | 4-(9-Benzenesulfonyl-1,7-dimethyl-3,5-dioxo-11-oxa-4,9-diaza-tricyclo[5.3.1.0$^{2,6}$]undec-4-yl)-2-trifluoromethyl-benzonitrile | 3.47 LC 537.1415 [M + NH$_4$]$^+$ | 12 |
| 38 | 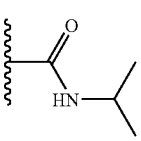 | 4-(4-Cyano-3-trifluoromethyl-phenyl)-1,7-dimethyl-3,5-dioxo-11-oxa-4,9-diaza-tricyclo[5.3.1.0$^{2,6}$]undecane-9-carboxylic acid isopropylamide | 3.19 LC 456.1759 [M + H]$^+$ | 13 |
| 39 | 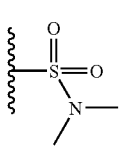 | 4-(4-Cyano-3-trifluoromethyl-phenyl)-1,7-dimethyl-3,5-dioxo-11-oxa-4,9-diaza-tricyclo[5.3.1.0$^{2,6}$]undecane-9-sulfonic acid dimethylamide | 3.19 LC 504.1548 [M + NH$_4$]$^+$ | 12 |
| 40 | 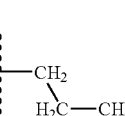 | 4-(1,7-Dimethyl-3,5-dioxo-9-propyl-11-oxa-4,9-diaza-tricyclo[5.3.1.0$^{2,6}$]undec-4-yl)-2-trifluoromethyl-benzonitrile | 2.34 LC 422.1696 [M + H]$^+$ | 76 |
| 41 | 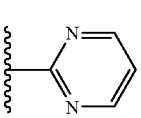 | 4-(1,7-Dimethyl-3,5-dioxo-9-pyrimidin-2-yl-11-oxa-4,9-diaza-tricyclo[5.3.1.0$^{2,6}$]undec-4-yl)-2-trifluoromethyl-benzonitrile | 3.36 LC 458.1440 [M + H]$^+$ | 8 |
| 42 | 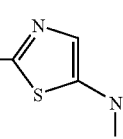 | 4-[1,7-Dimethyl-9-(5-nitro-thiazol-2-yl)-3,5-dioxo-11-oxa-4,9-diaza-tricyclo[5.3.1.0$^{2,6}$]undec-4-yl]-2-trifluoromethyl-benzonitrile | 3.37 LC 505.98 [M − H]$^-$ | 8 |

TABLE 1-continued

| Ex. No. | G | Compound Name | Retention Time Min. | Procedure of Example |
|---|---|---|---|---|
| 43 | 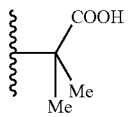 | 2-[4-(4-Cyano-3-trifluoromethyl-phenyl)-1,7-dimethyl-3,5-dioxo-11-oxa-4,9-diaza-tricyclo[5.3.1.0$^{2,6}$]undec-9-yl]-2-methyl-propionic acid | 3.27 LC 464.1433 [M − H]$^-$ | 9 |
| 44 | 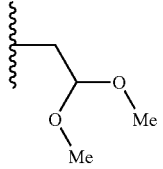 | 4-[9-(2,2-Dimethoxy-ethyl)-1,7-dimethyl-3,5-dioxo-11-oxa-4,9-diaza-tricyclo[5.3.1.0$^{2,6}$]undec-4-yl]-2-trifluoromethyl-benzonitrile | 3.20 LC 468.1766 [M + H]$^+$ | 6 |
| 45 | 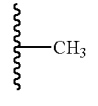 | 2-Trifluoromethyl-4-(1,7,9-trimethyl-3,5,8,10-tetraoxo-11-oxa-4,9-diaza-tricyclo[5.3.1.0$^{2,6}$]undec-4-yl)-benzonitrile | 3.45 LC 419.96 [M − H]$^-$ | 6 |
| 46 | 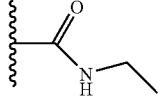 | | 12.577 LC 451.2 [M + H]$^+$ | 12 |
| 47 | 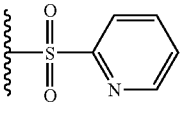 | | 14.484 LC 521.1 [M + H]$^+$ | 12 |
| 48 | 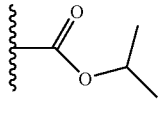 | | 15.350 LC 466.0 [M + H]$^+$ | 11 |
| 49 | 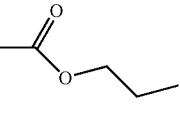 | | 15.350 LC 466.2 [M + H]$^+$ | 11 |
| 50 | 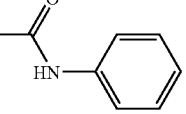 | | 14.498 LC 499.2 [M + H]$^+$ | 13 |
| 51 | 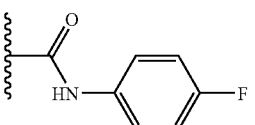 | | 14.642 LC 517.1 [M + H]$^+$ | 13 |
| 52 | 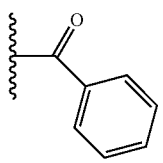 | | 14.441 LC 484.2 [M + H]$^+$ | 4 |
| 53 | 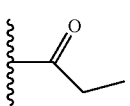 | | 13.097 LC 436.2 [M + H]$^+$ | 4 |

TABLE 1-continued

| Ex. No. | G | Compound Name | Retention Time Min. | Procedure of Example |
|---|---|---|---|---|
| 54 | (cyclopropyl ketone) | | 13.504 LC 448.1 [M + H]+ | 4 |
| 55 | (sulfonyl-ethyl-pyridine) | | 12.311 LC 549.1 [M + H]+ | 12 |
| 56 | (sulfonyl-dimethylisoxazole) | | 15.367 LC 539.1 [M + H]+ | 12 |
| 57 | (methylsulfonyl) | | 13.425 LC 458.0 [M + H]+ | 12 |
| 58 | (4-fluorophenylsulfonyl) | | 15.876 LC 538.0 [M + H]+ | 12 |
| 59 | (sulfonyl-ethyl-diethylamine) | | 12.585 LC 543.2 [M + H]+ | 12 |
| 60 | (ester-ethyl-tosylsulfonyl) | | 15.180 LC 606.1 [M + H]+ | 11 |

EXAMPLES 61 to 76

Examples 61 to 76 were prepared according to the general procedure indicated in Table 2 and had the general formula represented by

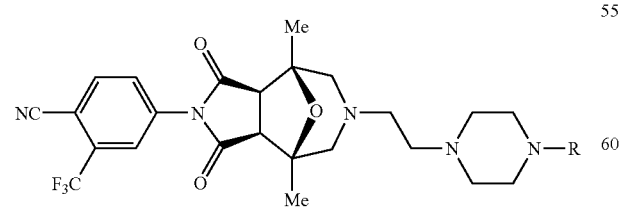

wherein R is defined in Table 2. Examples 61 to 76 were evaluated by HPLC method C.

TABLE 2

| Ex. No. | R | Retention Time Min. | Procedure of Example |
|---|---|---|---|
| 61 | (3-fluorophenylsulfonyl) | 14.118 LC 650.3 [M + H]+ | 20 |
| 62 | (isopropylsulfonyl) | 13.041 LC 598.1 [M + H]+ | 20 |

TABLE 2-continued

| Ex. No. | R | Retention Time Min. | Procedure of Example |
|---|---|---|---|
| 63 | (ethylsulfonyl) | 12.632 LC 584.2 [M + H]+ | 20 |
| 64 | (CF3-CH2-sulfonyl) | 13.762 LC 638.1 [M + H]+ | 20 |
| 65 | (ethyl ester) | 12.559 LC 564.3 [M + H]+ | 18 |
| 66 | (isopropyl ester) | 13.252 LC 578.3 [M + H]+ | 18 |
| 67 | (isobutyryl) | 12.306 LC 562.1 [M + H]+ | 19 |
| 68 | (4-cyanobenzoyl) | 12.786 LC 621.2 [M + H]+ | 19 |
| 69 | (2-methoxybenzoyl) | 12.954 LC 626.4 [M + H]+ | 19 |
| 70 | (N-ethyl amide) | 11.74 LC 563.1 [M + H]+ | 21 |
| 71 | (N-isopropyl amide) | 12.076 LC 577.4 [M + H]+ | 21 |
| 72 | (4-dimethylamino-phenyl amide) | 11.200 LC 654.3 [M + H]+ | 21 |
| 73 | (2,6-dichloropyridin-4-yl amide) | 13.939 LC 680.2 [M + H]+ | 21 |
| 74 | (2,2,2-trifluoroethyl ester) | 14.285 LC 668.2 [M + H]+ | 18 |
| 75 | (trifluoroacetonyl) | 12.752 LC 602.2 [M + H]+ | 19 |
| 76 | (4-cyanophenylsulfonyl) | 13.837 LC 657.2 [M + H]+ | 20 |

EXAMPLES 77 to 144

Examples 77 to 144 were prepared according to the general procedure indicated in Table 3 and had the general formula represented by

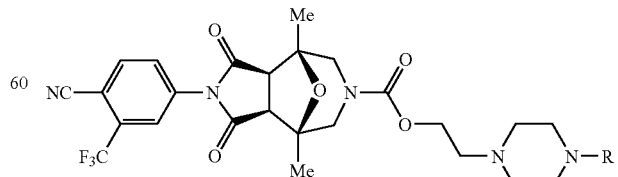

wherein R is defined in Table 3.

TABLE 3
| Ex. No. | R | Retention Time Min. | HPLC Method | Procedure of Example |
|---|---|---|---|---|
| 77 | 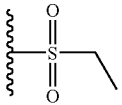 | 1.38 LC 628.23 [M + H]+ | B | 20 |
| 78 | 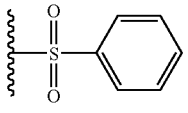 | 1.44 LC 676.23 [M + H]+ | B | 20 |
| 79 | 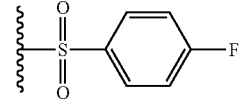 | 1.50 LC 694.22 [M + H]+ | B | 20 |
| 80 | 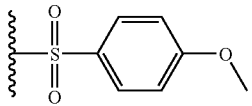 | 1.48 LC 706.23 [M + H]+ | B | 20 |
| 81 | 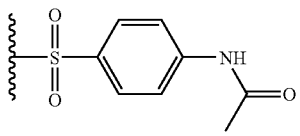 | 1.47 LC 733.4 [M + H]+ | B | 20 |
| 82 | 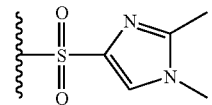 | 1.30 LC 694.4 [M + H]+ | B | 20 |
| 83 | 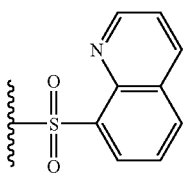 | 1.48 LC 727.4 [M + H]+ | B | 20 |
| 84 | 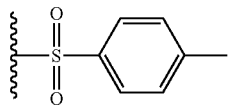 | 1.50 LC 690.4 [M + H]+ | B | 20 |
| 85 | 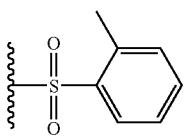 | 1.53 LC 690.4 [M + H]+ | B | 20 |
| 86 | 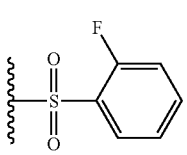 | 1.46 LC 694.4 [M + H]+ | B | 20 |
| 87 | 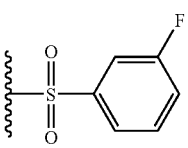 | 1.51 LC 694.4 [M + H]+ | B | 20 |

TABLE 3-continued

| Ex. No. | R | Retention Time Min. | HPLC Method | Procedure of Example |
|---|---|---|---|---|
| 88 | (sulfonyl-2-CF₃-phenyl) | 1.53 LC 744.4 [M + H]⁺ | B | 20 |
| 89 | (sulfonyl-3-methyl-phenyl) | 1.51 LC 690.4 [M + H]⁺ | B | 20 |
| 90 | (sulfonyl-3,4-dimethoxy-phenyl) | 1.43 LC 736.4 [M + H]⁺ | B | 20 |
| 91 | (sulfonyl-4-CN-phenyl) | 1.41 LC 701.4 [M + H]⁺ | B | 20 |
| 92 | (sulfonyl-3,5-dimethylisoxazol-4-yl) | 1.47 LC 695.4 [M + H]⁺ | B | 20 |
| 93 | (sulfonyl-2-Cl-4-F-phenyl) | 1.54 LC 728.4 [M + H]⁺ | B | 20 |
| 94 | (sulfonyl-3,4-difluoro-phenyl) | 1.55 LC 712.4 [M + H]⁺ | B | 20 |
| 95 | (sulfonyl-3-CN-phenyl) | 1.47 LC 701.4 [M + H]⁺ | B | 20 |
| 96 | (sulfonyl-3-OMe-phenyl) | 1.50 LC 706.4 [M + H]⁺ | B | 20 |

TABLE 3-continued

| Ex. No. | R | Retention Time Min. | HPLC Method | Procedure of Example |
|---|---|---|---|---|
| 97 | sulfonyl-naphthalen-1-yl | 1.60 LC 726.4 [M + H]+ | B | 20 |
| 98 | sulfonyl-naphthalen-2-yl | 1.62 LC 726.4 [M + H]+ | B | 20 |
| 99 | sulfonyl-(3-trifluoromethyl)phenyl | 1.68 LC 744.4 [M + H]+ | B | 20 |
| 100 | sulfonyl-(3-chloro-4-fluoro)phenyl | 1.63 LC 728.4 [M + H]+ | B | 20 |
| 101 | sulfonyl-(2,4-dichloro)phenyl | 1.68 LC 744.3 [M + H]+ | B | 20 |
| 102 | sulfonyl-(4-tert-butyl)phenyl | 1.82 LC 732.5 [M + H]+ | B | 20 |
| 103 | sulfonyl-(3,5-dichloro)phenyl | 1.85 LC 744.3 [M + H]+ | B | 20 |
| 104 | sulfonyl-(4-phenoxy)phenyl | 1.76 LC 768.4 [M + H]+ | B | 20 |
| 105 | C(O)NH-(2-phenyl)cyclopropyl | 1.67 LC 695.3 [M + H]+ | B | 21 |

TABLE 3-continued
| Ex. No. | R | Retention Time Min. | HPLC Method | Procedure of Example |
|---|---|---|---|---|
| 106 | 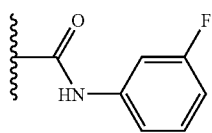 | 1.58 LC 673.2 [M + H]⁺ | B | 21 |
| 107 | 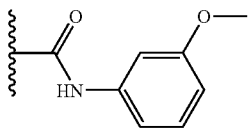 | 1.54 LC 685.3 [M + H]⁺ | B | 21 |
| 108 | 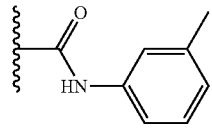 | 1.60 LC 669.3 [M + H]⁺ | B | 21 |
| 109 | 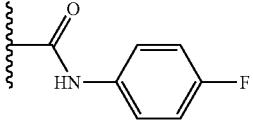 | 1.55 LC 673.2 [M + H]⁺ | B | 21 |
| 110 | 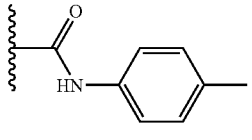 | 1.61 LC 669.2 [M + H]⁺ | B | 21 |
| 111 | 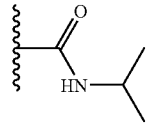 | 1.43 LC 621.2 [M + H]⁺ | B | 21 |
| 112 | 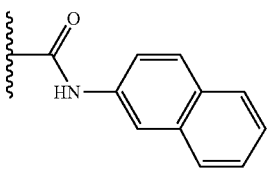 | 1.72 LC 705.2 [M + H]⁺ | B | 21 |
| 113 | 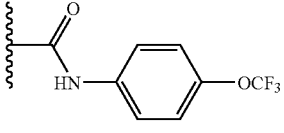 | 1.76 LC 739.3 [M + H]⁺ | B | 21 |
| 114 | 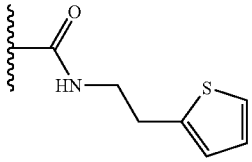 | 1.57 LC 689.2 [M + H]⁺ | B | 21 |

TABLE 3-continued

| Ex. No. | R | Retention Time Min. | HPLC Method | Procedure of Example |
|---|---|---|---|---|
| 115 | (R)-1-phenylethyl amide | 1.62 LC 683.2 [M + H]+ | B | 21 |
| 116 | (R)-1-(naphthalen-1-yl)ethyl amide | 1.72 LC 733.2 [M + H]+ | B | 21 |
| 117 | 4-fluorobenzyl amide | 1.59 LC 687.2 [M + H]+ | B | 21 |
| 118 | 4-methoxybenzyl amide | 1.59 LC 699.2 [M + H]+ | B | 21 |
| 119 | 3-fluorobenzyl amide | 1.59 LC 687.2 [M + H]+ | B | 21 |
| 120 | cyclopentyl amide | 1.54 LC 647.2 [M + H]+ | B | 21 |
| 121 | 3-cyanophenyl amide | 1.52 LC 680.2 [M + H]+ | B | 21 |

TABLE 3-continued
| Ex. No. | R | Retention Time Min. | HPLC Method | Procedure of Example |
|---|---|---|---|---|
| 122 | 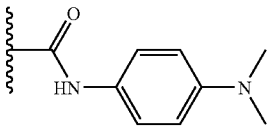 | 1.28 LC 698.3 [M + H]+ | B | 21 |
| 123 | 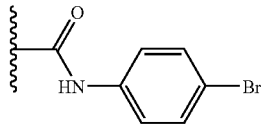 | 1.35 LC 733.3 [M + H]+ | B | 21 |
| 124 | 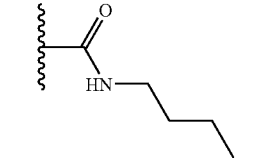 | 1.26 LC 635.2 [M + H]+ | B | 21 |
| 125 | 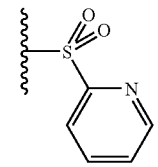 | LC [M + H]+ | A | 20 |
| 126 | 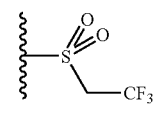 | LC [M + H]+ | A | 20 |
| 127 | 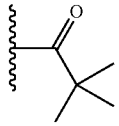 | 2.47 LC 620.3 [M + H]+ | B | 14 |
| 128 | 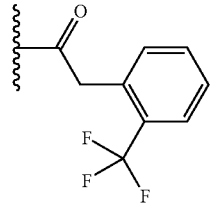 | 2.49 LC 722.3 [M + H]+ | B | 14 |
| 129 | 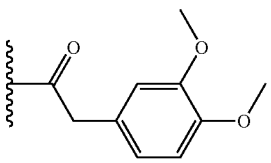 | 2.28 LC 714.3 [M + H]+ | B | 14 |
| 130 | 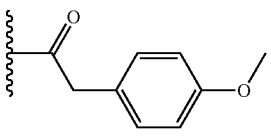 | 2.53 LC 684.3 [M + H]+ | B | 14 |

TABLE 3-continued
| Ex. No. | R | Retention Time Min. | HPLC Method | Procedure of Example |
|---|---|---|---|---|
| 131 | 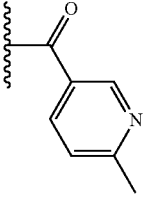 | 2.02 LC 655.3 [M + H]+ | B | 14 |
| 132 | 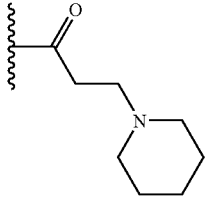 | 2.00 LC 675.3 [M + H]+ | B | 14 |
| 133 | 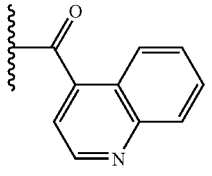 | 2.19 LC 691.3 [M + H]+ | B | 14 |
| 134 | 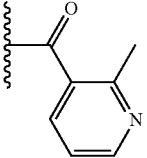 | 2.17 LC 655.3 [M + H]+ | B | 14 |
| 135 | 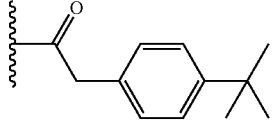 | 2.74 LC 710.3 [M + H]+ | B | 14 |
| 136 | 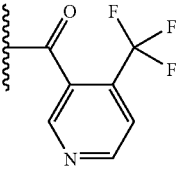 | 2.29 LC 709.2 [M + H]+ | B | 14 |
| 137 | 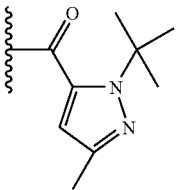 | 2.42 LC 709.2 [M + H]+ | B | 14 |
| 138 | 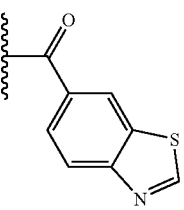 | 2.23 LC 697.2 [M + H]+ | B | 14 |

TABLE 3-continued

| Ex. No. | R | Retention Time Min. | HPLC Method | Procedure of Example |
|---|---|---|---|---|
| 139 | (structure with CF3 and ketone) | 2.25 LC 646.2 [M + H]+ | B | 14 |
| 140 | (pyridyl-CF3 ketone) | 2.42 LC 709.2 [M + H]+ | B | 14 |
| 141 | (cyclopentyl ketone) | 1.33 LC 631.3 [M + H]+ | B | 14 |
| 142 | (4-CF3-phenyl acetone) | 1.45 LC 721.2 [M + H]+ | B | 14 |
| 143 | (quinoline-3-carbonyl) | 1.27 LC 690.2 [M + H]+ | B | 14 |
| 144 | (2,4-dimethylthiazole-5-carbonyl) | 1.25 LC 674.2 [M + H]+ | B | 14 |

Example 145

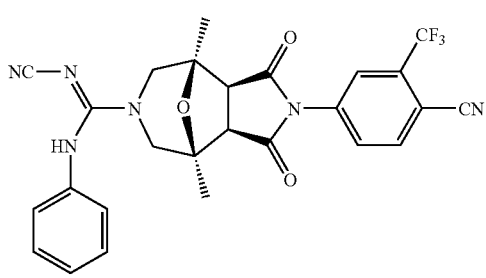

To a stirred solution of Example 3 (50 mg; 0.13 mmol) in 1.0 mL dry DMF 5 at ambient temperature was added 1-cyano-3-phenylthiourea (0.034 g, 0.17 mmol) and EDCl (0.033 g, 0.17 mmol)). The resulting cloudy mixture was stirred overnight under nitrogen at 22° C. The mixture was then partitioned between ethyl acetate and 1M citric acid (in pyridyl case, water was used). The aqueous layer was extracted with 5 mL EtOAc three times. The organics were combined, washed with excess amounts of brine to remove DMF, dried over magnesium sulfate, filtered, and concentrated affording a pale yellow oil. The crude material was purified by flash chromatography (5-25% acetone/$CH_2Cl_2$) to give Example 145 (0.037 g) as a white solid. 96% at 3.318 min (retention time) (YMC ODS-A column 4.6×50 mm eluting with 10-90% aqueous methanol over 4 minutes containing 0.1% $H_3PO_4$, 4 mL/min, monitoring at 220 nm). MS (ES): m/z 523.1 [M+H]+.

PREPARATION 8

(2-Chloro-N-(4-fluorobenzyl)acetamide)

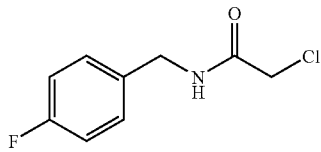

To a dry, nitrogen purged 25 mL round bottomed flask equipped with a magnetic stir bar was added 4-chlorobenzylamine (111 mg, 0.887 mmol), anhydrous $CH_2Cl_2$ (2 mL), and chloroacetyl chloride (111 mg, 0.979 mmol). The resulting solution was cooled to 0° C. and triethylamine (109 mg, 1.08 mmol) was added slowly via syringe. The resulting dark brown mixture was stirred at 0° C. for 15 min then warmed to rt and stirred for an additional 15 h. After this time, the reaction mixture was concentrated and the resulting residue loaded directly onto a silica gel column eluting with 20% EtOAc in hexanes. Subsequent concentration of the product containing fractions afforded 148 mg (83%) of Preparation 8 as an off-white solid. $R_f$=0.37 ($SiO_2$, 5% MeOH in $CH_2Cl_2$). HPLC (method C): $R_t$=10.6 min. $^1$H NMR (500 MHz, $CDCl_3$): δ=7.27 (m, 2H), 7.04 (m, 2H), 6.86 (br s, 1H), 4.46 (d, J=5.9 Hz, 2H) and 4.11 (s, 2H). m/z=202 [M+H]$^+$.

PREPARATION 9

2-Chloro-N-4-chlorobenzyl)acetamide

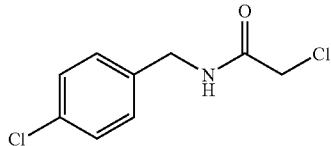

Preparation 9 was prepared in identical fashion to Preparation 8 and was obtained as an off-white solid in 65% yield. $R_f$=0.67 ($SiO_2$, 50% EtOAc in hexanes). HPLC (method C): $R_t$=11.8 min. $^1$H NMR (500 MHz, $CDCl_3$): δ=7.32 (d, J=8.3 Hz, 2H), 7.23 (d, J=8.3 Hz, 2H), 6.86 (br s, 1H), 4.46 (d, J=5.9 Hz, 2H) and 4.11 (s, 2H). m/z=218 [M+H]$^+$.

PREPARATION 10

2-Chloro-N-(4-methoxybenzyl)acetamide

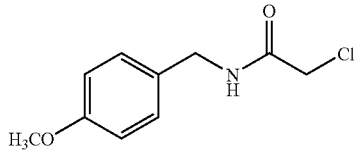

Preparation 10 was prepared in identical fashion to Preparation 8 and was obtained as an off-white solid in 82% yield. $R_f$=0.67 ($SiO_2$, 5% MeOH in $CH_2Cl_2$). HPLC (method C): $R_t$=10.4 min. $^1$H NMR (500 MHz, $CDCl_3$): δ=7.22 (d, J=8.6 Hz, 2H), 6.88 (d, J=8.6 Hz, 2H), 6.78 (br s, 1H), 4.42 (d, J=5.7 Hz, 2H), 4.09 (s, 2H) and 3.80 (s, 3H). m/z=214 [M+H]$^+$.

PREPARATION 11

2-Chloro-N-(4-nitrobenzyl)acetamide

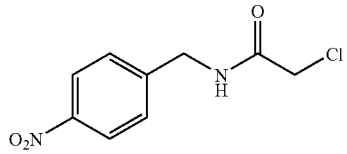

Preparation 11 was prepared in identical fashion to Preparation 8 and was obtained as an off-white solid in 91% yield. $R_f$=0.40 ($SiO_2$, 40% EtOAc in hexanes). HPLC (method C): $R_t$=10.6 min. $^1$H NMR (500 MHz, $CDCl_3$): δ=8.21 (d, J=8.6 Hz, 2H), 7.46 (d, J=8.6 Hz, 2H), 7.04 (br s, 1H), 4.61 (d, J.=6.1 Hz, 2H) and 4.14 (s, 2H). m/z=229 [M+H]$^+$.

EXAMPLE 146

2-[4-(4-Cyano-3-trifluoromethylphenyl)-1,7-dimethyl-3,5-dioxo-11-oxa-4,9-diazatricyclo[5.3.1.0$^{2,6}$] undec-9-yl]-N-(4-nitrobenzyl)acetamide

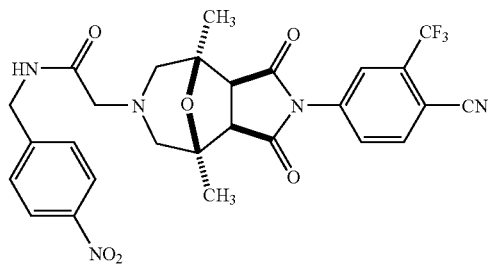

To a dry, nitrogen purged 25 mL round bottomed flask equipped with a magnetic stir bar was added Example 3 (75 mg, 0.198 mmol), Preparation 10 (91.0 mg, 0.398 mmol), anhydrous N,N-dimethylformamide (3 mL), and sodium iodide (30.0 mg, 0.200 mmol). The resulting mixture was heated to 100° C. for 15 h then cooled and concentrated. The resulting crude material was then purified by preparative HPLC. Concentration of the product containing fractions afforded 71.9 mg (64%) of Example 146 as a light yellow solid. $R_f$=0.50 ($SiO_2$, 45% MeOH in $CH_2Cl_2$). HPLC (method C): $R_t$=14.2 min. $^1$H NMR (500 MHz, $CDCl_3$): δ=8.20 (d, J=8.7 Hz, 2H), 7.94 (d, J=8.3 Hz, 1H), 7.84 (d, J=1.9 Hz, 1H), 7.73 (dd, J=8.3 and 1.9 Hz, 1H), 7.44 (d, J=8.7 Hz, 2H), 6.81 (m, 1H), 4.60 (d, J=6.2 Hz, 2H), 3.33 (s, 2H), 3.17 (s, 2H), 2.80 (d, J=11.6 Hz, 2H), 2.34 (d, J=11.6 Hz, 2H) and 1.45 (s, 6H). m/z=572 [M+H]$^+$.

Example 147

N-(4-Aminobenzyl)-2-[4-(4-cyano-3-trifluoromethylphenyl)-1,7-dimethyl-3,5-dioxo-11-oxa4,9-diazatricyclo[5.3.1.0$^{2,6}$]undec-9-yl]acetamide

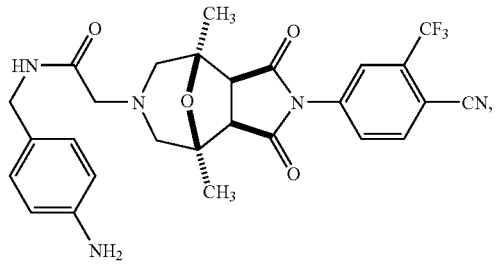

To a dry, nitrogen purged 25 mL round bottomed flask with a magnetic stirring bar was added Example 146 (70.0 mg, 0.122 mmol), EtOAc (3 mL), and concentrated HCl (1.5 mL). The solution was stirred vigorously and iron powder (42.0 mg, 0.752 mmol) was added all at once. After stirring 3 days at rt the reaction mixture was basified with saturated aq. Na₂CO₃ to pH 8. The aqueous layer was separated, extracted with EtOAc (3×30 mL), and the combined EtOAc layers dried over Na₂SO₄ and filtered. After concentrating, the crude material was loaded onto a silica gel column, eluting with 70-90% EtOAc in hexanes. Subsequent concentration of the product containing fractions afforded 56.5 mg (85%) of Example 147 as a light orange solid. $R_f$=0.45 (SiO₂, 80% EtOAc in hexanes). HPLC (method C): $R_t$=11.4 min. ¹H NMR (500 MHz, CDCl₃): δ=7.93 (d, J=8.3 Hz, 1H), 7.86 (d, J=1.8 Hz, 1H), 7.73 (dd, J=8.3 and 1.8 Hz, 1H), 7.06 (d, J=8.3 Hz, 2H), 6.66 (d, J=8.3 Hz, 2H), 6.51 (m, 1H), 4.34 (d, J=5.5 Hz, 2H), 3.70 (s, 2H), 3.15 (s, 2H), 3.07 (s, 2H), 2.71 (d, J=11.5 Hz, 2H), 2.27 (d, J=11.5 Hz, 2H) and 1.41 (s, 6H). m/z=542 [M+H]⁺.

Example 148

4-{1,7-Dimethyl-9-[2-(4-nitrophenoxy)-ethyl]-3,5-dioxo-11-oxa-4,9-diazatricyclo[5.3.1.0²,⁶]undec-4-yl}-2-trifluoromethylbenzonitrile

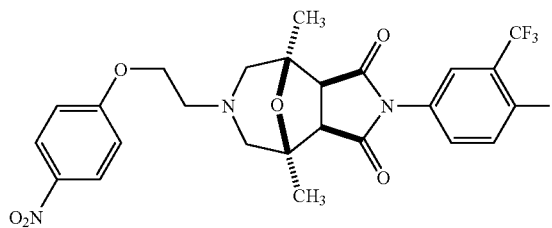

To a dry, nitrogen purged 25 mL round bottomed flask equipped with a magnetic stir bar was added Example 3 (2.00 g, 5.27 mmol), 1-(2-chloroethoxy)-4-nitrobenzene (2.14 g, 10.6 mmol), anhydrous N,N-dimethylformamide (40 mL) and sodium iodide (790 mg, 5.27 mmol). The resulting mixture was heated at 100° C. for 3 days, cooled to rt and purified by silica gel chromatography, eluting with 50% EtOAc in hexanes, to afford 1.39 g (48%) of Example 148 as an off-white solid. $R_f$=0.28 (SiO₂, 50% EtOAc in hexanes). HPLC (method C): $R_t$=15.1 min. ¹H NMR (500 MHz, CDCl₃): δ=8.21 (d, J=9.2 Hz, 2H), 7.93 (d, J=8.6 Hz, 1H), 7.86 (d, J=1.8 Hz, 1H), 7.75 (dd, J=8.6 and 1.8 Hz, 1H), 6.95 (d, J=9.2 Hz, 2H), 4.17 (t, J=5.3 Hz, 2H), 3.40 (s, 2H), 2.90 (t, J=5.3 Hz, 2H), 2.84 (d, J=11.3 Hz, 2H), 2.33 (d, J=11.3 Hz, 2H) and 1.46 (s, 6H). m/z=545 [M+H]⁺.

Example 149

4-{9-[2-(4-Aminophenoxy)ethyl]-1,7-dimethyl-3,5-dioxo-11-oxa-4,9-diazatricyclo[5.3.1.0²,⁶]undec4-yl}-2-trifluoromethylbenzonitrile

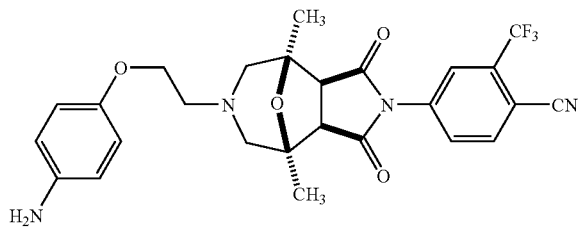

To a dry, nitrogen purged 25 mL round bottomed flask equipped with a magnetic stir bar was added Example 148 (1.39 g, 2.55 mmol), EtOAc (20 mL) and concentrated HCl (2.0 mL). The solution was stirred vigorously and iron powder (855 mg, 15.3 mmol) was added in one portion. After stirring for 15 h at rt the reaction mixture was basified with saturated aq. Na₂CO₃ to pH 9. The aqueous layer was extracted with EtOAc (3×50 mL) and the EtOAc layers were dried over Na₂SO₄ and filtered. After concentrating, the crude material was purified by silica gel chromatography, eluting with 60% EtOAc in hexanes, to afford 978 mg (75%) of Example 149 as a light yellow solid. $R_f$=0.38 (SiO₂, 50% EtOAc in hexanes). HPLC (mehtod C): $R_t$=11.3 min. ¹H NMR (500 MHz, CDCl₃): δ=7.93 (d, J=8.3 Hz, 1H), 7.87 (d, J=1.7 Hz, 1H), 7.75 (dd, J=8.3 and 1.7 Hz, 1H), 6.73 (d, J=8.8 Hz, 2H), 6.64 (d, J=8.8 Hz, 2H), 4.00 (t, J=5.3 Hz, 2H), 3.44 (s, 2H), 3.37 (s, 2H), 2.80 (m, 4H), 2.28 (d, J=11.4 Hz, 2H) and 1.43 (s, 6H). m/z=515 [M+H]⁺.

Example 150

N-(4-{2-[4-(4-Cyano-3-trifluoromethylphenyl)-1,7-dimethyl-3,5-dioxo-11-oxa-4,9-diazatricyclo[5.3.1.0²,⁶]undec-9-yl]-ethoxy}phenyl)acetamide

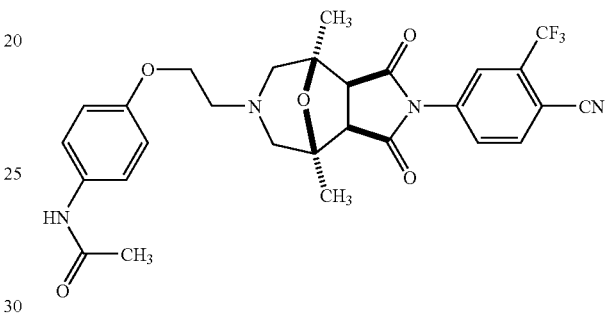

To a dry, nitrogen purged 25 mL round bottomed flask equipped with magnetic stir bar was added Example 149 (0.042 g, 0.081 mmol), anhydrous CH₂Cl₂ (2 mL), triethylamine (0.009 g, 0.093 mmol) and acetic anhydride (0.009 g, 0.085 mmol). The mixture was stirred at rt for 2 h then purified by preparative HPLC. After combining and concentrating the product containing fractions, 0.039 g (87%) of Example 150 was obtained as a white solid. $R_f$=0.44 (SiO₂, 5% MeOH in CH₂Cl₂). HPLC (method C): $R_t$=12.4 min. ¹H NMR (500 MHz, CDCl₃): δ=7.92 (d, J=8.3 Hz, 1H), 7.89 (d, J=1.8 Hz, 1H), 7.74 (dd, J=8.3 and 1.8 Hz, 1H), 7.37 (d, J=8.9 Hz, 2H), 7.04 (s, 1H), 6.86 (d, J=8.9 Hz, 2H), 4.07 (t, J=5.1 Hz, 2H), 3.27 (s, 2H), 2.81 (m, 4H), 2.26 (d, J=11.3 Hz, 2H), 2.13 (s, 3H) and 1.42 (s, 6H). m/z=557 [M+H]⁺.

Example 151

Preparation of (4-{2-[4-(4-Cyano-3-trifluoromethylphenyl)-1,7-dimethyl-3,5-dioxo-11-oxa4,9-diazatricyclo[5.3.1.0²,⁶]undec-9-yl]ethoxy}phenyl)ethanesulfonamide

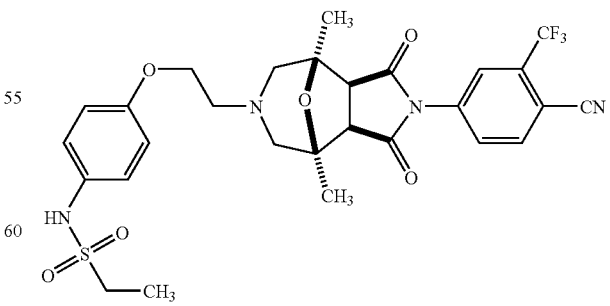

To a dry, nitrogen purged two dram amber vial equipped with a magnetic stir bar was added Example 149 (0.075 g, 145 mmol), triethylamine (0.022 g, 1.568 mmol) and dry CH₂Cl₂ (2 mL). The solution was stirred at rt and ethanesulfonyl chloride (0.028 g, 0.218 mmol) added slowly via syringe. The reaction was stirred at rt for 7 days then concentrated and the residue purified by preparative HPLC. Concentration of the product containing fractions afforded 43.1 mg (49%) of Example 151 as a white solid. $R_f$=0.44 (SiO$_2$, 70% EtOAc in hexanes). HPLC (method C): $R_t$=13.3 min. $^1$H NMR (500 MHz, CDCl$_3$): δ=7.93 (d, J=8.3 Hz, 1H), 7.86 (d, J=1.8 Hz, 1H), 7.75 (dd, J=8.3 and 1.8 Hz, 1H), 7.18 (d, J=8.9 Hz, 2H), 6.87 (d, J=8.9 Hz, 2H), 6.12 (s, 1H), 4.06 (t, J=5.2 Hz, 2H), 3.33 (s, 2H), 3.06 (m, 2H), 2.82 (m, 4H), 2.29 (d, J=11.3 Hz, 2H), 1.54 (s, 3H), 1.44 (s, 3H) and 1.38 (t, J=7.3 Hz, 3H). m/z=607 [M+H]$^+$.

Example 152

Preparation of Ethyl (4-{2-[4-(4-cyano-3-trifluoromethylphenyl)-1,7-dimethyl-3,5-dioxo-11-oxa4,9-diazatricyclo[5.3.1.0$^{2,6}$]undec-9-yl]ethoxy}phenyl)carbamate

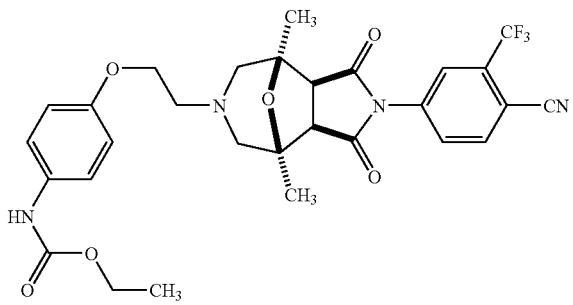

To a dry, nitrogen purged two dram amber vial equipped with a magnetic stir bar was added Example 149 (0.035 g, 68.03 mmol), triethylamine (8.71 mg, 86.1 mmol) and dry CH$_2$Cl$_2$ (2 mL). The solution was stirred at rt and ethyl chloroformate (9.08 mg, 83.7 mmol) added slowly via syringe. The reaction was stirred for 7 days at rt then concentrated and the residue purified by preparative HPLC. Concentration of the product containing fractions afforded 22.5 mg (56%) of Example 152 as a white solid. $R_f$=0.69 (SiO$_2$, 70% EtOAc in hexanes). HPLC (method C): $R_t$=14.0 min. $^1$H NMR (500 MHz, CDCl$_3$): δ=7.92 (d, J=8.3 Hz, 1H), 7.87 (d, J=1.8 Hz, 1H), 7.75 (dd, J=8.3 and 1.8 Hz, 1H), 7.28 (m, 2H), 6.84 (d, J=8.9 Hz, 2H), 6.41 (m, 1H), 4.17 (m, 2H), 4.06 (t, J=5.2 Hz, 2H), 3.31 (s, 2H), 2.81 (m, 4H), 2.28 (d, J=11.3 Hz, 2H), 1.43 (s, 6H) and 1.28 (t, J=7.0 Hz, 3H). m/z=587 [M+H]$^+$.

Example 153

Preparation of 1-(4-{2-[4-(4-Cyano-3-trifluoromethylphenyl)-1,7-dimethyl-3,5-dioxo-11-oxa-4,9-diazatricyclo[5.3.1.0$^{2,6}$]undec-9-yl]ethoxy}phenyl)-3-ethylurea A two dram reaction vial equipped with a magnetic stir bar was charged with Example 149 (25.6 mg, 0.050 mmol) and THF (1.0 mL). Ethyl isocyanate (10 μL, 0.13 mmol) was added and the solution was then stirred for 15 h. The crude reaction mixture was then diluted with CH$_3$CN (3 mL) and purified by preparative HPLC, using a gradient from 10:90 CH$_3$CN/H$_2$O to 100% CH$_3$CN over 16 min, hold 2 min at 100% CH$_3$CN. Fractions containing product were concentrated and the resulting residue dissolved in CH$_2$Cl$_2$ (25 mL). The solution was dried over Na$_2$SO$_4$, filtered and concentrated to afford 23.2 mg (80%) of Example 153 as a white solid. $R_f$=0.62 (SiO$_2$, EtOAc). HPLC (Method C): $R_t$=12.7 min. $^1$H NMR (500 MHz, CDCl$_3$): δ=7.92 (d, J=8.3 Hz, 1H), 7.87 (d, J=1.6 Hz, 1H), 7.75 (dd, J=8.3 and 1.9 Hz, 1H), 7.19 (dd, J=8.9 and 2.0 Hz, 2H), 6.87 (m, 2H), 6.02 (s, 1H), 4.48 (m, 1H), 4.06 (t, J=5.2 Hz, 2H), 3.33 (s, 2H), 3.25 (m, 2H), 2.82 (m, 4H), 2.29 (d, J=11.3 Hz, 2H), 1.43 (s, 6H) and (t, J=7.2 Hz, 3H). m/z=586 [M+H]$^+$.

Example 154

4-{9-[3-(tert-Butyl-dimethylsilanyloxy)propyl]-1,7-dimethyl-3,5-dioxo-11-oxa4,9-diazatricyclo[5.3.1.0$^{2,6}$]undec-4-yl}-2-trifluoromethylbenzonitrile

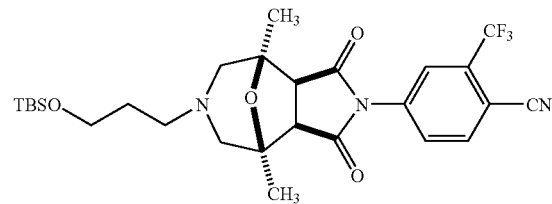

To a nitrogen purged 25 mL round bottomed flask was added Example 3 (50.0 mg, 0.132 mmol) and ethanol (6 mL). The solution was stirred and triethylamine (15.0 mg, 0.145 mmol), potassium iodide (22.0 mg, 0.132 mmol) and 3-(bromopropoxy)-tert-butyldimethylsilane (40.0 mg, 0.158 mmol) added. The reaction was heated at reflux for 5 days and cooled to rt. The solvent was removed under reduced pressure and the residue diluted with 30% EtOAc in hexanes (5 mL). After chromatography on silica gel eluting with 30% EtOAc in hexanes, 64.5 mg (89%) of Example 154 was obtained as an off-white solid. $R_f$=0.72 (SiO$_2$, 30% EtOAc in hexanes). HPLC (Method C): $R_t$=16.7 min. $^1$H NMR (500 MHz, CDCl$_3$): δ=7.94 (d, J=8.4 Hz, 1H), 7.88 (d, J=1.7 Hz, 1H), 7.76 (dd, J=8.3 Hz and 1.9 Hz, 1H) 3.65 (t, J=6.1 Hz, 2H), 3.38 (s, 2H), 2.75 (d, J=11.5 Hz, 2H), 2.45 (t, J=7.1 Hz, 2H), 2.09 (d, J=11.4 Hz, 2H), 1.67 (m, 2H), 1.44 (s, 6H), 0.90 (s, 9H) and 0.05 (s, 6H). m/z 552 [M+H]$^+$.

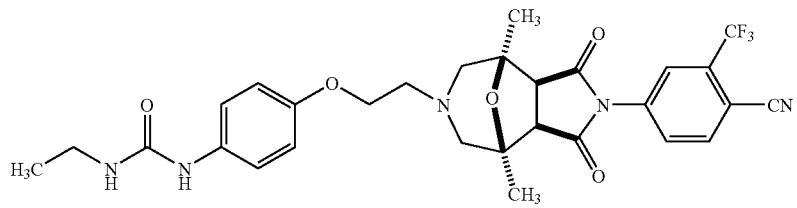

Example 155

4-[9-(3-Hydroxypropyl)-1,7-dimethyl-3,5-dioxo-11-oxa-4,9-diazatricyclo[5.3.1.0$^{2,6}$]undec-4-yl]-2-trifluoromethylbenzonitrile

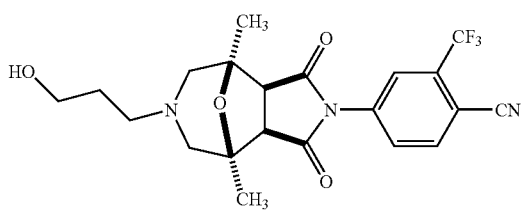

To a nitrogen purged 50 mL round bottomed flask with a magnetic stirrer was added Example 154 (64.5 mg, 0.117 mol) and ethanol (5 mL). The solution was stirred at rt and 3 drops of conc. HCl (30 μL) were added. The reaction was stirred at rt for 2 h then the solvent was removed under reduced pressure. Saturated aq. NaHCO$_3$ (5 mL) and EtOAc (5 mL) were added to the residue and the two-phase system was stirred vigorously for 15 min. The aqueous layer was separated, extracted with EtOAc (2×30 mL) and the combined EtOAc layers were dried over Na$_2$SO$_4$, filtered and concentrated to afford 47.5 mg (93%) of Example 155 as a tan solid. HPLC (Method C): R$_t$=11.1 min. $^1$H NMR (500 MHz, CDCl$_3$): δ=7.94 (d, J=8.4 Hz, 1H), 7.85 (d, J=1.7 Hz, 1H), 7.74 (dd, J=8.3 Hz and 1.9 Hz, 1H), 3.78 (t, J=5.6 Hz, 2H), 3.52 (br s, 1H), 3.36 (s, 2H), 2.92 (d, J=11.5 Hz, 2H), 2.63 (t, J=6.1 Hz, 2H), 2.11 (d, J=11.4 Hz, 2H), 1.75 (m, 2H) and 1.45 (s, 6H). m/z 438 [M+H]$^+$.

Example 156

4-[9-(3-Bromopropyl)-1,7-dimethyl-3,5-dioxo-11-oxa4,9-diazatricyclo[5.3.1.0$^{2,6}$]undec-4-yl]-2-trifluoromethylbenzonitrile

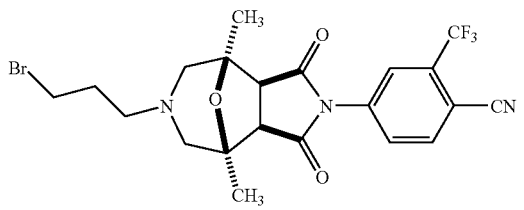

To a dry nitrogen purged 15 mL round bottomed flask equipped with a magnetic stirring bar was added carbon tetrabromide (43.0 mg, 0.129 mmol), triphenylphosphine (34.0 mg, 0.129 mmol) and CH$_2$Cl$_2$ (5 mL). The solution stirred at rt for 10 min and a solution of Example 155 (47.0 mg, 0.107 mmol) in CH$_2$Cl$_2$ (3 mL) was added dropwise. Once this addition was complete, the reaction was stirred for 3 h at rt then additional carbon tetrabromide (43.0 mg, 0.129 mmol) and triphenylphosphine (34.0 mg, 0.129 mmol) were added. The reaction was then stirred another 2 h at rt. The reaction solution was then concentrated and the residue chromatographed on silica gel eluting with 1:1 EtOAc in hexanes to afford 45.7 mg (85%) of Example 156 as a pale yellow solid. R$_f$=0.71 (SiO$_2$, 50% EtOAc in hexanes). HPLC (Method C): R$_t$=13.4 min. $^1$H NMR (500 MHz, CDCl$_3$): δ=7.94 (d, J=8.4 Hz, 1H), 7.87 (d, J=1.7 Hz, 1H), 7.76 (dd, J=8.3 Hz and 1.9 Hz, 1H) 3.46 (t, J=6.5 Hz, 2H), 3.39 (s, 1H), 2.75 (d, J=11.5 Hz, 2H), 2.56 (t, J=6.6 Hz, 2H), 2.14 (d, J=11.4 Hz, 2H), 2.03 (m, 2H) and 1.45 (s, 6H). m/z 501 [M+H]$^+$.

Example 157

4-{1,7-Dimethyl-3,5-dioxo-9-[3-(4,4,5,5,5-pentafluoropentylsulfanyl)propyl]-11-oxa-4,9-diazatricyclo[5.3.1.0$^{2,6}$]undec4-yl}-2-trifluoromethylbenzonitrile

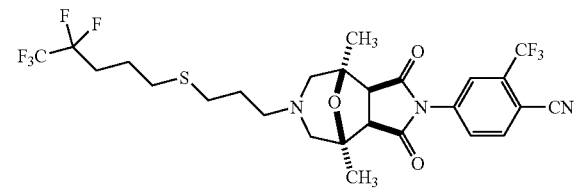

To a dry, nitrogen purged 10 mL round bottomed flask with a magnetic stir bar was added S-(4,4,5,5,5-pentafluoropentyl) thioester (22.0 mg, 0.090 mmol), dry THF (2 mL) and methanol (2 mL). The solution was stirred at rt and 5.5M NaOCH$_3$ solution in methanol (16 μL, 0.090 mmol) was added dropwise. This solution stirred 20 min and a solution of Preparation 10 (45.0 mg, 0.090 mmol) in THF (2 mL) was added dropwise. The resulting solution stirred at rt for 9 h and the solvent removed under reduced pressure. The resulting residue was dissolved in CH$_2$Cl$_2$ (2 mL) and the solution applied to a silica gel column. Elution with 50% EtOAc in hexanes and concentration of the product containing fractions afforded 25 mg (45%) of Example 157 as a clear, colorless oil. HPLC (Method C): R$_t$=16.0 min. $^1$H NMR (500 MHz, CDCl$_3$): δ=7.94 (d, J=8.4 Hz, 1H), 7.87 (d, J=1.7 Hz, 1H), 7.76 (dd, J=8.3 Hz and 1.9 Hz, 1H), 3.38 (s, 2H), 2.74 (d, J=11.3 Hz, 2H), 2.59 (m, 4H), 2.49 (t, J=6.9 Hz, 2H), 2.18 (m, 2H), 2.11 (d, J=11.4 Hz, 2H), 1.90 (m, 2H), 1.76 (m, 2H) and 1.44 (s, 6H). m/z 614 [M+H]$^+$.

Example 158

4{1,7-Dimethyl-3,5-dioxo-9-[3-(4,4,5,5,5-pentafluoropentane-1-sulfinyl)propyl]-11-oxa4,9-diazatricyclo[5.3.1.0$^{2,6}$]undec4-yl}-2-trifluoromethylbenzonitrile

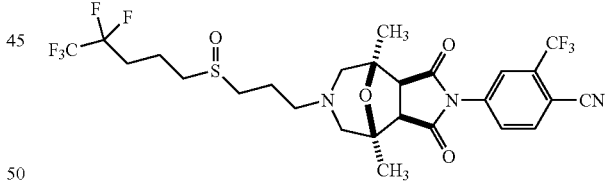

To a 25 mL round bottomed flask equipped with a magnetic stirring bar was added Example 157 (25.0 mg, 0.041 mmol) and dry THF (2 mL). The solution was stirred and cooled to 0° C. A solution of Oxone™ (12.0 mg, 0.020 mmol) in water (2 mL) was added and the reaction stirred vigorously for 1 h. The cold bath was removed and saturated aq. NaHCO$_3$ solution (10 mL) added. The resulting material was extracted with EtOAc (3×40 mL) and the combined organics were washed with saturated aq. NaCl solution (50 mL). After drying over Na$_2$SO$_4$, the solution was concentrated under reduced pressure. Purification of the residue by silica gel chromatography, eluting with 5% MeOH in CH$_2$Cl$_2$, followed by further purification by preparatory HPLC afforded 17.0 mg (66%) of Example 158 as a white solid. R$_f$=0.67 (SiO$_2$, 5% MeOH in CH$_2$Cl$_2$). HPLC (Method C): R$_t$=13.8 min. $^1$H NMR (500 MHz, CDCl$_3$): δ=7.94 (d, J=8.4 Hz, 1H), 7.87 (d, J=1.7 Hz, 1H), 7.76 (dd, J=8.3 Hz and 1.9 Hz, 1H), 3.46 (d, J=7.7 Hz, 1H), 3.39 (d, J=7.7 Hz, 1H), 2.77 (m, 4H), 2.67 (m, 1H), 2.55 (t, J=6.7 Hz, 2H), 2.26 (m, 2H), 2.16 (m, 4H), 2.00 (m, 2H) 1.65 (br s, 1H) and 1.44 (d, J=1.4 Hz, 6H). m/z 630 [M+H]+.

Example 159

4-[9-(6-Hydroxyhexyl)-1,7-dimethyl-3,5-dioxo-11-oxa-4,9-diazatricyclo[5.3.1.0$^{2,6}$]undec-4-yl]-2-trifluoromethylbenzonitrile

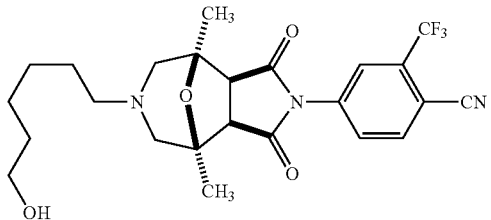

To a dry, nitrogen purged 50 mL round bottomed flask equipped with a magnetic stir bar was added Example 3 (126 mg, 0.333 mmol) and ethanol (6 mL). Triethylamine (37.7 mg, 0.373 mmol), potassium iodide (56.0 mg, 0.337 mmol) and (6-bromohexyloxy)-tert-butyldimethylsilane (118 mg, 0.399 mmol) were added and the resulting mixture was stirred at reflux for 7 days. After this time the reaction mixture was cooled to rt. After concentration the residue was purified by silica gel chromatography, eluting with 50-60% EtOAc in hexanes, to afford 87.6 mg (55%) of Example 159 as a viscous oil. $R_f$=0.34 (SiO$_2$, 50% EtOAc in hexanes). HPLC (Method C): $R_t$=11.5 min. $^1$H NMR (500 MHz, CDCl$_3$): δ=7.93 (d, J=8.3 Hz, 1H), 7.87 (d, J=1.8 Hz, 1H), 7.75 (dd, J=8.3 and 18 Hz, 1H), 3.65 (m, 2H), 3.38 (s, 2H), 2.73 (d, J=11.5 Hz, 2H), 2.37 (t, J=7.0 Hz, 2H), 2.06 (m, 2H), 1.57 (m, 2H), 1.47 (t, J=7.0 Hz, 2H), 1.44 (s, 6H) and 1.37 (m, 5H). m/z=480 [M+H]+.

Example 160

4-[9-(6-Bromohexyl)-1,7-dimethyl-3,5-dioxo-11-oxa4,9-diazatricyclo[5.3.1.0$^{2,6}$]undec4-yl]-2-trifluoromethylbenzonitrile

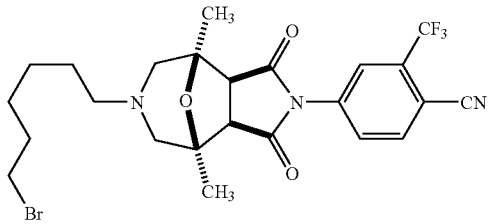

To a dry, nitrogen purged 50 mL round bottomed flask equipped with a magnetic stir bar was added carbon tetrabromide (212 mg, 0.639 mmol), triphenylphosphine (168 mg, 0.640 mmol) and CH$_2$Cl$_2$ (5 mL). The solution was stirred at rt and a solution of Example 159 (84.5 mg, 0.176 mmol) in CH$_2$Cl$_2$ (3 mL) added. The reaction was stirred at rt for 24 h then concentrated. The resulting residue was purified by preparative HPLC, which afforded 82.1 mg (86%) of Example 160 as a viscous oil. $R_f$=0.56 (SiO$_2$, 30% EtOAc in hexanes). HPLC (Method C): $R_t$=14.0 min. $^1$H NMR (500 MHz, CDCl$_3$): δ=7.94 (d, J=8.3 Hz, 1H), 7.87 (d, J=1.8 Hz, 1H), 7.75 (dd, J=8.3 and 1.8 Hz, 1H), 3.41 (m, 4H), 2.72 (d, J=11.5 Hz, 2H), 2.37 (t, J=6.9 Hz, 2H), 2.06 (m, 2H), 1.87 (m, 2H), 1.47 (m, 4H), 1.44 (s, 6H) and 1.36 (m, 2H). m/z=542 [M+H]+.

Example 161

4-{1,7-Dimethyl-3,5-dioxo-9-[6-(4,4,5,5,5-pentafluoropentylsulfanyl)hexyl]-11-oxa-4,9-diazatricyclo[5.3.1.0$^{2,6}$]undec4-yl}-2-trifluoromethylbenzonitrile

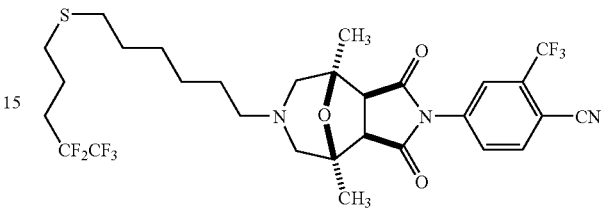

To a dry, nitrogen purged 25 mL round bottomed flask equipped with a magnetic stir bar was added thioacetic acid S-(4,4,5,5,5-pentafluoropentyl) ester (34.0 mg, 0.144 mmol) followed by anhydrous THF (3 mL) and MeOH (3 mL). The resulting solution was stirred at rt and a 30% solution of NaOCH$_3$ in MeOH (27 μL, 0.144 mmol) added via syringe. The reaction was stirred at rt for 20 min then a solution of Example 160 (78.0 mg, 0.144 mmol) in THF (3 mL) added. The reaction mixture was stirred at rt for an additional 5.5 h. After this time the reaction was concentrated and the crude product purified by silica gel chromatography, eluting with 30% EtOAc in hexanes, to afford 29.6 mg (31%) of Example 161 as a light yellow oil. $R_f$=0.29 (SiO$_2$, 30% EtOAc in hexanes). HPLC (Method C): $R_t$=16.5 min. $^1$H NMR (500 MHz, CDCl$_3$): δ=7.93 (d, J=8.3 Hz, 1H), 7.87 (d, J=1.8 Hz, 1H), 7.75 (dd, J=8.3 and 1.8 Hz, 1H), 3.38 (s, 2H), 2.73 (d, J=11.5 Hz, 2H), 2.59 (t, J=7.1 Hz, 2H), 2.52 (t, J=7.1 Hz, 2H), 2.36 (t, J=7.1 Hz, 2H), 2.17 (m, 2H), 2.06 (m, 2H), 1.88 (m, 2H), 1.58 (m, 2H), 1.44 (s, 6H), 1.43 (m, 4H) and 1.32 (m, 2H). m/z=656 [M+H]+.

Example 162

4-{1,7-Dimethyl-3,5-dioxo-9-[6-(4,4,5,5,5-pentafluoropentane-1-sulfinyl)hexyl]-11-oxa-4,9-diazatricyclo[5.3.1.0$^{2,6}$]undec-4-yl}-2-trifluoromethylbenzonitrile

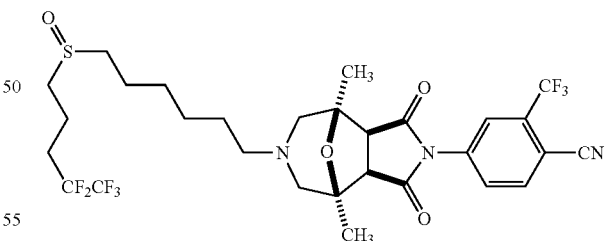

To a dry, nitrogen purged 25 mL round bottomed flask equipped with a magnetic stir bar was added Example 161 (29.6 mg, 45.1 mmol) and THF (2 mL). The stirred solution was cooled to 0° C. and a solution of Oxone™ (14.0 mg, 22.8 mmol) in water (2 mL) added. The reaction mixture was stirred vigorously for 50 min then the reaction was quenched with saturated aq. NaHCO$_3$ (10 mL). EtOAc (40 mL) was added and the aqueous layer was separated, then extracted with EtOAc (2×20 mL). The combined EtOAc extracts were washed with brine (50 mL), dried over Na$_2$SO$_4$, filtered and concentrated. The resulting crude material was purified by preparative HPLC to afford 23.6 mg (78%) of Example 162 as a viscous oil. $R_f$=0.52 (SiO$_2$, 5% MeOH in CH$_2$Cl$_2$). HPLC (Method C): $R_t$=13.7 min. $^1$H NMR (500 MHz, CDCl$_3$): δ=7.93 (d, J=8.3 Hz, 1H), 7.87 (d, J=1.9 Hz, 1H), 7.75 (dd, J=8.3 and 1.9 Hz, 1H), 3.37 (s, 2H), 2.74 (m, 5H), 2.64 (m, 1H), 2.37 (t, J=7.0 Hz, 2H), 2.24 (m, 2H), 2.16 (m, 2H), 2.08 (m, 2H), 1.80 (m, 2H), 1.54 (m, 2H), 1.48 (m, 2H), 1.44 (s, 6H) and 1.38 (m, 2H). m/z=672 [M+H]$^+$.

Example 163

4-[9-(3-Methoxybenzyl)-1,7-dimethyl-3,5-dioxo-11-oxa4,9-diazatricyclo[5.3.1.0$^{2,6}$]undec4-yl]-2-trifluoromethylbenzonitrile

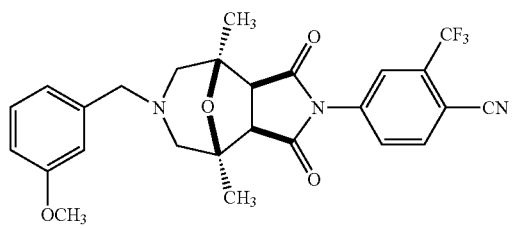

A 25 mL round bottomed flask equipped with a magnetic stir bar was charged with Example 3 (50.0 mg, 0.13 mmol), potassium iodide (42.0 mg, 0.25 mmol), triethylamine (26 μL, 0.19 mmol) and ethanol (3.0 mL). 3-Methoxybenzylbromide (28 μL, 0.20 mmol) was then added and the solution heated to reflux. After heating at reflux for 1.5 h the reaction solution was cooled and concentrated. The residue was diluted with 50% CH$_3$CN in H$_2$O (5 mL). Purification via preparative HPLC and subsequent concentration produced a residue that was dissolved in CH$_2$Cl$_2$ (5 mL) and was concentrated to afford 56.4 mg (87%) of Example 163 as a white solid. $R_f$=0.45 (SiO$_2$, 30% EtOAc in hexanes). HPLC (Method C): $R_t$=14.8 min. $^1$H NMR (500 MHz, CDCl$_3$): δ=7.93 (d, J=8.3 Hz, 1H), 7.86 (d, J=1.8 Hz, 1H), 7.75 (dd, J=8.3 and 2.0 Hz, 1H), 7.25 (m, 1H), 6.84 (m, 3H), 3.81 (s, 3H), 3.51 (m, 2H), 3.44 (s, 2H), 2.73 (d, J=11.5 Hz, 2H), 2.15 (d, J=11.5 Hz, 2H) and 1.42 (s, 6H). m/z=500 [M+H]$^+$.

Preparation 12

Benzyl 5-Bromopentanoate

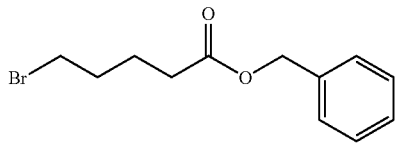

To a dry, nitrogen purged 100 mL round bottomed flask was added benzyl alcohol (2.98 g, 0.027 mol), triethylamine (2.79 g, 0.027 mol) and CH$_2$Cl$_2$ (50 mL). The solution was stirred and cooled to 0° C. and 5-bromovaleryl chloride (5.00 g, 0.025 mol) added dropwise. A white suspension formed and this mixture was stirred at 0° C. for 0.5 h then warmed to rt over 1 h. After stirring at rt for 15 h, the suspension was poured into water (100 mL) and the phases separated. The aqueous layer was extracted with CH$_2$Cl$_2$ (1×100 mL) and the combined CH$_2$Cl$_2$ layers were dried over Na$_2$SO$_4$. Filtration and concentration produced a light brown suspension, which was diluted with EtOAc (50 mL) and then re-filtered. After concentration, the resulting amber oil was chromatographed on silica gel using 10% EtOAc in hexanes to give 6.79 g (100%) of Preparation 12 as a clear, colorless oil. $R_f$=0.80 (SiO$_2$, 50% EtOAc in hexanes). $^1$H NMR (500 MHz, CDCl$_3$): δ=7.33 (m, 5H), 5.11 (s, 2H), 3.38 (t, J=6.5 Hz, 2H), 2.38 (t, J=7.0 Hz, 2H), 1.88 (m, 2H) and 1.79 (m, 2H).

Preparation 13

Benzyl 6-Bromohexanoate

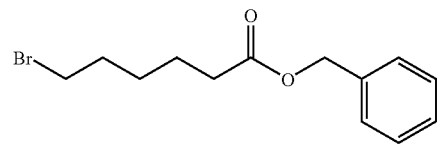

Preparation 13 was prepared in identical fashion to Preparation 12 in 96% yield. $R_f$=0.82 (SiO$_2$, 50% EtOAc in hexanes). $^1$H NMR (500 MHz, CDCl$_3$): δ=7.33 (m, 5H), 5.11 (s, 2H), 3.38 (t, J=6.7 Hz, 2H), 2.37 (t, J=7.4 Hz, 2H), 1.85 (m, 2H), 1.67 (m, 2H) and 1.46 (m, 2H).

Example 164

Benzyl 6-[4-(4-Cyano-3-trifluoromethylphenyl)-1,7-dimethyl-3,5-dioxo-11-oxa-4,9-diazatricyclo[5.3.1.0$^{2,6}$]undec-9-yl]pentanoate

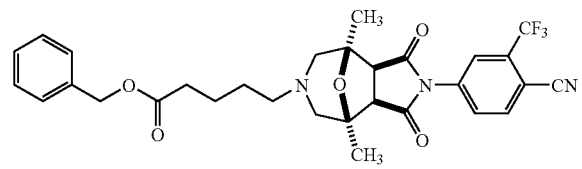

To a nitrogen purged 25 mL round bottomed flask was added Example 3 (100 mg, 0.26 mmol) and ethanol (10 mL). The mixture was stirred and potassium iodide (44.0 mg, 0.26 mmol), triethylamine (44.0 mg, 0.43 mmol) and Preparation 12 (148 mg, 0.54 mmol) were added. The suspension was stirred at reflux for 65 h and then cooled to rt. After concentrating under reduced pressure, the residue was chromatographed on silica gel using 30% EtOAc in hexanes. The product containing fractions were concentrated to give 133 mg (89%) of Example 164 as a viscous, colorless oil. $R_f$=0.39 (SiO$_2$, 30% EtOAc in hexanes). $^1$H NMR (500 MHz, CDCl$_3$): δ=7.94 (d, J=8.3 Hz, 1H), 7.87 (d, J=1.8 Hz, 1H), 7.74 (dd, J=8.0 and 2.0 Hz, 1H), 5.13 (s, 2H), 3.37 (s, 2H), 2.70 (d, J=1.5 Hz, 2H), 2.37 (m, 4H), 2.05 (d, J=11.5 Hz, 2H), 1.68 (m, 2H), 1.48 (m, 2H) and 1.43 (s, 6H). m/z 570 [M+H]$^+$.

Example 165

Benzyl 6-[4-(4-Cyano-3-trifluoromethylphenyl)-1,7-dimethyl-3,5-dioxo-11-oxa-4,9-diazatricyclo[5.3.1.0$^{2,6}$]undec-9-yl]hexanoate

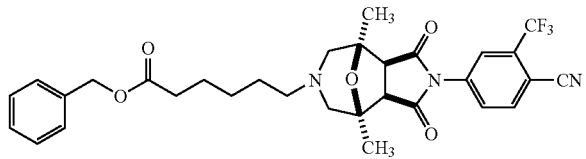

To a nitrogen purged 50 mL round bottomed flask was added Example 3 (300 mg, 0.79 mmol) and absolute ethanol (30 mL). The mixture was stirred and potassium iodide (131 mg, 0.79 mmol), triethylamine (88.0 mg, 0.87 mmol) and Preparation 13 (293 mg, 1.03 mmol) were added. The suspension was stirred at reflux for 110 h and then cooled to rt. After concentrating under reduced pressure, the residue was diluted with CH$_2$Cl$_2$ (10 mL) and chromatographed on silica gel using 30% EtOAc in hexanes. The product containing fractions were concentrated to give 382 mg (83%) of Example 165 as a viscous, colorless oil. $R_f$=0.43 (SiO$_2$, 30% EtOAc in hexanes). $^1$H NMR (500 MHz, CDCl$_3$): δ=7.93 (d, J=8.3 Hz, 1H), 7.87 (d, J=1.6 Hz, 1H), 7.75 (dd, J=8.0 and 2.0 Hz, 1H), 5.12 (s, 2H), 3.37 (s, 2H), 2.71 (d, J=11.5 Hz, 2H), 2.37 (m, 4H), 2.06 (d, J=11.5 Hz, 2H), 1.66 (m, 2H), 1.46 (m, 8H) and 1.35 (m, 2H).

Example 166

5-[4-(4-Cyano-3-trifluoromethylphenyl)-1,7-dimethyl-3,5-dioxo-11-oxa4,9-diazatricyclo[5.3.1.0$^{2,6}$]undec-9-yl]pentanoic acid

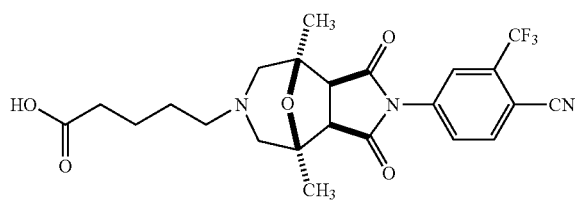

To a nitrogen purged 50 mL round bottomed flask was added Example 164 (200 mg, 0.35 mmol), ethanol (20 mL) and ethyl acetate (5 mL). 5% Palladium on carbon (40.0 mg, 51.4% wet) was then added and the suspension stirred under a balloon maintained hydrogen atmosphere for 1 h. The hydrogen was then evacuated and the suspension filtered through a Celite pad. The filtrate was concentrated to give 157 mg (93%) of Example 166 as a white solid. $R_f$=0.33 (SiO$_2$, 5% MeOH in CH$_2$Cl$_2$). $^1$H NMR (500 MHz, CDCl$_3$): δ=7.94 (d, J=8.3 Hz, 1H), 7.87 (d, J=1.8 Hz, 1H), 7.75 (dd, J=8.0 and 2.0 Hz, 1H), 3.40 (s, 2H), 2.75 (d, J=11.5 Hz, 2H), 2.39 (m, 4H), 2.09 (d, J=11.5 Hz, 2H), 1.68 (m, 2H), 1.52 (m, 2H) and 1.44 (s, 6H). m/z 480 [M+H]$^+$.

Example 167

5-[4-(4-Cyano-3-trifluoromethyl-phenyl)-1,7-dimethyl-3,5-dioxo-11-oxa-4,9-diazatricyclo[5.3.1.0$^{2,6}$]undec-9-yl]hexanoic acid

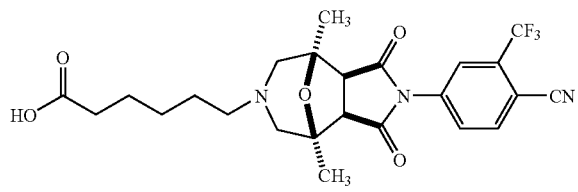

To a nitrogen purged 50 mL round bottomed flask was added Example 165 (327 mg, 0.56 mmol), methanol (15 mL) and ethyl acetate (15 mL). 5% Palladium on carbon (65.0 mg, 51.4% wet) was added and the suspension stirred under a balloon maintained hydrogen atmosphere for 1 h. The hydrogen was then evacuated and the suspension filtered through a Celite pad. The filtrate was concentrated to give 232 mg (84%) of Example 167 as a white solid. $R_f$=0.37 (SiO$_2$, 5% MeOH in CH$_2$Cl$_2$). $^1$H NMR (500 MHz, CDCl$_3$): δ=7.94 (d, J=8.3 Hz, 1H), 7.88 (d, J=1.6 Hz, 1H), 7.76 (dd, J=8.0 and 2.0 Hz, 1H), 3.39 (s, 2H), 2.73 (d, J=11.5 Hz, 2H), 2.37 (m, 2H), 2.33 (m, 2H), 2.07 (d, J=11.5 Hz, 2H), 1.62 (m, 2H), 1.44 (m, 8H) and 1.36 (m, 2H). m/z 494 [M+H]$^+$.

Example 168

6-[4-(4-Cyano-3-trifluoromethylphenyl)-1,7-dimethyl-3,5-dioxo-11-oxa4,9-diazatricyclo[5.3.1.0$^{2,6}$]undec-9-yl]hexanoic acid dimethylamide

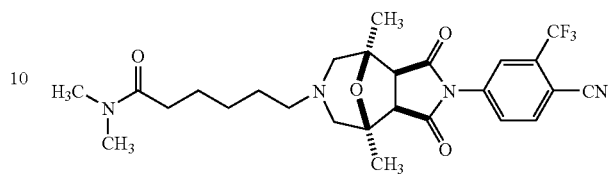

To a nitrogen purged two dram vial equipped with a magnetic stirring bar was added Example 167 (40.0 mg, 0.081 mmol), N,N-diisopropylethylamine (31.0 mg, 0.243 mmol) and dry THF (2 mL). 1-(3-Dimethylaminopropyl)-3-ethyl carbodiimide hydrochloride (EDCI, 31.0 mg, 0.162 mmol) and 1-hydroxybenzotriazole (22.0 mg, 0.162 mmol) were then added and the reaction stirred for 10 min. A solution of N,N-dimethylamine (2.0M in THF, 162 μL, 0.162 mmol) was added and the suspension stirred for 15 h at rt. The resulting mixture was concentrated to dryness under reduced pressure and CH$_2$Cl$_2$ (20 mL) added to the residue. The resulting solution was washed with 10% aq. citric acid solution (50 mL) and the CH$_2$Cl$_2$ layer was dried over Na$_2$SO$_4$, filtered and concentrated to a yellow solid (51 mg). The material was purified by preparatory HPLC, affording 42.0 mg (99%) of Example 168 as a yellow solid. $R_f$=0.45 (SiO$_2$, 5% MeOH in CH$_2$Cl$_2$). HPLC (Method C): $R_t$=11.8 min. $^1$H NMR (500 MHz, CDCl$_3$): δ=7.94 (d, J=8.3 Hz, 1H), 7.87 (d, J=1.7 Hz, 1H), 7.75 (dd, J=8.3 Hz and 1.8 Hz, 1H), 3.40 (br s, 2H), 3.00 (s, 3H), 2.94 (s, 3H), 2.73 (m, 2H), 2.38 (m, 2H), 2.32 (t, J=7.3 Hz, 2H), 2.08 (m, 2H), 1.65 (m, 2H), 1.52 (m, 2H), 1.44 (s, 6H) and 1.37 (m, 2H). m/z 521 [M+H]$^+$.

Examples 169 to 174

Examples 169 to 174 were prepared according to the general procedure indicated in Table 4 and had the general formula represented by

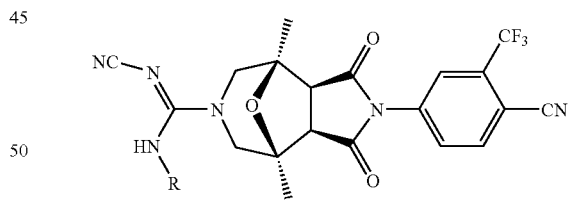

wherein R is defined in Table 4.

TABLE 4

| Ex. No. | R | Retention Time Min. | HPLC Method | Procedure of Example |
|---|---|---|---|---|
| 169 | Cl-phenyl- | 3.498 LC 555.0 [M + H]$^+$ | A | 145 |

TABLE 4-continued

| Ex. No. | R | Retention Time Min. | HPLC Method | Procedure of Example |
|---|---|---|---|---|
| 170 | 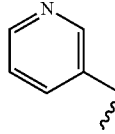 | 3.498 LC 524.1 [M + H]⁺ | A | 145 |
| 171 | 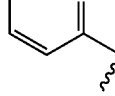 | 2.660 LC 524.1 [M + H]⁺ | A | 145 |
| 172 | 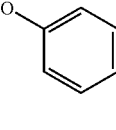 MeO | 3.338 LC 553.4 [M + H]⁺ | A | 145 |
| 173 | 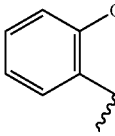 OMe | 3.307 LC 553.4 [M + H]⁺ | A | 145 |
| 174 | 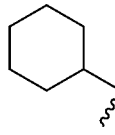 | 3.505 LC 529.1 [M + H]⁺ | A | 145 |

Examples 175 to 177

Examples 175 to 177 were prepared according to the general procedure indicated in Table 5 and had the general formula represented by

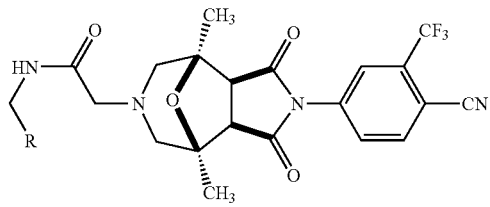

wherein R is defined in Table 5.

TABLE 5

| Ex. No. | R | Retention Time Min. | HPLC Method | Procedure of Example |
|---|---|---|---|---|
| 175 | Cl-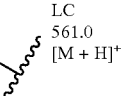 | 15.011 LC 561.0 [M + H]⁺ | C | 146 |
| 176 | F-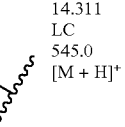 | 14.311 LC 545.0 [M + H]⁺ | C | 146 |
| 177 | MeO-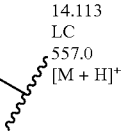 | 14.113 LC 557.0 [M + H]⁺ | C | 146 |

Examples 178 to 188

Examples 178 to 188 were prepared according to the general procedure indicated in Table 6 and had the general formula represented by

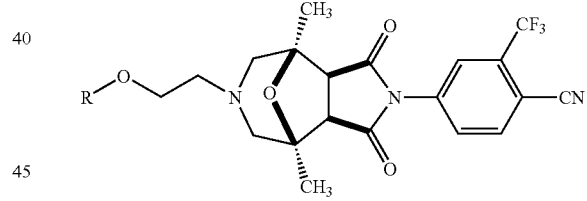

wherein R is defined in Table 8.

TABLE 6

| Ex. No. | R | Retention Time Min. | HPLC Method | Procedure of Example |
|---|---|---|---|---|
| 178 | F-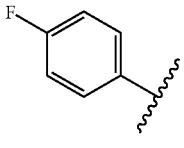 | 15.03 LC 518.2 [M + H]⁺ | C | 148 |

TABLE 6-continued

| Ex. No. | R | Retention Time Min. | HPLC Method | Procedure of Example |
|---|---|---|---|---|
| 179 | 4-Cl-C6H4-CH2- | 15.818 LC 534.8 [M + H]+ | C | 148 |
| 180 | CH3CH2-C(O)-NH-C6H4- | 12.981 LC 571.2 [M + H]+ | C | 150 |
| 181 | 4-MeO-C6H4-CH2-C(O)-NH-C6H4- | 14.336 LC 663.3 [M + H]+ | C | 150 |
| 182 | CF3-CF2-CF2-C(O)-NH-C6H4- | 16.221 LC 711.0 [M + H]+ | C | 150 |
| 183 | C6H5-NH-C(O)-NH-C6H4- | 14.445 LC 664.2 [M + H]+ | C | 153 |
| 184 | C6H5-O-C(O)-NH-C6H4- | 15.095 LC 635.1 [M + H]+ | C | 152 |
| 185 | (CH3)2CH-O-C(O)-NH-C6H4- | 14.682 LC 601.1 [M + H]+ | C | 152 |
| 186 | 3-F-C6H4-S(O)2-NH-C6H4- | 14.865 LC 673.2 [M + H]+ | C | 151 |

TABLE 6-continued

| Ex. No. | R | Retention Time Min. | HPLC Method | Procedure of Example |
|---|---|---|---|---|
| 187 | F₃C-CH₂-SO₂-NH-C₆H₄-⁓ | 14.318 LC 661.1 [M + H]⁺ | C | 151 |
| 188 | C₆H₅-C(O)-NH-C₆H₄-⁓ | 14.421 LC 619.2 [M + H]⁺ | C | 150 |

Examples 189 to 192

Examples 189 to 192 were prepared according to the general procedure indicated in Table 7 and had the general formula represented by

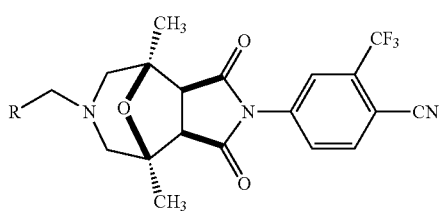

wherein R is defined in Table 7.

TABLE 7

| Ex. No. | R | Retention Time Min. | HPLC Method | Procedure of Example |
|---|---|---|---|---|
| 189 | 4-F-C₆H₄- | 15.047 LC 488.2 [M + H]⁺ | C | 163 |
| 190 | 4-Cl-C₆H₄- | 16.347 LC 504.32 [M + H]⁺ | C | 163 |
| 191 | 4-F₃C-C₆H₄- | 17.558 LC 538.1 [M + H]⁺ | C | 163 |
| 192 | 3-F₃C-C₆H₄- | 17.501 LC 538.2 [M + H]⁺ | C | 163 |

Examples 193 to 199

Examples 193 to 199 were prepared according to the general procedure indicated in Table 8 and had the general formula represented by

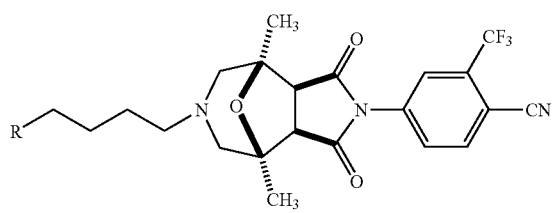

wherein R is defined in Table 8.

TABLE 8

| Ex. No. | R | Retention Time Min. | HPLC Method | Procedure of Example |
|---|---|---|---|---|
| 193 | n-Bu-N(CH₃)-C(O)-⁓ | 13.558 LC 549.2 [M + H]⁺ | C | 168 |

TABLE 8-continued

| Ex. No. | R | Retention Time Min. | HPLC Method | Procedure of Example |
|---|---|---|---|---|
| 194 | piperidine-C(O)-CH2- | 13.051 LC 547.2 [M + H]⁺ | C | 168 |
| 195 | pyrrolidine-C(O)-CH2- | 12.465 LC 533.2 [M + H]⁺ | C | 168 |
| 196 | (CH3)2N-C(O)-CH2- | 11.898 LC 507.2 [M + H]⁺ | C | 168 |
| 197 | n-Bu-N(CH3)-C(O)-CH2-CH2- | 13.411 LC 563.2 [M + H]⁺ | C | 168 |
| 198 | pyrrolidine-C(O)-CH2-CH2- | 12.236 LC 547.2 [M + H]⁺ | C | 168 |
| 199 | piperidine-C(O)-CH2-CH2- | 12.883 LC 561.2 [M + H]⁺ | C | 168 |

Examples 200 to 203

Examples 200 to 203 were prepared according to the general procedure indicated in Table 9 and had the general formula represented by

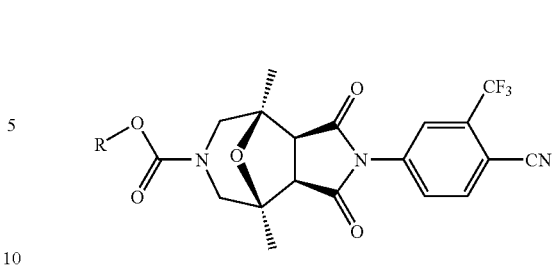

wherein R is defined in Table 9.

TABLE 9

| Ex. No. | R | Retention Time Min. | HPLC Method | Procedure of Example |
|---|---|---|---|---|
| 200 | MeO-C6H4-CH2-CH2- | 16.170 LC 558.42 [M + H]⁺ | C | 11 |
| 201 | F-C6H4-CH2-CH2- | 16.298 LC 546.7 [M + H]⁺ | C | 11 |
| 202 | Cl-C6H4-CH2-CH2- | 17.061 LC 562.5 [M + H]⁺ | C | 11 |
| 203 | F3C-CF2-CH2- | 16.277 LC 556.6 [M + H]⁺ | C | 11 |

TABLE 10

¹H NMR DATA

| Compound # | ¹H NMR Data |
|---|---|
| 36 | ¹H NMR(400MHz, CDCl₃) δ 7.88(d, J=8.3Hz, 1H), 7.78(d, J=1.7Hz, 1H), 7.68(dd, J=1.7Hz, 8.3Hz, 1H), 3.62(d, J=12.4Hz, 2H), 3.46(s, 2H), 2.93(q, d=7.5Hz, 2H), 2.83(d, J=12.4, 2H), 1.41(s, 6H), 1.29(t, J=7.5Hz, 3H); |
| 37 | ¹H NMR(400MHz, CDCl₃) δ 7.87(d, J=8.4Hz, 1H), 7.78(d, J=1.5Hz, 1H), 7.75-7.65(m, 3H), 7.60(t, J=7.6Hz, 1H), 7.52(t, J=7.6Hz, 2H), 3.57(d, J=11.7Hz, 2H), 3.47(s, 2H), 2.26(d, J=11.7, 2H), 1.39(s, 6H); |
| 38 | ¹H NMR(400MHz, CDCl₃) δ 7.88(d, J=8.4Hz, 1H), 7.79(d, J=1.7Hz, 1H), 7.68(dd, J=1.9, 8.4Hz, 1H), 4.14(d, J=8Hz, 1H), 3.82-3.97(m, 1H), 3.67(d, J=12.8Hz, 2H), 3.25(s, 2H), 2.80(d, J=12.7Hz, 2H), 1.43(s, 6H), 1.11(d, J=6.5Hz, 6H); |
| 40 | ¹H NMR(400MHz, CDCl₃) δ 7.87(d, J=8.4Hz, 1H), 7.80(d, J=1.7Hz, 1H), 7.68(dd, J=1.7Hz, 8.4Hz, 1H), 3.33(s, 2H), 2.67(d, J=11.5Hz, 2H), 2.27(t, J=7.3Hz, 2H), 2.01(d, J=11.5, 2H), 1.35-1.45(m, 8H), 0.84(t, J=7.3Hz, 3H); |

TABLE 10-continued

¹H NMR DATA

| Compound # | ¹H NMR Data |
|---|---|
| 43 | ¹H NMR(500MHz, CD$_3$OD) δ 8.12(d, J=10Hz, 1H), 7.94(s, 1H), 7.84(dd, J=10Hz, 1H), 3.49(s, 2H), 2.95(d, J=10Hz, 2H), 2.48(d, J=10, 2H), 1.39(s, 6H), 1.36(s, 6H); |
| 46 | ¹H NMR(300MHz, CDCl$_3$): δ=7.95(d, J=8.4Hz, 1H), 7.85(d, J=1.8Hz, 1H), 7.75(dd, J=8.0 and 2.0Hz, 1H), 4.35(m, 1H), 3.75(d, J=12.9Hz, 2H), 3.33(s, 2H), 3.30(m, 2H), 2.89(d, J=12.7Hz, 2H), 1.50(s, 3H) and 1.17(t, J=7.2Hz, 3H). |
| 47 | ¹H NMR(500MHz, CDCl$_3$): δ=8.73(m, 1H), 7.96(m, 3H), 7.86(d, J=1.7Hz, 1H), 7.75(m, 1H), 7.55(m, 1H), 3.76(d, J=12.4Hz, 2H), 3.55(s, 2H), 2.91(d, J=12.3Hz, 2H) and 1.48(s, 6H). |
| 48 | ¹H NMR(300MHz, CDCl$_3$): δ=7.95(d, J=8.0Hz, 1H), 7.85(d, J=1.8Hz, 1H), 7.74(dd, J=8.0 and 1.8Hz, 1H), 4.96(sept, J=6.3Hz, 1H), 3.95(m, 2H), 3.27(m, 2H), 2.89(m, 2H), 1.49(s, 6H) and 1.27(d, J=6.3Hz, 6H). |
| 49 | ¹H NMR(300MHz, CDCl$_3$): δ=7.95(d, J=8.0Hz, 1H), 7.85(d, J=1.8Hz, 1H), 7.74(dd, J=8.0 and 1.8Hz, 1H), 3.99(m, 4H), 3.27(m, 2H), 2.91(m, 2H), 1.66(m, 2H), 1.49(s, 6H) and 0.96(t, J=7.4Hz, 3H). |
| 50 | ¹H NMR(300MHz, CDCl$_3$): δ=7.95(d, J=8.4Hz, 1H), 7.86(d, J=1.8Hz, 1H), 7.75(dd, J=8.0 and 2.0Hz, 1H), 7.33(m, 4H), 7.10(m, 1H), 6.31(br s, 1H), 3.91(d, J=12.9Hz, 2H), 3.38(s, 2H), 3.01(d, J=12.7Hz, 2H) and 1.53(s, 6H). |
| 51 | ¹H NMR(500MHz, CDCl$_3$): δ=7.95(d, J=8.4Hz, 1H), 7.86(d, J=1.8Hz, 1H), 7.75(dd, J=8.0 and 2.0Hz, 1H), 7.30(m, 2H), 7.01(m, 2H), 6.29(br s, 1H), 3.89(d, J=12.9Hz, 2H), 3.38(s, 2H), 3.01(d, J=12.7Hz, 2H) and 1.53(s, 6H). |
| 52 | ¹H NMR(500MHz, CDCl$_3$): δ=7.94(d, J=8.0Hz, 1H), 7.84(d, J=1.8Hz, 1H), 7.73(dd, J=8.0 and 2.0Hz, 1H), 7.46(m, 4H), 7.41(d, J=1.7Hz, 1H), 4.72(br s, 1H), 3.63(br s, 1H), 3.50(br s, 1H), 3.32(br s, 1H), 3.09(br s, 1H), 2.94(br s, 1H), 1.53(br s, 3H) and 1.40(br s, 3H). |
| 53 | ¹H NMR(300MHz, CDCl$_3$): δ=7.95(d, J=8.0Hz, 1H), 7.85(d, J=1.8Hz, 1H), 7.74(dd, J=8.0 and 2.0Hz, 1H), 4.47(d, J=13.3Hz, 1H), 3.64(d, J=13.0Hz, 1H), 3.26(d, J=7.7Hz, 1H), 3.15(m, 2H), 2.68(d, J=13.5Hz, 1H), 2.36(m, 2H), 1.51(s, 3H), 1.50(s, 3H) and 1.18(t, J=7.4Hz, 3H). |
| 54 | ¹H NMR(300MHz, CDCl$_3$): δ=7.95(d, J=8.0Hz, 1H), 7.85(d, J=1.8Hz, 1H), 7.74(dd, J=8.0 and 2.0Hz, 1H), 4.50(d, J=13.5Hz, 1H), 4.00(d, J=12.7Hz, 1H), 3.28(m, 3H), 2.71(d, J=12.7Hz, 1H), 1.57(m, 1H), 1.54(s, 3H), 1.50(s, 3H), 1.11(m, 1H) and 0.90(m, 3H). |
| 55 | ¹H NMR(500MHz, CDCl$_3$): δ=8.55(d, J=4.6Hz, 1H), 7.94(d, J=8.4Hz, 1H), 7.84(d, J=1.5Hz, 1H), 7.75(d, J=1.8Hz, 1H), 7.69(m, 1H), 7.22(m, 2H), 3.64(d, J=12.5Hz, 2H), 3.53(m, 2H), 3.51(s, 2H), 3.27(m, 2H), 2.78(d, J=12.3Hz, 2H) and 1.46(s, 6H). |
| 56 | ¹H NMR(500MHz, CDCl$_3$): δ=7.95(d, J=8.4Hz, 1H), 7.85(d, J=1.7Hz, 1H), 7.75(dd, J=8.0 and 2.0Hz, 1H), 3.63(d, J=11.8Hz, 2H), 3.51(s, 2H), 2.66(s, 3H), 2.61(d, J=11.7Hz, 2H), 2.41(s, 3H) and 1.50(s, 3H). |
| 57 | ¹H NMR(300MHz, CDCl$_3$): δ=7.94(d, J=8.3Hz, 1H), 7.85(s, 1H), 7.75(dd, J=8.0 and 2.0Hz, 1H), 3.65(d, J=12.1Hz, 2H), 3.51(s, 2H), 2.84(s, 3H), 2.79(d, J=11.9Hz, 2H) and 1.51(s, 6H). |
| 58 | ¹H NMR(300MHz, CDCl$_3$): δ=7.95(d, J=8.3Hz, 1H), 7.85(d, J=1.7Hz, 1H), 7.77(m, 3H), 7.26(m, 2H), 3.63(d, J=11.8Hz, 2H), 3.53(s, 2H), 2.37(d, J=11.7Hz, 2H) and 1.46(s, 6H). |
| 59 | ¹H NMR(500MHz, CDCl$_3$): δ=7.95(d, J=8.3Hz, 1H), 7.85(d, J=1.8Hz, 1H), 7.75(dd, J=8.3 and 1.8Hz, 1H), 3.65(d, J=12.4Hz, 2H), 3.52(s, 2H), 3.09(t, J=7.1Hz, 2H), 2.91(m, 4H), 2.55(q, J=7.1Hz, 4H), 1.48(s, 6H) and 1.05(t, J=7.1Hz, 6H). |
| 62 | ¹H NMR(500MHz, CDCl$_3$): δ=7.94(d, J=8.3Hz, 1H), 7.87(s, 1H), 7.76(dd, J=8.3 and 1.9Hz, 1H), 3.37(m, 4H), 3.36(s, 2H), 3.18(sept, J=6.8Hz, 1H), 2.77(d, J=11.4Hz, 2H), 2.54(m, 8H), 2.15(d, J=11.4Hz, 2H), 1.44(s, 6H) and 1.34(d, J=6.8Hz, 6H). |
| 63 | ¹H NMR(500MHz, CDCl$_3$): δ=7.94(d, J=8.3Hz, 1H), 7.87(d, J=1.8Hz, 1H), 7.75(dd, J=8.3 and 1.8Hz, 1H), 3.36(s, 2H), 3.32(m, 4H), 2.95(q, J=7.4Hz, 2H), 2.77(d, J=11.4Hz, 2H), 2.54(br s, 8H), 2.15(d, J=11.4Hz, 2H), 1.44(s, 6H) and 1.37(t, J=7.4Hz, 3H). |
| 64 | ¹H NMR(500MHz, CDCl$_3$): δ=7.94(d, J=8.3Hz, 1H), 7.87(s, 1H), 7.75(dd, J=8.3 and 1.7Hz, 1H), 3.70(q, J$_{H-F}$=9.3Hz, 2H), 3.38(m, 4H), 3.35(s, 2H), 2.77(d, J=11.2Hz, 2H), 2.56(br s, 8H), 2.15(d, J=11.2Hz, 2H) and 1.44(s, 6H). |
| 66 | ¹H NMR(500MHz, CDCl$_3$): δ=7.94(d, J=8.3Hz, 1H), 7.87(d, J=1.6Hz, 1H), 7.75(dd, J=8.3 and 2.0Hz, 1H), 4.92(sept, J=6.2Hz, 1H), 3.47(m, 4H), 3.37(s, 2H), 2.78(d, J=11.2Hz, 2H), 2.55(m, 2H), 2.49(m, 2H), 2.42(m, 4H), 2.15(d, J=11.2Hz, 2H), 1.45(s, 3H), 1.44(s, 3H) and 1.24(d, J=6.2Hz, 3H). |

TABLE 10-continued

¹H NMR DATA

| Compound # | ¹H NMR Data |
|---|---|
| 67 | ¹H NMR(500MHz, CDCl₃): δ=7.94(d, J=8.3Hz, 1H), 7.87(d, J=1.6Hz, 1H), 7.75(dd, J=8.3 and 2.0Hz, 1H), 3.63(br s, 2H), 3.52(br s, 2H), 3.37(s, 2H), 2.78(m, 3H), 2.58-2.45(m, 8H), 2.16(d, J=11.2Hz, 2H), 1.44(s, 6H) and 1.13(d, J=6.7Hz, 6H). |
| 68 | ¹H NMR(500MHz, CDCl₃): δ=7.94(d, J=8.3Hz, 1H), 7.87(d, J=1.8Hz, 1H), 7.75(dd, J=8.3 and 1.8Hz, 1H), 7.72(d, J=8.3Hz, 2H), 7.50(d, J=8.3Hz, 2H), 3.79(m, 2H), 3.35(m, 4H), 2.77(d, J=11.3Hz, 2H), 2.54(m, 6H), 2.41(m, 2H), 2.16(d, J=11.3Hz, 2H) and 1.44(s, 6H). |
| 69 | ¹H NMR(500MHz, CDCl₃): δ=7.94(d, J=8.3Hz, 1H), 7.87(d, J=1.6Hz, 1H), 7.75(dd, J=8.3 and 2.0Hz, 1H), 7.35(m, 1H), 7.23(m, 1H), 6.98(m, 1H), 6.91(d, J=8.3Hz, 1H), 3.87(br s, 1H), 3.83(s, 3H), 3.75(br s, 1H), 3.37(s, 2H), 3.26(m, 2H), 2.78(d, J=11.0Hz, 2H), 2.56-2.30(m, 7H), 2.31(br s, 1H), 2.15(d, J=11.0Hz, 2H) and 1.44(s, 6H). |
| 70 | ¹H NMR(500MHz, CDCl₃): δ=7.94(d, J=8.3Hz, 1H), 7.87(d, J=1.6Hz, 1H), 7.75(dd, J=8.3 and 2.0Hz, 1H), 4.37(m, 1H), 3.36(m, 7H), 3.27(q, 2H), 2.77(d, J=11.4Hz, 2H), 2.57-2.45(m, 9H), 2.49(s, 4H), 2.16(d, J=11.3Hz, 2H), 1.43(s, 6H) and 1.14(t, J=7.3Hz, 3H). |
| 71 | ¹H NMR(500MHz, CDCl₃): δ=7.94(d, J=8.3Hz, 1H), 7.87(s, 1H), 7.75(dd, J=8.3 and 1.9Hz, 1H), 4.18(d, J=7.1Hz, 1H), 3.97(sept, J=6.5Hz, 1H), 3.37(s, 2H), 3.34(m, 4H), 2.77(d, J=11.3Hz, 2H), 2.56(m, 2H), 2.50(m, 2H), 2.45(m, 4H), 2.16(d, J=11.3Hz, 2H), 1.43(s, 6H) and 1.15(d, J=6.5Hz, 6H). |
| 72 | ¹H NMR(500MHz, CDCl₃): δ=7.93(d, J=8.3Hz, 1H), 7.87(s, 1H), 7.75(dd, J=8.3 and 1.8Hz, 1H), 7.17(d, J=8.8Hz, 2H), 6.69(d, J=8.8Hz, 2H), 6.15(s, 1H), 3.47(m, 4H), 3.38(s, 2H), 2.90(s, 6H), 2.78(d, J=11.3Hz, 2H), 2.57(m, 2H), 2.51(m, 6H), 2.16(d, J=11.3Hz, 2H) and 1.44(s, 6H). |
| 73 | ¹H NMR(500MHz, CDCl₃): δ=7.94(d, J=8.3Hz, 1H), 7.87(s, 1H), 7.75(dd, J=8.3 and 1.8Hz, 1H), 7.36(s, 2H), 6.59(s, 1H), 3.51(m, 4H), 3.36(s, 2H), 2.78(d, J=11.3Hz, 2H), 2.60-2.50(m, 8H), 2.17(d, J=11.3Hz, 2H) and 1.44(s, 6H). |
| 74 | ¹H NMR(500MHz, CDCl₃): δ=7.94(d, J=8.3Hz, 1H), 7.86(d, J=1.6Hz, 1H), 7.75(dd, J=8.3 and 1.9Hz, 1H), 4.60(t, $J_{H-F}$=12.5Hz, 2H), 3.81(br s, 4H), 3.46(s, 2H), 3.06(m, 6H), 2.85(d, J=11.1Hz, 2H), 2.77(m, 2H), 2.16(d, J=11.1Hz, 2H) and 1.45(s, 6H). |
| 75 | ¹H NMR(500MHz, CDCl₃): δ=7.94(d, J=8.3Hz, 1H), 7.87(d, J=1.8Hz, 1H), 7.75(dd, J=8.3 and 1.8Hz, 1H), 3.66(m, 2H), 3.48(m, 2H), 3.36(s, 2H), 3.23(q, $J_{H-F}$=10.0Hz, 2H), 2.77(d, J=11.3Hz, 2H), 2.56(m, 2H), 2.52-2.46(m, 6H), 2.16(d, J=11.3Hz, 2H) and 1.44(s, 6H). |
| 76 | ¹H NMR(500MHz, CDCl₃): δ=7.94(d, J=8.3Hz, 1H), 7.86(m, 5H), 7.74(dd, J=8.3 and 1.9Hz, 1H), 3.31(s, 2H), 3.07(m, 4H), 2.72(d, J=11.3Hz, 2H), 2.56(m, 4H), 2.49(s, 4H), 2.12(d, J=11.3Hz, 2H) and 1.41(s, 6H). |

What is claimed is:

1. A compound of the following formula I:

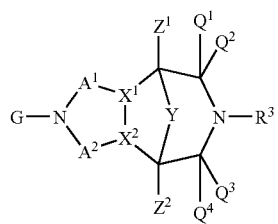

(I)

or a pharmaceutically-acceptable salt thereof;
wherein the symbols have the following meanings and are, for each occurrence, independently selected:

G is aryl, substituted aryl, heteroaryl, or substituted heteroaryl;
Y is O;
$A^1$ and $A^2$ are each independently CO and/or $CHR^1$;
$X^1$ is $CR^1$;
$X^2$ is $CR^1$;
$Z^1$ and $Z^2$ are each independently H, alkyl, substituted alkyl, alkenyl, substituted alkenyl, cycloalkyl, substituted cycloalkyl, cycloalkylalkyl, substituted cycloalkylalkyl, aryl, substituted aryl, arylalkyl, substituted arylalkyl, heterocyclo, substituted heterocyclo, heterocycloalkyl, and/or substituted heterocycloalkyl;
$Q^1$, $Q^2$, $Q^3$, and $Q^4$ are each independently H, alkyl, substituted alkyl, aryl, substituted aryl, heterocyclo, and/or substituted heterocyclo; or $Q^1$ and $Q^2$ together form =O; or $Q^3$ and $Q^4$ together form =O;
each $R^1$ and each $R^2$ are independently H, alkyl, substituted alkyl, cycloalkyl, substituted cycloalkyl, cycloalkylalkyl, substituted cycloalkylalkyl, arylalkyl, substituted arylalkyl, heterocycloalkyl, substituted heterocycloalkyl, aryl, substituted aryl, heteroaryl, substituted heteroaryl, CN, $NO_2$, F, Cl, and/or Br;
$R^3$ is H, alkyl, substituted alkyl, cycloalkyl, substituted cycloalkyl, cycloalkylalkyl, substituted cycloalkylalkyl, aryl, substituted aryl, arylalkyl, substituted arylalkyl, heterocyclo, substituted heterocyclo, heterocycloalkyl, substituted heterocycloalkyl, OH, $OR^1$, $NR^1R^2$, —C(=O)R$^1$, —C(=O)OR$^1$, —SO$_2$R$^1$, —SOR$^1$, —C(=O)NR$^1$R$^2$, —SO$_2$OR$^1$, —SO$_2$NR$^1$R$^2$, or —C(=N—CN)—NR$^1$R$^2$.

2. The compound of claim 1, or a pharmaceutically-acceptable salt thereof; in which Z$^1$ and Z$^2$ are each independently H, alkyl, and/or substituted alkyl.

3. The compound of claim 2, or a pharmaceutically-acceptable salt thereof; in which Q$^1$, Q$^2$, Q$^3$, and Q$^4$ are each independently H, alkyl, and/or substituted alkyl; or Q$^1$ and Q$^2$ together form =O; or Q$^3$ and Q$^4$ together form =O.

4. The compound of claim 3, or a pharmaceutically-acceptable salt thereof; in which G is substituted aryl.

5. The compound of claim 4, or a pharmaceutically-acceptable salt thereof; in which X$^1$ and X$^2$ are each CH.

6. A pharmaceutical composition comprising:
   a) at least one compound according to claim 1 or a pharmaceutically-acceptable salt thereof; and
   b) a pharmaceutically acceptable carrier or diluent.

7. The pharmaceutical composition of claim 6, in which Z$^1$ and Z$^2$ are each independently H, alkyl, and/or substituted alkyl.

8. The pharmaceutical composition of claim 7, in which Q$^1$, Q$^2$, Q$^3$, and Q$^4$ are each independently H, alkyl, or substituted alkyl; or Q$^1$ and Q$^2$ together form =O; or Q$^3$ and Q$^4$ together form =O.

9. The pharmaceutical composition of claim 8, in which G is substituted aryl.

10. The pharmaceutical composition of claim 9, in which X$^1$ and X$^2$ are each CH.

11. A method for treating a condition or disorder comprising administering to a mammalian species in need thereof a therapeutically effective amount of a compound according to claim 1, or a pharmaceutically-acceptable salt thereof;

wherein said condition or disorder is selected from the group consisting of: benign prostate hypertrophia, adenomas and neoplasies of the prostate, benign or malignant tumor cells containing an androgen receptor, and prostate cancer.

* * * * *

UNITED STATES PATENT AND TRADEMARK OFFICE
CERTIFICATE OF CORRECTION

| | |
|---|---|
| PATENT NO. | : 7,550,458 B2 |
| APPLICATION NO. | : 11/581873 |
| DATED | : June 23, 2009 |
| INVENTOR(S) | : James Balog et al. |

It is certified that error appears in the above-identified patent and that said Letters Patent is hereby corrected as shown below:

Claim 1, col. 108, line 55, delete "aryl,substituted" and insert -- aryl, substituted --; and Claim 1, col. 108, line 57, delete "$Q^4$together" and insert -- $Q^4$ together --.

Signed and Sealed this

Twenty-fifth Day of May, 2010

David J. Kappos
*Director of the United States Patent and Trademark Office*